US007294753B2

(12) United States Patent
Kloetzer et al.

(10) Patent No.: US 7,294,753 B2
(45) Date of Patent: Nov. 13, 2007

(54) METHOD FOR PREPARING ANTI-MIF ANTIBODIES

(75) Inventors: William S Kloetzer, Carlsbad, CA (US); Nabil Hanna, Rancho Santa Fe, CA (US)

(73) Assignee: Biogen Idec Inc., Cambridge, MA (US)

( * ) Notice: Subject to any disclaimer, the term of this patent is extended or adjusted under 35 U.S.C. 154(b) by 97 days.

(21) Appl. No.: 11/143,737

(22) Filed: Jun. 3, 2005

(65) Prior Publication Data

US 2006/0191024 A1 Aug. 24, 2006

Related U.S. Application Data

(62) Division of application No. 09/791,551, filed on Feb. 26, 2001, now abandoned.

(60) Provisional application No. 60/185,390, filed on Feb. 28, 2000, provisional application No. 60/233,625, filed on Sep. 18, 2000.

(51) Int. Cl.
*C12P 21/00* (2006.01)

(52) U.S. Cl. ...................... 800/4; 800/4; 800/5; 800/21

(58) Field of Classification Search ..................... None
See application file for complete search history.

(56) References Cited

U.S. PATENT DOCUMENTS 6,645,493 B1 * 11/2003 Bucala et al. ............ 424/145.1

FOREIGN PATENT DOCUMENTS

EP 0 162 812 A2 11/1985

OTHER PUBLICATIONS

Prusiner et al, PNAS 1993;90:10608-12.*
Rondard et al, Biochemistry 1997;36:8954-61.*
Janeway et al, Immunobiology 2001.*
Lantz et al, Immunol 1975;29:301-6.*
Goidl et al, Immunol 1975;29:629-41.*
Doria et al, Immunol 1978;35:601-11.*
Marchant et al, J Infect Disease 2006;193:1598-605.*
Bozza, et al., "Targeted Disruption of Migration Inhibitory Factor Gene Reveals Its Critical Role in Sepsis", J. Exp. Med., The Rockefeller University Press, vol. 189, No. 2, Jan. 18, 1999, pp. 341-346.
Declerck, et al., "Generation of Monoclonal antibodies against Autologous Proteins in Gene-inactivated Mice", The Journal of Biological Chemistry, vol. 270, No. 16, Apr. 14, 1995, pp. 8397-8400.
Steinhoff, et al., "Evidence for a role of macrophage migration inhibitory factor in psoriatic skin disease", British Journal of Dermatology, 1991, 141, pp. 1061-1066.
Donnelly, et al., "Regulatory role for microphage migration inhibitory factor in acute respiratory distress syndrome", Nature Medicine, vol. 3, No. 3, Mar. 1997.
Calandra, et al., "Protection from septic shock by neutralizatoin of microphage migration inhibotory factor", Nature Medicine, vol. 6, No. 2, Feb. 2000.
Calandra, et al., Macrophage Migration Inhibitory Factor: a Counter-Regulator of Glucocorticold Action and Critical Mediator of Septic Shock, Journal of Inflammmation, vol. 47, pp. 39-51 (1996).
Lan, et al., "The Pathogenic Role of Macrophage Migration Inhibitory Factor in Immunologically Induced Kidney Disease in the Rat", J. Exp. Med., vol. 185, No. 8, Apr. 21, 1997, The Rockefeller University Press.
Leech, et al., "Macrophage Migration Inhibitory Factor in Rheumatoid Arthritis", Arthritis & Rheumatism, vol. 42, No. 8, Aug. 1999, pp. 1601-1608.
Mitchell, Sustained Mitogen-activated Protein Kinase (MAPK) and Cytoplasmic Phospholipase A2 Activation by Macrophage Migration Inhibitory Factor (MIF), The Journal of Biological Chemistry, vol. 274, No. 25, Issue of Jun. 18, 1999, pp. 18100-18106.
Shimizu, et al., "High Expression of Macrophage Migration Inhibitory Factor in Human Melanoma Cells and Its Role in Tumor Cell Growth and Angiogenesis", Biochemical and Biophysical Research Communications, vol. 264, 1999, pp. 751-758.
Mitamura, et al., Macrophage Migration Inhibitory Factor Levels in the Vitreous of Patients with Proliferative Vitreoretinopathy, American Journal of Ophthalmology, Dec. 1999, pp. 763-765.
Onodera, et al., "Macrophage Migration Inhiitory Factor Up-regulates Expression of Matrix Metalloproteinases in Synovial Fibroblasts of Rheumatoid Arthritis", the Journal of Biological Chemistry, vol. 275, No. 1, Jan. 7, 2000, pp. 444-450.
Winter, et al., "antibody-based therapy XP-001005438 Humanized antibodies", Immunology today, vol. 14, No. 6, 1993, pp. 243-246.
Heiman, et al., "New Steroidal anti-inflammatory antedrugs bind to macrophage glucocorticoid receptors and inhiit nitric oxide generation", Steroids, 1998, vol. 63, Dec. 1998, pp. 644-649.
Borghesi et al., "Autologous anti-idiotypic antibody response is regulated by the level of circulating complementary idiotype," Immunology, Blackwell Science Ltd., p. 172-177, (1996).
Pearson, Nature 2002; 415;8-9.
Humpherys et al, Science 2001; 293:95-97.
Yanagimachi, Mol Cell Endocrinol 2002; 187:241-8.
Wall et al, J Dairy Sci 1997; 80:2213-24.
Denning, Nat Biotech 2001; 19:559-562.
Houdebine, J. Biotech. 1994 vol. 34.
Bozza et al, Genomics 1995;27: 412-9.
Moreadith et al., J. Mol. Med. 1997; 75:208-16.
Pera et al, Journal of Cell Science 113: 5-10 (2000).
Mullins et al (1996) J. Clin. Invest. 98, p. S39.
Liao et al., "Adhesion-dependent signaling by Macrophage migration inhibitory factor (MIF)," J. Biol. Chem., vol. 278 (No. 1), p. 76-81, 2003.

* cited by examiner

*Primary Examiner*—Q. Janice Li
(74) *Attorney, Agent, or Firm*—Pillsbury Winthrop Shaw Pittman LLP

(57) ABSTRACT

The specification provides methods of preparing high-affinity antibodies to a macrophage migration inhibitory factor (MIF) in animals in which the MIF gene has been homozygously knocked-out ($MIF^{-/-}$). Also provided are methods of preparing hybridomas which produce the anti-MIF antibodies, methods of administering the antibodies to treat inflammatory or cancerous conditions and/or diseases modulated by MIF, as well as compositions comprising said high-affinity anti-MIF antibodies.

12 Claims, 30 Drawing Sheets

MIF catalyzed keto-enol tautomerase of *p*-hydoxyphenylpyruvate

Tzung Yang, Michael Bacica and Michael LaBarre

MIF signaling events

Mitchell *et al.* 1999. JBC 274 (25):18100

Anti-MIF mab effects on MIF stimulated MMP-1 release from dermal fibroblasts

Anti-MIF mab effects on MIF + LPS lethality in BALB/c mice

10 mg LPS/kg body wt

Peter Brams and Mai-Lan Nguyen

Anti-MIF mab effects on MIF-enhanced LPS lethality in BALB/c mice
n = 9; mab 5 mg/kg at T = -2 hrs; R&R MIF 2.5 mg/kg at T = 0 and 7 hrs
05-12-00

Anti-MIF mab effects on MIF + LPS lethality in BALB/c mice

12.5 mg LPS/kg body wt

Peter Brams and Mai-Lan Nguyen

Anti-MIF mab effects on human MIF + LPS lethality in BALB/c mice
n = 9; mab 5 mg/kg at T = -2 hrs; R&R MIF 2.5 mg/kg at T = 0 and 7 hrs
05-17-00

Anti-MIF mab effects on MIF + LPS lethality in BALB/c mice

15 mg LPS/kg body wt

Peter Brams and Mai-Lan Nguyen

Anti-MIF mab effects on HUVE cell proliferation

Optimized assay for VEGF-stimulated HUVE cell proliferation

625 versus 1,250 versus 2,500 cells/well 4 versus 5 day growth

Anti-MIF mab effects on HUVE cell proliferation

2500 cells/well; 5 days

HUVE 08-31-00

Anti-MIF mab effects on MIF-enhanced arachidonic acid release transient MIF gene transfection of RAW264.7 cells

FIG.17

ANTI-MIF LIGHT CHAIN AMINO ACIDS

Leader

| | |
|---|---|
| 6B5 | MDFQVQIISF L LISASVI M SRG (SEQ ID NO: 1) |
| 10B11 | MSVLT Q V LGLLLLWLTD ARC (SEQ ID NO: 2) |
| 19B11 | MEAPAQLLFQ LSEMETDTLL LWVLLLWVPG STG (SEQ ID NO: 3) |
| 22F11 | MSVLT Q V LGLLLLWLTG ARC (SEQ ID NO: 4) |
| 29B12 | MGIKMESQFQ V LMFLLLWVSG ACA (SEQ ID NO: 5) |
| 33G7 | MSVLT Q V LGLLLLWLTG ARC (SEQ ID NO: 6) |

FR1

| | |
|---|---|
| 6B5 | QIVLTQS PAIMSAFPGE KVTIT (SEQ ID NO: 7) |
| 10B11 | DIQMTQS PASLSVSVGE TVTIT (SEQ ID NO: 8) |
| 19B11 | NIVLTQS PASLALSLGQ RATIS (SEQ ID NO: 9) |
| 22F11 | DIQMTQS PASLSASVGE TVTIT (SEQ ID NO:10) |
| 29B12 | DIVMTQS PSSLAMSVGQ RVTMS (SEQ ID NO:11) |
| 33G7 | DIQMTQS PASLSASVGE TVTIT (SEQ ID NO:12) |

CDR1

| | |
|---|---|
| 6BF | CSASS SV SY MH (SEQ ID NO:13) |
| 10B11 | CRASE NIYS N LA (SEQ ID NO:14) |
| 19B11 | CRTSE SV DSYASSF MH (SEQ ID NO:15) |
| 22F11 | CRASE NIYS Y LT (SEQ ID NO:16) |
| 29B12 | CKSSQ SLLNINQKSY LA (SEQ ID NO:17) |
| 33G7 | CRASE NIFN Y LS (SEQ ID NO:18) |

FR2

| | |
|---|---|
| 6B5 | WFQQKPGT SPKLWIY (SEQ ID NO:19) |
| 10B11 | WYQQKQGK SPQLLVY (SEQ ID NO:20) |
| 19B11 | WYQQKPGQ SPKLLIY (SEQ ID NO:21) |
| 22F11 | WFQQKQGK SPQLLVY (SEQ ID NO:22) |
| 29B12 | WYQQKPGQ SPKLLVY (SEQ ID NO:23) |
| 33G7 | WYQQKQGK SPQLLVY (SEQ ID NO:24) |

CDR2

| | |
|---|---|
| 6B5 | GTS NLAS (SEQ ID NO:25) |
| 10B11 | AAT NLAD (SEQ ID NO:26) |
| 19B11 | LAS NLES (SEQ ID NO:27) |
| 22F11 | DAK TLAE (SEQ ID NO:28) |
| 29B12 | FAS TRES (SEQ ID NO:29) |
| 33G7 | NVK TLTD (SEQ ID NO:30) |

FR3

| | |
|---|---|
| 6B5 | GVPVRF SGSGSGTSYS LTISRMEAED AATYYC (SEQ ID NO:31) |
| 10B11 | GVPSRF SGSGSGTQYS LNIYSLQPED FGSYYC (SEQ ID NO:32) |
| 19B11 | GVPARF SGSGSRTDFT LTIDPVEADD AATYYC (SEQ ID NO:33) |
| 22F11 | GVPSSF SGSGSGTQFS LKIISLQPEH FGSYYC (SEQ ID NO:34) |
| 29B12 | GVPDRF IGSGSGTDFT LTISSVQAED LADYFC (SEQ ID NO:35) |
| 33G7 | GVPSRF SGSGSGTQFS LKINSLQPED FGSYYC (SEQ ID NO:36) |

CDR3

| | |
|---|---|
| 6B5 | QQRSSYPWT (SEQ ID NO:37) |
| 10B11 | QHFWGTPYT (SEQ ID NO:38) |
| 19B11 | QQSNEDPRT (SEQ ID NO:39) |
| 22F11 | QHHYGRPYT (SEQ ID NO:40) |
| 29B12 | QQHYSTPPT (SEQ ID NO:41) |
| 33G7 | QHHYDTPYT (SEQ ID NO:42) |

FR4

| | |
|---|---|
| 6B5 | FGGGTKLEIK (SEQ ID NO:43) |
| 10B11 | FGGGTKLEIK (SEQ ID NO:44) |
| 19B11 | FGGGTQLEIK (SEQ ID NO:45) |
| 22F11 | FGGGTKLEIK (SEQ ID NO:46) |
| 29B12 | FGSGTKLEIK (SEQ ID NO:47) |
| 33G7 | FGRGTKLEIK (SEQ ID NO:48) |

FIG. 18

6B5 Light Chain

```
              21          30          39          48          57          66
5' ATG GAT TTT CAG GTG CAG ATT TTC AGC TTC CTG CTA ATC AGT GCC TCA GTC ATA
   --- --- --- --- --- --- --- --- --- --- --- --- --- --- --- --- --- ---
   Met Asp Phe Gln Val Gln Ile Phe Ser Phe Leu Leu Ile Ser Ala Ser Val Ile

              75          84          93          102         111         120
   ATG | TCC AGA GGA CAA AT~ GTT CTC ACC CAG TCT CCA GCA ATC ATG TCT GCA TTT
   --- | --- --- --- --- --- --- --- --- --- --- --- --- --- --- --- --- ---
   Met | Ser Arg Gly Gln Ile Val Leu Thr Gln Ser Pro Ala Ile Met Ser Ala Phe

              129         136         147         156         165         174
   CCG GGG GAG AAG GTC ACC ATA ACC TGC AGT GCC AGC TCA AGT GTA AGT TAC ATG
   --- --- --- --- --- --- --- --- --- --- --- --- --- --- --- --- --- ---
   Pro Gly Glu Lys Val Thr Ile Thr Cys Ser Ala Ser Ser Ser Val Ser Tyr Met

              183         192         201         210         219         228
   CAC TGG TTC CAG CAG AAG CCA GGC ACT TCT CCC AAA CTC TGG ATT TAT GGG ACA
   --- --- --- --- --- --- --- --- --- --- --- --- --- --- --- --- --- ---
   His Trp Phe Gln Gln Lys Pro Gly Thr Ser Pro Lys Leu Trp Ile Tyr Gly Thr

              237         246         255         264         273         282
   TCC AAC CTG GCT TCT GGA GTC CCT GTT CGC TTC AGT GGC AGT GGA TCT GGG ACC
   --- --- --- --- --- --- --- --- --- --- --- --- --- --- --- --- --- ---
   Ser Asn Leu Ala Ser Gly Val Pro Val Arg Phe Ser Gly Ser Gly Ser Gly Thr

              291         300         309         318         327         336
   TCT TAC TCT CTC ACA ATC AGC CGA ATG GAG GCT GAA GAT GCT GCC ACT TAT TAC
   --- --- --- --- --- --- --- --- --- --- --- --- --- --- --- --- --- ---
   Ser Tyr Ser Leu Thr Ile Ser Arg Met Glu Ala Glu Asp Ala Ala Thr Tyr Tyr

              345         354         363         372         381         390
   TGC CAG CAA AGG AGT AGT TAC CCG TGG ACG TTC GGT GGA GGC ACC AAG CTG GAA
   --- --- --- --- --- --- --- --- --- --- --- --- --- --- --- --- --- ---
   Cys Gln Gln Arg Ser Ser Tyr Pro Trp Thr Phe Gly Gly Gly Thr Lys Leu Glu

              399
   ATC AAA CGT ACG 3' (SEQ ID NO:49)
   --- --- --- ---    (SEQ ID NO:50)
   Ile Lys Arg Thr
```

FIG. 19

10B11 Light Chain

```
               21                  30                  39                  48                  57                  66
5'  ATG AGT GTG CTC ACT CAG GTC CTG GGG TTG CTG CTG CTG TGG CTT ACA GAT GCC
    --- --- --- --- --- --- --- --- --- --- --- --- --- --- --- --- --- ---
    Met Ser Val Leu Thr Gln Val Leu Gly Leu Leu Leu Leu Trp Leu Thr Asp Ala

               75                  84                  93                 102                 111                 120
    AGA TGT | GAC ATC CAG ATG ACT CAG TCT CCA GCC TCC CTA TCT GTA TCT GTG GGA
    --- --- | --- --- --- --- --- --- --- --- --- --- --- --- --- --- --- ---
    Arg Cys | Asp Ile Gln Met Thr Gln Ser Pro Ala Ser Leu Ser Val Ser Val Gly

               129                 138                 147                 156                 165                 174
    GAA ACT GTC ACC ATC ACA TGT CGA GCA AGT GAG AAT ATT TAC AGT AAT TTA GCA
    --- --- --- --- --- --- --- --- --- --- --- --- --- --- --- --- --- ---
    Glu Thr Val Thr Ile Thr Cys Arg Ala Ser Glu Asn Ile Tyr Ser Asn Leu Ala

               183                 192                 201                 210                 219                 228
    TGG TAT CAG CAG AAA CAG GGA AAA TCT CCT CAG CTC CTG GTC TAT GCT GCA ACA
    --- --- --- --- --- --- --- --- --- --- --- --- --- --- --- --- --- ---
    Trp Tyr Gln Gln Lys Gln Gly Lys Ser Pro Gln Leu Leu Val Tyr Ala Ala Thr

               237                 246                 255                 264                 273                 282
    AAC TTA GCA GAT GGA GTG CCG TCA AGG TTC AGT GGC AGT GGA TCA GGC ACA CAG
    --- --- --- --- --- --- --- --- --- --- --- --- --- --- --- --- --- ---
    Asn Leu Ala Asp Gly Val Pro Ser Arg Phe Ser Gly Ser Gly Ser Gly Thr Gln

               291                 300                 309                 318                 327                 336
    TAT TCC CTC AAT ATC TAC AGC CTG CAG CCT GAA GAT TTT GGA AGT TAT TAC TGT
    --- --- --- --- --- --- --- --- --- --- --- --- --- --- --- --- --- ---
    Tyr Ser Leu Asn Ile Tyr Ser Leu Gln Pro Glu Asp Phe Gly Ser Tyr Tyr Cys

               345                 354                 363                 372                 381                 390
    CAA CAT TTT TGG GGT ACT CCG TAC ACG TTC GGA GGG GGG ACC AAG CTG GAA ATC
    --- --- --- --- --- --- --- --- --- --- --- --- --- --- --- --- --- ---
    Gln His Phe Trp Gly Thr Pro Tyr Thr Phe Gly Gly Gly Thr Lys Leu Glu Ile

               399
    AAA CGT ACG 3'  (SEQ ID NO:51)
    --- --- ---     (SEQ ID NO:52)
    Lys Arg Thr
```

*FIG. 20*

19B11 Light Chain

```
            21              30              39              48              57          66
5' ATG GAA GCC CCA GCT CAG CTT CTC TTC CAG CTC TCA GAG ATG GAG ACA GAC ACA
   --- --- --- --- --- --- --- --- --- --- --- --- --- --- --- --- --- ---
   Met Glu Ala Pro Ala Gln Leu Leu Phe Gln Leu Ser Glu Met Glu Thr Asp Thr

            75              84              93              102             111         120
   CTC CTG CTA TGG GTG CTG CTG CTC TGG GTT CCA GGT TCC ACA GGT | AAC ATT GTG
   --- --- --- --- --- --- --- --- --- --- --- --- --- --- --- | --- --- ---
   Leu Leu Leu Trp Val Leu Leu Leu Trp Val Pro Gly Ser Thr Gly | Asn Ile Val

            129             138             147             156             165         174
   CTG ACC CAA TCT CCA GCT TCT TTG GCT CTG TCT CTA GGG CAG AGG GCC ACC ATA
   --- --- --- --- --- --- --- --- --- --- --- --- --- --- --- --- --- ---
   Leu Thr Gln Ser Pro Ala Ser Leu Ala Leu Ser Leu Gly Gln Arg Ala Thr Ile

            183             192             201             210             219         228
   TCC TGC AGA ACC AGC GAA AGT GTT GAT AGT TAT GCC AGT AGT TTT ATG CAC TGG
   --- --- --- --- --- --- --- --- --- --- --- --- --- --- --- --- --- ---
   Ser Cys Arg Thr Ser Glu Ser Val Asp Ser Tyr Ala Ser Ser Phe Met His Trp

            237             246             255             264             273         282
   TAC CAG CAG AAA CCA GGA CAG TCA CCC AAA CTC CTC ATC TAT CTT GCA TCC AAC
   --- --- --- --- --- --- --- --- --- --- --- --- --- --- --- --- --- ---
   Tyr Gln Gln Lys Pro Gly Gln Ser Pro Lys Leu Leu Ile Tyr Leu Ala Ser Asn

            291             300             309             318             327         336
   CTA GAA TCT GGG GTC CCT GCC AGG TTC AGT GGC AGT GGG TCT AGG ACA GAC TTC
   --- --- --- --- --- --- --- --- --- --- --- --- --- --- --- --- --- ---
   Leu Glu Ser Gly Val Pro Ala Arg Phe Ser Gly Ser Gly Ser Arg Thr Asp Phe

            345             354             363             372             381         390
   ACC CTC ACC ATT GAT CCT GTG GAG GCT GAT GAT GCT GCA ACC TAT TAC TGT CAG
   --- --- --- --- --- --- --- --- --- --- --- --- --- --- --- --- --- ---
   Thr Leu Thr Ile Asp Pro Val Glu Ala Asp Asp Ala Ala Thr Tyr Tyr Cys Gln

            399             408             417             426             435         444
   CAA AGT AAT GAG GAT CCT CGG ACG TTC GGT GGA GGC ACC CAG CTG GAA ATC AAA
   --- --- --- --- --- --- --- --- --- --- --- --- --- --- --- --- --- ---
   Gln Ser Asn Glu Asp Pro Arg Thr Phe Gly Gly Gly Thr Gln Leu Glu Ile Lys

   CGT ACG 3'  (SEQ ID NO:53)
   --- ---
   Arg Thr     (SEQ ID NO:54)
```

FIG. 21

22F11 Light Chain

```
                21                  30                  39                  48                  57                  66
5' ATG AGT GTG CTC ACT CAG GTC CTG GGG TTG CTG CTG CTG TGG CTT ACA GGT GCC
   --- --- --- --- --- --- --- --- --- --- --- --- --- --- --- --- --- ---
   Met Ser Val Leu Thr Gln Val Leu Gly Leu Leu Leu Leu Trp Leu Thr Gly Ala

                75                  84                  93                 102                 111                 120
   AGA TGT | GAC ATC CAG ATG ACT CAG TCT CCA GCC TCC CTA TCT GCA TCT GTG GGA
   --- --- | --- --- --- --- --- --- --- --- --- --- --- --- --- --- --- ---
   Arg Cys | Asp Ile Gln Met Thr Gln Ser Pro Ala Ser Leu Ser Ala Ser Val Gly

               129                 138                 147                 156                 165                 174
   GAA ACT GTC ACC ATC ACA TGT CGA GCA AGT GAG AAT ATT TAC AGT TAT TTA ACA
   --- --- --- --- --- --- --- --- --- --- --- --- --- --- --- --- --- ---
   Glu Thr Val Thr Ile Thr Cys Arg Ala Ser Glu Asn Ile Tyr Ser Tyr Leu Thr

               183                 192                 201                 210                 219                 228
   TGG TTT CAG CAG AAA CAG GGA AAA TCT CCT CAG CTC CTG GTC TAT GAT GCA AAA
   --- --- --- --- --- --- --- --- --- --- --- --- --- --- --- --- --- ---
   Trp Phe Gln Gln Lys Gln Gly Lys Ser Pro Gln Leu Leu Val Tyr Asp Ala Lys

               237                 246                 255                 264                 273                 282
   ACC TTA GCA GAA GGT GTG CCA TCA AGT TTC AGT GGC AGT GGA TCA GGC ACA CAG
   --- --- --- --- --- --- --- --- --- --- --- --- --- --- --- --- --- ---
   Thr Leu Ala Glu Gly Val Pro Ser Ser Phe Ser Gly Ser Gly Ser Gly Thr Gln

               291                 300                 309                 318                 327                 336
   TTT TCT CTT AAG ATC ATC AGC CTG CAG CCT GAA CAT TTT GGG AGT TAT TAC TGT
   --- --- --- --- --- --- --- --- --- --- --- --- --- --- --- --- --- ---
   Phe Ser Leu Lys Ile Ile Ser Leu Gln Pro Glu His Phe Gly Ser Tyr Tyr Cys

               345                 354                 363                 372                 381                 390
   CAA CAT CAT TAT GGT CGA CCA TAC ACG TTC GGA GGG GGG ACC AAG CTG GAA ATC
   --- --- --- --- --- --- --- --- --- --- --- --- --- --- --- --- --- ---
   Gln His His Tyr Gly Arg Pro Tyr Thr Phe Gly Gly Gly Thr Lys Leu Glu Ile

               399
   AAA CGT ACG 3'  (SEQ ID NO:55)
   --- --- ---     (SEQ ID NO:56)
   Lys Arg Thr
```

FIG. 22

29B12 Light Chain

```
                21                30                39                48                57                66
5' ATG GGC ATC AAG ATG GAG TCA CAG ATT CTG GTC CTC ATG TTT CTT CTG CTC TGG
   --- --- --- --- --- --- --- --- --- --- --- --- --- --- --- --- --- ---
   Met Gly Ile Lys Met Glu Ser Gln Ile Leu Val Leu Met Phe Leu Leu Leu Trp

                75                84                  93                102               111               120
   GTA TCT GGT GCC TGT GCA | GAC ATT GTG ATG ACA CAG TCT CCA TCC TCC CTG GCT
   --- --- --- --- --- --- | --- --- --- --- --- --- --- --- --- --- --- ---
   Val Ser Gly Ala Cys Ala | Asp Ile Val Met Thr Gln Ser Pro Ser Ser Leu Ala

                129               138               147               156               165               174
   ATG TCA GTA GGA CAG AGG GTC ACT ATG AGC TGC AAG TCC AGT CAG AGC CTT TTA
   --- --- --- --- --- --- --- --- --- --- --- --- --- --- --- --- --- ---
   Met Ser Val Gly Gln Arg Val Thr Met Ser Cys Lys Ser Ser Gln Ser Leu Leu

                183               192               201               210               219               228
   AAT ATC AAT CAA AAG AGC TAT TTG GCC TGG TAC CAG CAG AAA CCA GGA CAG TCT
   --- --- --- --- --- --- --- --- --- --- --- --- --- --- --- --- --- ---
   Asn Ile Asn Gln Lys Ser Tyr Leu Ala Trp Tyr Gln Gln Lys Pro Gly Gln Ser

                237               246               255               264               273               282
   CCT AAA CTT CTG GTA TAC TTT GCA TCC ACT AGG GAA TCT GGG GTC CCT GAT CGC
   --- --- --- --- --- --- --- --- --- --- --- --- --- --- --- --- --- ---
   Pro Lys Leu Leu Val Tyr Phe Ala Ser Thr Arg Glu Ser Gly Val Pro Asp Arg

                291               300               309               318               327               336
   TTC ATA GGC AGT GGA TCT GGG ACA GAT TTC ACT CTT ACC ATC AGC AGT GTG CAG
   --- --- --- --- --- --- --- --- --- --- --- --- --- --- --- --- --- ---
   Phe Ile Gly Ser Gly Ser Gly Thr Asp Phe Thr Leu Thr Ile Ser Ser Val Gln

                345               354               363               372               381               390
   GCT GAA GAC CTG GCA GAT TAC TTC TGT CAG CAA CAT TAT AGT ACT CCT CCC ACG
   --- --- --- --- --- --- --- --- --- --- --- --- --- --- --- --- --- ---
   Ala Glu Asp Leu Ala Asp Tyr Phe Cys Gln Gln His Tyr Ser Thr Pro Pro Thr

                399               408               417               426
   TTC GGT TCT GGG ACC AAG CTG GAA ATC AAA CGT ACG 3'  (SEQ ID NO:57)
   --- --- --- --- --- --- --- --- --- --- --- ---     (SEQ ID NO:58)
   Phe Gly Ser Gly Thr Lys Leu Glu Ile Lys Arg Thr
```

FIG. 23

33G7 Light Chain

```
              21        30        39        48        57        66
5'ATG AGT GTG CTC ACT CAG GTC CTG GGG TTG CTG CTG CTG TGG CTT ACA GGT GCC
  --- --- --- --- --- --- --- --- --- --- --- --- --- --- --- --- --- ---
  Met Ser Val Leu Thr Gln Val Leu Gly Leu Leu Leu Leu Trp Leu Thr Gly Ala

              75        84        93       102       111       120
  AGA TGT | GAC ATC CAG ATG ACT CAG TCT CCA GCC TCC CTA TCT GCA TCT GTG GGA
  --- --- | --- --- --- --- --- --- --- --- --- --- --- --- --- --- --- ---
  Arg Cys | Asp Ile Gln Met Thr Gln Ser Pro Ala Ser Leu Ser Ala Ser Val Gly

          129         138         147         156         165         174
  GAA ACT GTC ACC ATC ACA TGT CGC GCA AGT GAG AAT ATT TTC AAT TAT TTA TCA
  --- --- --- --- --- --- --- --- --- --- --- --- --- --- --- --- --- ---
  Glu Thr Val Thr Ile Thr Cys Arg Ala Ser Glu Asn Ile Phe Asn Tyr Leu Ser

          183         192         201         210         219         228
  TGG TAT CAG CAG AAA CAG GGA AAA TCT CCT CAG CTC CTG GTC TAT AAT GTA AAA
  --- --- --- --- --- --- --- --- --- --- --- --- --- --- --- --- --- ---
  Trp Tyr Gln Gln Lys Gln Gly Lys Ser Pro Gln Leu Leu Val Tyr Asn Val Lys

          237         246         255         264         273         282
  ACC TTA ACA GAT GGT GTG CCA TCA AGG TTC AGT GGC AGT GGC TCA GGC ACA CAG
  --- --- --- --- --- --- --- --- --- --- --- --- --- --- --- --- --- ---
  Thr Leu Thr Asp Gly Val Pro Ser Arg Phe Ser Gly Ser Gly Ser Gly Thr Gln

          291         300         309         318         327         336
  TTT TCT CTG AAG ATC AAC AGC CTG CAG CCT GAA GAT TTT GGC AGT TAT TAC TGT
  --- --- --- --- --- --- --- --- --- --- --- --- --- --- --- --- --- ---
  Phe Ser Leu Lys Ile Asn Ser Leu Gln Pro Glu Asp Phe Gly Ser Tyr Tyr Cys

          345         354         363         372         381         390
  CAA CAT CAT TAT GAT ACT CCG TAC ACG TTC GGA AGG GGG ACC AAG CTG GAA ATC
  --- --- --- --- --- --- --- --- --- --- --- --- --- --- --- --- --- ---
  Gln His His Tyr Asp Thr Pro Tyr Thr Phe Gly Arg Gly Thr Lys Leu Glu Ile

          399
  AAA CGT ACG 3'  (SEQ ID NO:59)
  --- --- ---     (SEQ ID NO:60)
  Lys Arg Thr
```

FIG. 24

Anti-MIF Heavy Chain Amino Acids

Leader

| | Leader |
|---|---|
| 6B5 | MR VLILLWL FTAFPGILS (SEQ ID NO:61) |
| 10B11 | M GWSWVFLFL LSGTAGVLS (SEQ ID NO:62) |
| 19B11 | M AWVWTLLFL MAAAQSAQA (SEQ ID NO:63) |
| 22F11 | |
| 29B12 | MHARAAASVM DICRIRLTSD MDFGLSLVFL VLVLKGVQC (SEQ ID NO:64) |
| 33G7 | MM VLSLLYL LTAIPGILS (SEQ ID NO:65) |

Framework 1

| | Framework 1 |
|---|---|
| 6B5 | D VQLQESGPGL VKPSQSLSLT CTVTGSSIT (SEQ ID NO:66) |
| 10B11 | E VQLQQSGPEL VKPGASVRIS CKTSGYTIT (SEQ ID NO:67) |
| 19B11 | Q IQLVQSGPEL KKPGETVKIS CKASGYSFR (SEQ ID NO:68) |
| 22F11 | E VKLEESGGGL VQPGGSMKLS CAASGFTFG (SEQ ID NO:69) |
| 29B12 | E VKLVESGGGS VQPGGSLKLS CATSGFIFS (SEQ ID NO:70) |
| 33G7 | D VQLQESGPDL VKPSQSLSLT CSVTGYSIT (SEQ ID NO:71) |

| | CDR 1 | Framework 2 |
|---|---|---|
| 6B5 | S DYAWH (SEQ ID NO:72) | WIRQF PGNKLEWMG (SEQ ID NO:78) |
| 10B11 | EYTMH (SEQ ID NO:73) | WMKQS HEKSLEWIG (SEQ ID NO:79) |
| 19B11 | NYGMN (SEQ ID NO:74) | WVSQP PGKGLEWMG (SEQ ID NO:80) |
| 22F11 | DAWMY (SEQ ID NO:75) | WVRQS PEKGLEWVA (SEQ ID NO:81) |
| 29B12 | DYYMY (SEQ ID NO:76) | WVRQT PEKRLEWVA (SEQ ID NO:82) |
| 33G7 | S GYYWN (SEQ ID NO:77) | WIRQF PGNKLEWVG (SEQ ID NO:83) |

| | CDR 2 |
|---|---|
| 6B5 | Y ISFSGSTG YNPSLKS (SEQ ID NO:84) |
| 10B11 | G ITPNTGVLS DNQKFRG (SEQ ID NO:85) |
| 19B11 | W INTYTGEPT YADDFKG (SEQ ID NO:86) |
| 22F11 | E IRSKAHNHAT YYAESVKG (SEQ ID NO:87) |
| 29B12 | Y ISIGSGN T YYPDTVKG (SEQ ID NO:88) |
| 33G7 | Y LSYDGSKS HNPSLRN (SEQ ID NO:89) |

| | Framework 3 |
|---|---|
| 6B5 | RF SITRDTSKNQ FFLQLNSVTT EDTATYYCAR (SEQ ID NO:90) |
| 10B11 | KA TLTVDKSSNT AYMELRSLTS ADSAVYYCAR (SEQ ID NO:91) |
| 19B11 | RF AFSLDTSAST AYLTINNLKN EDTATYFCAR (SEQ ID NO:92) |
| 22F11 | RF TISRDDSKSS VYLQMSSLRA EDTGIYYCTS (SEQ ID NO:93) |
| 29B12 | RF TISRDIAKNT LYLQMSRLKS EDTAMYYCVR (SEQ ID NO:94) |
| 33G7 | RI SITRDPSKNQ FFLKLNSVTT EDTATYYCAR (SEQ ID NO:95) |

| | CDR 3 | Framework |
|---|---|---|
| 6B5 | EA YGYDV GYFDY (SEQ ID NO:96) | WGQGT TLTVSS (SEQ ID NO:102) AS |
| 10B11 | RGNNYYGSSP W FAY (SEQ ID NO:97) | WGQGT LVTVSS (SEQ ID NO:103) AS |
| 19B11 | SNYGNY FDY (SEQ ID NO:98) | WGQGT TLTVSS (SEQ ID NO:104) AS |
| 22F11 | HH Y GSS WYFDV (SEQ ID NO:99) | WGAGT TVTVSA (SEQ ID NO:105) AS |
| 29B12 | GRLRF LFD YAMDY (SEQ ID NO:100) | WGQGT SVTVSS (SEQ ID NO:106) AS |
| 33G7 | GGKIFYGSSY DPFAY (SEQ ID NO:101) | WGQGT LVTVSS (SEQ ID NO:107) AS |

FIG. 25

6B5 Heavy Chain

```
                15          24          33          42          51          60
5'  ATG AGA GTG CTG ATT CTT TTG TGG CTG TTC ACA GCC TTT CCT GGT ATC CTG TCT
    --- --- --- --- --- --- --- --- --- --- --- --- --- --- --- --- --- ---
    Met Arg Val Leu Ile Leu Leu Trp Leu Phe Thr Ala Phe Pro Gly Ile Leu Ser

                69          78          87          96         105         114
  | GAT GTG CAG CTT CAG GAG TCG GGA CCT GGC CTG GTG AAA CCT TCT CAG TCT CTG
  | --- --- --- --- --- --- --- --- --- --- --- --- --- --- --- --- --- ---
  | Asp Val Gln Leu Gln Glu Ser Gly Pro Gly Leu Val Lys Pro Ser Gln Ser Leu

               123         132         141         150         159         168
    TCC CTC ACC TGC ACT GTC ACT GGC TCC TCA ATC ACC AGT GAT TAT GCC TGG CAC
    --- --- --- --- --- --- --- --- --- --- --- --- --- --- --- --- --- ---
    Ser Leu Thr Cys Thr Val Thr Gly Ser Ser Ile Thr Ser Asp Tyr Ala Trp His

               177         186         195         204         213         222
    TGG ATC CGG CAG TTT CCA GGA AAC AAA CTG GAG TGG ATG GGC TAC ATA AGC TTC
    --- --- --- --- --- --- --- --- --- --- --- --- --- --- --- --- --- ---
    Trp Ile Arg Gln Phe Pro Gly Asn Lys Leu Glu Trp Met Gly Tyr Ile Ser Phe

               231         240         249         258         267         276
    AGT GGT AGC ACT GGC TAC AAC CCA TCT CTC AAA AGT CGA TTC TCT ATC ACT CGA
    --- --- --- --- --- --- --- --- --- --- --- --- --- --- --- --- --- ---
    Ser Gly Ser Thr Gly Tyr Asn Pro Ser Leu Lys Ser Arg Phe Ser Ile Thr Arg

               285         294         303         312         321         330
    GAC ACA TCC AAG AAC CAG TTC TTC CTG CAG TTG AAT TCT GTG ACT ACT GAG GAC
    --- --- --- --- --- --- --- --- --- --- --- --- --- --- --- --- --- ---
    Asp Thr Ser Lys Asn Gln Phe Phe Leu Gln Leu Asn Ser Val Thr Thr Glu Asp

               339         348         357         366         375         384
    ACA GCC ACA TAT TAC TGT GCA AGA GAG GCT TAT GGT TAT GAC GTG GGC TAC TTT
    --- --- --- --- --- --- --- --- --- --- --- --- --- --- --- --- --- ---
    Thr Ala Thr Tyr Tyr Cys Ala Arg Glu Ala Tyr Gly Tyr Asp Val Gly Tyr Phe

               393         402         411         420         429
    GAC TAC TGG GGC CAA GGC ACC ACT CTC ACC GTC TCC TCA GCT AGC 3'
    --- --- --- --- --- --- --- --- --- --- --- --- --- --- ---
    Asp Tyr Trp Gly Gln Gly Thr Thr Leu Thr Val Ser Ser Ala Ser
```

(SEQ ID NO:108)
(SEQ ID NO:109)

FIG. 26

10B11 Heavy Chain

```
                9                  18                  27                  36                  45                  54
5'  GTC GAC ATG GGA TGG AGC GGG ATC TTT ATC TTT CTC CTG TCA GGA ACT GCA GGT
    --- --- --- --- --- --- --- --- --- --- --- --- --- --- --- --- --- ---
    Val Asp Met Gly Trp Ser Gly Ile Phe Ile Phe Leu Leu Ser Gly Thr Ala Gly

                63                 72                  81                  90                  99                  108
    GTC CTC TCT | GAG GTC CAG CTG CAA CAG TCT GGA CCT GAG CTG GTG AAG CCT GGG
    --- --- --- | --- --- --- --- --- --- --- --- --- --- --- --- --- --- ---
    Val Leu Ser | Glu Val Gln Leu Gln Gln Ser Gly Pro Glu Leu Val Lys Pro Gly

                117                 126                 135                 144                 153                 162
    GCT TCA GTG AGG ATA TCC TGC AAG ACC TCT GGA TAC ACA ATC ACT GAA TAC ACC
    --- --- --- --- --- --- --- --- --- --- --- --- --- --- --- --- --- ---
    Ala Ser Val Arg Ile Ser Cys Lys Thr Ser Gly Tyr Thr Ile Thr Glu Tyr Thr

                171                 180                 189                 198                 207                 216
    ATG CAC TGG ATG AAG CAG AGC CAT GAA AAG AGC CTT GAG TGG ATT GGA GGT ATT
    --- --- --- --- --- --- --- --- --- --- --- --- --- --- --- --- --- ---
    Met His Trp Met Lys Gln Ser His Glu Lys Ser Leu Glu Trp Ile Gly Gly Ile

                225                 234                 243                 252                 261                 270
    ACT CCA AAC ACT GGT GTT CTT AGT GAC AAT CAG AAG TTC AGG GGC AAG GCC ACA
    --- --- --- --- --- --- --- --- --- --- --- --- --- --- --- --- --- ---
    Thr Pro Asn Thr Gly Val Leu Ser Asp Asn Gln Lys Phe Arg Gly Lys Ala Thr

                279                 288                 297                 306                 315                 324
    TTG ACT GTA GAC AAG TCC TCC AAC ACA GCC TAC ATG GAG CTC CGC AGC CTG ACA
    --- --- --- --- --- --- --- --- --- --- --- --- --- --- --- --- --- ---
    Leu Thr Val Asp Lys Ser Ser Asn Thr Ala Tyr Met Glu Leu Arg Ser Leu Thr

                333                 342                 351                 360                 369                 378
    TCT GCG GAT TCT GCA GTC TAT TAC TGT GCA AGA AGG GGA AAT AAT TAC TAC GGT
    --- --- --- --- --- --- --- --- --- --- --- --- --- --- --- --- --- ---
    Ser Ala Asp Ser Ala Val Tyr Tyr Cys Ala Arg Arg Gly Asn Asn Tyr Tyr Gly

                387                 396                 405                 414                 423                 432
    AGT AGT CCC TGG TTT GCT TAC TGG GGC CAA GGG ACT CTG GTC ACC GTC TCC GCA
    --- --- --- --- --- --- --- --- --- --- --- --- --- --- --- --- --- ---
    Ser Ser Pro Trp Phe Ala Tyr Trp Gly Gln Gly Thr Leu Val Thr Val Ser Ala

    GCT AGC 3'  (SEQ ID NO:110)
    --- ---
    Ala Ser     (SEQ ID NO:111)
```

FIG. 27

19B11 Heavy Chain

```
            15          24          33          42          51          60
5' ATG GAT TGG GTG TGG ACC TTG CTA TTC CTG ATG GCA GCT GCC CAA AGT GCC CAA
   --- --- --- --- --- --- --- --- --- --- --- --- --- --- --- --- --- ---
   Met Asp Trp Val Trp Thr Leu Leu Phe Leu Met Ala Ala Ala Gln Ser Ala Gln

             69          78          87          96         105         114
   GCA | CAG ATC CAG TTG GTG CAG TCT GGA CCT GAG CTG AAG AAG CCT GGA GAG ACA
   --- | --- --- --- --- --- --- --- --- --- --- --- --- --- --- --- --- ---
   Ala | Gln Ile Gln Leu Val Gln Ser Gly Pro Glu Leu Lys Lys Pro Gly Glu Thr

           123         132         141         150         159         168
   GTC AAG ATC TCC TGC AAG GCT TCT GGA TAT TCC TTC AGA AAC TAT GGA ATG AAC
   --- --- --- --- --- --- --- --- --- --- --- --- --- --- --- --- --- ---
   Val Lys Ile Ser Cys Lys Ala Ser Gly Tyr Ser Phe Arg Asn Tyr Gly Met Asn

           177         186         195         204         213         222
   TGG GTG AGT CAG CCT CCA GGA AAG GGT TTA GAA TGG ATG GGC TGG ATA AAC ACC
   --- --- --- --- --- --- --- --- --- --- --- --- --- --- --- --- --- ---
   Trp Val Ser Gln Pro Pro Gly Lys Gly Leu Glu Trp Met Gly Trp Ile Asn Thr

           231         240         249         258         267         276
   TAC ACT GGA GAG CCA ACA TAT GCT GAT GAC TTC AAG GGA CGG TTT GCC TTC TCT
   --- --- --- --- --- --- --- --- --- --- --- --- --- --- --- --- --- ---
   Tyr Thr Gly Glu Pro Thr Tyr Ala Asp Asp Phe Lys Gly Arg Phe Ala Phe Ser

           285         294         303         312         321         330
   TTG GAC ACC TCT GCC AGT ACT GCC TAT TTG ACG ATC AAC AAC CTC AAA AAT GAA
   --- --- --- --- --- --- --- --- --- --- --- --- --- --- --- --- --- ---
   Leu Asp Thr Ser Ala Ser Thr Ala Tyr Leu Thr Ile Asn Asn Leu Lys Asn Glu

           339         348         357         366         375         384
   GAC ACG GCT ACA TAT TTC TGT GCA AGA TCG AAT TAT GGT AAC TAC TTT GAC TAC
   --- --- --- --- --- --- --- --- --- --- --- --- --- --- --- --- --- ---
   Asp Thr Ala Thr Tyr Phe Cys Ala Arg Ser Asn Tyr Gly Asn Tyr Phe Asp Tyr

           393         402         411         420
   TGG GGC CAG GGC ACC ACT CTC ACT GTC TCT GCA GCT AGC 3' (SEQ ID NO:112)
   --- --- --- --- --- --- --- --- --- --- --- --- ---    (SEQ ID NO:113)
   Trp Gly Gln Gly Thr Thr Leu Thr Val Ser Ala Ala Ser
```

FIG. 28

22F11 Heavy Chain
(no leader)

```
                9                 18                27                36                45                54
5' | GAA GTG AAG CTT GAG GAG TCT GGA GGA GGC TTG GTG CAA CCT GGA GGA TCC ATG
   | --- --- --- --- --- --- --- --- --- --- --- --- --- --- --- --- --- ---
   | Glu Val Lys Leu Glu Glu Ser Gly Gly Gly Leu Val Gln Pro Gly Gly Ser Met

            63                72                81                90                99                108
   AAA CTC TCT TGT GCT GCC TCT GGA TTC ACT TTT GGT GAC GCC TGG ATG TAC TGG
   --- --- --- --- --- --- --- --- --- --- --- --- --- --- --- --- --- ---
   Lys Leu Ser Cys Ala Ala Ser Gly Phe Thr Phe Gly Asp Ala Trp Met Tyr Trp

            117               126               135               144               153               162
   GTC CGC CAG TCT CCA GAG AAG GGG CTT GAG TGG GTT GCT GAA ATT AGA AGC AAA
   --- --- --- --- --- --- --- --- --- --- --- --- --- --- --- --- --- ---
   Val Arg Gln Ser Pro Glu Lys Gly Leu Glu Trp Val Ala Glu Ile Arg Ser Lys

            171               180               189               198               207               216
   GCT CAT AAT CAT GCA ACA TAC TAT GCT GAG TCT GTG AAA GGG AGG TTC ACC ATC
   --- --- --- --- --- --- --- --- --- --- --- --- --- --- --- --- --- ---
   Ala His Asn His Ala Thr Tyr Tyr Ala Glu Ser Val Lys Gly Arg Phe Thr Ile

            225               234               243               252               261               270
   TCA AGA GAT GAT TCC AAA AGT AGT GTC TAC CTG CAA ATG AGC AGC TTA AGA GCT
   --- --- --- --- --- --- --- --- --- --- --- --- --- --- --- --- --- ---
   Ser Arg Asp Asp Ser Lys Ser Ser Val Tyr Leu Gln Met Ser Ser Leu Arg Ala

            279               288               297               306               315               324
   GAA GAC ACT GGC ATT TAT TAC TGT ACC TCC CAT CAC TAC GGC AGT AGC TGG TAC
   --- --- --- --- --- --- --- --- --- --- --- --- --- --- --- --- --- ---
   Glu Asp Thr Gly Ile Tyr Tyr Cys Thr Ser His His Tyr Gly Ser Ser Trp Tyr

            333               342               351               360               369
   TTC GAT GTC TGG GGC GCA GGG ACC ACG GTC ACT GTC TCC TCA GCT AG 3'
   --- --- --- --- --- --- --- --- --- --- --- --- --- --- --- --
   Phe Asp Val Trp Gly Ala Gly Thr Thr Val Thr Val Ser Ser Ala
```

(SEQ ID NO:114)
(SEQ ID NO:115)

FIG. 29

29B12 Heavy Chain

```
                9              18              27              36              45              54
5'  ATG GAC TTT GGG CTC AGC TTG GTT TTC CTT GTC CTT GTT TTA AAA GGT GTC CAG
    --- --- --- --- --- --- --- --- --- --- --- --- --- --- --- --- --- ---
    Met Asp Phe Gly Leu Ser Leu Val Phe Leu Val Leu Val Leu Lys Gly Val Gln

                  63              72              81              90              99             108
    TGT | GAA GTG AAG CTG GTG GAG TCA GGG GGA GGC TCA GTG CAG CCT GGA GGG TCC
    --- | --- --- --- --- --- --- --- --- --- --- --- --- --- --- --- --- ---
    Cys | Glu Val Lys Leu Val Glu Ser Gly Gly Gly Ser Val Gln Pro Gly Gly Ser

               117             126             135             144             153             162
    CTG AAA CTC TCC TGT GCA ACC TCT GGA TTC ATT TTC AGT GAC TAT TAC ATG TAT
    --- --- --- --- --- --- --- --- --- --- --- --- --- --- --- --- --- ---
    Leu Lys Leu Ser Cys Ala Thr Ser Gly Phe Ile Phe Ser Asp Tyr Tyr Met Tyr

               171             180             189             198             207             216
    TGG GTT CGC CAG ACT CCA GAG AAG AGG CTG GAG TGG GTC GCA TAC ATT AGT ATT
    --- --- --- --- --- --- --- --- --- --- --- --- --- --- --- --- --- ---
    Trp Val Arg Gln Thr Pro Glu Lys Arg Leu Glu Trp Val Ala Tyr Ile Ser Ile

               225             234             243             252             261             270
    GGT AGT GGT AAT ACC TAT TAT CCA GAC ACT GTA AAG GGC CGA TTC ACC ATC TCC
    --- --- --- --- --- --- --- --- --- --- --- --- --- --- --- --- --- ---
    Gly Ser Gly Asn Thr Tyr Tyr Pro Asp Thr Val Lys Gly Arg Phe Thr Ile Ser

               279             288             297             306             315             324
    AGA GAC ATT GCC AAG AAC ACC CTG TAC CTG CAA ATG AGC CGT CTG AAG TCT GAG
    --- --- --- --- --- --- --- --- --- --- --- --- --- --- --- --- --- ---
    Arg Asp Ile Ala Lys Asn Thr Leu Tyr Leu Gln Met Ser Arg Leu Lys Ser Glu

               333             342             351             360             369             378
    GAC ACA GCC ATG TAT TAC TGT GTA AGG GGG AGA TTA CGA TTC CTT TTC GAC TAT
    --- --- --- --- --- --- --- --- --- --- --- --- --- --- --- --- --- ---
    Asp Thr Ala Met Tyr Tyr Cys Val Arg Gly Arg Leu Arg Phe Leu Phe Asp Tyr

               387             396             405             414             423
    GCT ATG GAC TAT TGG GGT CAA GGA ACC TCA GTC ACC GTC TCC TCA GCT AGC 3'
    --- --- --- --- --- --- --- --- --- --- --- --- --- --- --- --- ---
    Ala Met Asp Tyr Trp Gly Gln Gly Thr Ser Val Thr Val Ser Ser Ala Ser
```

(SEQ ID NO:116)
(SEQ ID NO:117)

FIG. 30

33G7 Heavy Chain

```
              15          24          33          42          51          60
5' ATG ATG GTG TTA AGT CTT CTG TAC CTG TTG ACA GCC ATT CCT GGT ATC CTG TCT
   --- --- --- --- --- --- --- --- --- --- --- --- --- --- --- --- --- ---
   Met Met Val Leu Ser Leu Leu Tyr Leu Leu Thr Ala Ile Pro Gly Ile Leu Ser

              69          78          87          96         105         114
   | GAT GTA CAG CTT CAG GAG TCA GGA CCT GAC CTC GTG AAA CCT TCT CAG TCT CTG
   | --- --- --- --- --- --- --- --- --- --- --- --- --- --- --- --- --- ---
   | Asp Val Gln Leu Gln Glu Ser Gly Pro Asp Leu Val Lys Pro Ser Gln Ser Leu

             123         132         141         150         159         168
   TCT CTC ACC TGC TCT GTC ACT GGC TAC TCC ATC ACC AGT GGT TAT TAC TGG AAC
   --- --- --- --- --- --- --- --- --- --- --- --- --- --- --- --- --- ---
   Ser Leu Thr Cys Ser Val Thr Gly Tyr Ser Ile Thr Ser Gly Tyr Tyr Trp Asn

             177         186         195         204         213         222
   TGG ATC CGG CAG TTT CCA GGA AAC AAA CTG GAA TGG GTG GGC TAC TTA AGC TAC
   --- --- --- --- --- --- --- --- --- --- --- --- --- --- --- --- --- ---
   Trp Ile Arg Gln Phe Pro Gly Asn Lys Leu Glu Trp Val Gly Tyr Leu Ser Tyr

             231         240         249         258         267         276
   GAC GGT AGC AAA AGC CAC AAC CCA TCT CTC AGA AAT CGA ATC TCC ATC ACT CGT
   --- --- --- --- --- --- --- --- --- --- --- --- --- --- --- --- --- ---
   Asp Gly Ser Lys Ser His Asn Pro Ser Leu Arg Asn Arg Ile Ser Ile Thr Arg

             285         294         303         312         321         330
   GAC CCA TCT AAG AAC CAG TTT TTC CTG AAG TTG AAT TCT GTG ACT ACT GAG GAC
   --- --- --- --- --- --- --- --- --- --- --- --- --- --- --- --- --- ---
   Asp Pro Ser Lys Asn Gln Phe Phe Leu Lys Leu Asn Ser Val Thr Thr Glu Asp

             339         348         357         366         375         384
   ACA GCT ACA TAT TAC TGT GCA AGA GGG GGA AAG ATT TTT TAC GGT AGT AGC TAC
   --- --- --- --- --- --- --- --- --- --- --- --- --- --- --- --- --- ---
   Thr Ala Thr Tyr Tyr Cys Ala Arg Gly Gly Lys Ile Phe Tyr Gly Ser Ser Tyr

             393         402         411         420         429         438
   GAC CCG TTT GCT TAC TGG GGC CAA GGG ACT CTG GTC ACC GTC TCC TCA GCT AGC 3'
   --- --- --- --- --- --- --- --- --- --- --- --- --- --- --- --- --- ---
   Asp Pro Phe Ala Tyr Trp Gly Gln Gly Thr Leu Val Thr Val Ser Ser Ala Ser
```

(SEQ ID NO:118)
(SEQ ID NO:119)

METHOD FOR PREPARING ANTI-MIF ANTIBODIES

CROSS REFERENCE TO RELATED APPLICATIONS

This is a divisional of U.S. patent application Ser. No. 09/791,551, filed Feb. 26, 2001, now abandoned which claims priority to U.S. Provisional Patent Application No. 60/185,390, filed Feb. 28, 2000, and U.S. Provisional Patent Application No. 60/233,625, filed Sep. 18, 2000, the entirety of which are being incorporated herein in their entirety

FIELD OF THE INVENTION

The invention relates to a method of making high-affinity anti-macrophage migration inhibitory factor (MIF) antibodies in animals which are homozygously deficient of a MIF gene ($MIF^{-/-}$). The invention further relates to high affinity anti-MIF antibodies, compositions comprising said antibodies and methods of treating diseases using said anti-MIF antibodies.

BACKGROUND OF THE INVENTION

Migration Inhibitory Factor

Macrophage migration inhibitor factor (MIF) was one of the first identified lymphokines [Bloom et al., *Science* 153: 80-82 (1966)] and is a pleiotropic cytokine released by macrophages, T-cells and the pituitary gland during inflammatory responses. It acts as a pro-inflammatory cytokine, playing a major role in endotoxin shock and counter-regulating the anti-inflammatory effects of dexamethasone [Bozza et al., *J. Exp. Med.* 189: 341-6 (1999)]. MIF promotes tumor necrosis factor alpha (TNF∀) synthesis, T-cell activation [Leech et al., *Arthritis Rheum.* 42: 1601-8 (1999)], enhances interleukin-1 (IL-1) and interferon gamma (IFN( ) production [Todo, *Mol. Med.* 4: 707-14 (1998)], impacts macrophage-macrophage adherence, upregulates HLA-DR, increases nitric oxide synthase and nitric oxide concentrations, and inhibits *Mycoplasma avium* growth (U.S. Pat. No. 5,681,724). Certain of these features indicate that MIF also plays a role in the pathogenesis of rheumatoid arthritis (RA) (Id.). MIF is implicated in the activation of macrophages and counter-regulation of glucocorticoid activity [Chesney et al., *Mol. Med.* 5: 181-91 (1999)]. Recombinant forms of MIF and the DNAs encoding them have been previously described, see for example (WO 90/11301). MIF also has a reported role in the innate host response to staphylococcal and streptococcal exotoxins (Calandra et al., *Proc. Natl. Acad. Sci. USA* 95: 11383-8 (1998)).

MIF inhibition has been suggested for the treatment of acute lung injury to suppress the level of neutrophil attraction to the site of injury (Makita et al., *Am J. Respir. Crit. Care Med.* 158: 573-9 (1998)). MIF localizes to the cytoplasm of leukemic cells and has been linked to a role in leukemia associated inflammatory events (Nishihira et al., *Biochem. Mol. Biol. Int.* 40: 861-9 (1996)).

Several forms of MIF have been identified. The first characterized was that of Weiser et al., *Proc. Natl. Acad. Sci. USA* 86: 7522-6 (1989). This MIF (MIF-1) is 115 amino acids and 12.5 kDa (Id.). MIF-2 is a 45 kD protein identified in a human T-cell hybridoma clone (F5) (Hirose et al., *Microbiol. Immunol.* 35: 235-45 (1991)). The sequence of MIF-2 is very similar to MIF-1, but differs in that it is a more hydrophilic species than MIF-2 (Oki et al., *Lymphokine Cytokine Res.* 10: 273-80 (1991)).

MIF-3 is an 119 amino acid residue sequence (ATCC No. 75712; WO 95/31468). Antibodies and antagonists have been developed to MIF-3, which can be used to protect against lethal endotoxemia and septic shock or to treat ocular inflammations (WO 95/31468).

A related protein to MIF is the glycosylation-inhibiting factor (GIF), (Galat et al., *Eur. J. Biochem.* 224: 417-21 (1994)). The cDNA expressing the human form of GIF is described by Mikayama et al., *Proc. Natl. Acad. Sci. U.S.A.* 90: 10056-60 (1993). The amino acid sequences for MIF-1 and GIF are now recognized to be identical. The correct amino acid sequence is 114 amino acids and forms a 12,345 Da protein (Swiss-Protein accession number P14174).

Anti-MIF Antibodies

Polyclonal and monoclonal anti-human MIF antibodies have been developed against recombinant human MIF (Shimizu et al., *FEBS Lett* 381: 199-202 (1996); Japanese Patent No. 9077799A; German Democratic Republic Patent No. 230876A; European Patent No. 162812; and ATCC Accession Nos. 00201X0003, 1024674 and 1014477). One monoclonal antibody against human MIF (IC5/B) has been developed and utilized to study signals to mononuclear phagocytes in pseudolymphomas and sarcoidosis [Gomez et al., *Arch. Dermatol. Res.* (*Germany*) 282: 374-8 (1990); see also Weiser et al., *Cell. Immunol.* 90: 167-78 (1985)]. Additional human monoclonal anti-MIF antibodies were developed by Kawaguchi et al., *J. Leukoc. Biol.* 39: 223-232 (1986) and Weiser et al., *Cell. Immunol.* 90: 167-78 (1985). Anti-murine MIF monoclonal antibodies have also been prepared [See, e.g., Malomy et al., *Clin. Exp. Immunol.* 71: 164-70 (1988); and Liu et al., *J. Immunol.* 137: 448-55 (1986)].

Anti-MIF antibodies have been suggested for therapeutic use to inhibit TNF∀ release (Leech et al., 1999). As such, anti-MIF antibodies may have wide therapeutic applications for the treatment of inflammatory diseases. Related thereto, the administration of anti-MIF antibodies also reportedly inhibited adjuvant arthritis in rats (Leech et al., *Arthritis Rheum.* 41: 910-7 (1998)).

MIF has also been implicated in the pathogenesis of immunologically induced kidney disease. Lan et al., *J. Exp. Med.* 185: 1455-65 (1997) proposed the use of agents which block MIF activity to treat rapidly progressive glomerulonephritis in patients, and also suggested that MIF may be important in immune-mediated diseases generally.

Calandra et al., *I. Inflamm.* 47: 39-51 (1995) reportedly used anti-MIF antibodies to protect animals from experimentally induced gram-negative and gram-positive septic shock. Anti-MIF antibodies were suggested as a means of therapy to modulate cytokine production in septic shock and other inflammatory disease states (Id.).

Anti-MIF antibodies have been proposed for use to treat diseases where cellular/mucosal immunity should be stimulated or as a diagnostic or prognostic marker in pathological conditions involving the production of MIF (WO 96/09389).

MIF antagonists have been proposed to treat lymphomas and solid tumors which require neovascularization (WO 98/17314). WO 98/17314 by Bucala et al. reportedly describes inhibition of murine B cell lymphoma growth in vivo by a neutralizing monoclonal antibody against MIF administered at the time of tumor implantation (Chesney et al., 1999). Previous studies have shown that TH2 lymphocytes produce higher amounts of MIF upon stimulation than TH1 cells. (Bacher et al, 1996. PNAS 93:7849.) Since MIF is functionally involved in T-cell activation, neutralization of TH2 cell-derived may promote the ratio of TH1 to TH2 cells, thereby also prevent influencing host immunity against tumors (Chesney, 1999). Also, the use of anti-MIF antibodies for inhibiting proliferation of human endothelial cells has been reported [Chesney et al., *Mol. Med.* 5: 181-91 (1999); and Ogawa et al., *Cytokine* 12:309-314 (2000)]. Specifically, Ogawa et al. (2000) showed that certain anti-MIF antibodies directly block VEGF stimulated endothelial cell growth, presumably through neutralization of endogenously produced MIF.

Knock-out Animals for Use in Preparing Antibodies to Self-antigens

Transgenic animals have been prepared wherein foreign antigens are now expressed in the transgenic animal as a self-antigen. For example, a virus protein was expressed in a transgenic mouse model as a self-antigen in the pancreatic islets of Langerhans, as described by Oldstone et al., *Cell* 65: 319-31 (1991). Typically, however, it is difficult to produce antibodies against self-antigens or autoantigens such as MIF. Autoantigens are normal constituents of the body, which remain typically are not recognized by the immune system.

A knock-out (KO) mouse or animal is one in which the animal is homozygously deficient of a functional gene (Declerck et al., *J. Biol. Chem.* 270: 8397-8400 (1995)). In general, antibodies will not be raised against self-antigens nor against highly conserved domains of proteins that do not vary between species. However, certain KO mice have been produced in which monoclonal auto-antibodies against various autoantigens have been raised. Castrop et al., *Immunobiol.* 193: 281-7 (1995) reported preparation of the use of a KO mouse for the generation of monoclonal antibodies to T-cell factor-1 (TCF-1), which had been historically difficult to prepare antibodies to due to the extreme evolutionary conservation of TCF-1. Reportedly, because TCF-1 is highly expressed in thymus, intrathymic selection mechanisms will impose tolerance for TCF-1 in the immune system, likely through clonal deletion of TCF-1-reactive T-cells (Id.). The anti-TCF-1 antibodies were raised against a fusion protein comprising TCF-1 fused to maltose binding protein (MBP).

LaTemple et al., *Xenotransplantation* 5: 191-6 (1998) used a KO mouse to ∀1,3galactosyltransferase (∀1,3GT KO) to produce a natural, anti-Gal antibody. However, the antibody was only produced in low amounts.

Declerck et al. (1995) reported the preparation of anti-murine tissue-type plasminogen activator (t-PA) in a KO mouse, wherein the mouse lacked a functional t-PA gene. Declerck et al., also suggested that this approach could be applied to other classes of proteins allowing the generation of monoclonal antibodies against conserved epitopes, which could not be raised in wild-type animals because of their "self-antigen" nature. See also Declerck et al., *Thromb. Haemost* (*Germany*) 74: 1305-9 (1995).

To better study the biologic role of MIF, a mouse strain lacking MIF was generated by gene targeting in embryonic stem cells (Bozza et al., 1999). Using this mouse model, Bozza et al. determined that MIF is involved in a host response to gram negative bacteria induced sepsis.

Therefore, not withstanding what has been previously reported in the literature, there exists a need for preparing anti-MIF antibodies, especially monoclonal antibodies and fragments thereof with improved affinity and avidity for purposes of studying MIF function as well as regulating MIF activity. The methods of preparing the antibodies of this invention, as well as the antibodies themselves, can in turn be used to modulate MIF activity in diseases and conditions mediated by MIF, such as sepsis, rheumatoid arthritis, other autoimmune diseases, cancer, as well as injuries which induce MIF production.

SUMMARY OF THE INVENTION

It is an object of the invention to provide novel and improved methods for producing high-affinity anti-MIF antibodies in animals which are homozygous deficient for a MIF gene ($MIF^{-/-}$). The gene can be MIF-1, MIF-2, MIF-3 or a MIF-like gene, but preferably is the MIF described by Weiser et al., (1989). A preferred method for preparing high affinity anti-MIF antibody or immunogenic fragment thereof comprises the steps of: (A) preparing a transgenic animal in which the MIF gene is functionally knocked out; (B) immunizing said transgenic animal with MIF or an immunogenic polypeptide fragment thereof; and (C) obtaining anti-MIF antibodies from said animal.

It is a more specific object of the invention to provide a novel method of preparing high-affinity anti-MIF antibody fragments, such as Fv, Fab, $F(ab')_2$, Fab' and scFV.

Another object of the invention is to provide for a method of obtaining cells which produce high-affinity anti-MIF antibodies from a MIF knock-out animal for purposes of preparing anti-MIF antibody producing cell lines or cell lines which produce recombinant forms of anti-MIF antibody fragments.

Another object of the invention is to provide a novel nucleic acid encoding a MIF gene targeting construct comprising (A) a selectable marker and (B) DNA sequence homologous to a MIF gene or portion thereof, wherein said isolated nucleic acid is introduced into an animal at an embryonic stage, and wherein said nucleic acid disrupts endogenous MIF gene activity wherein MIF protein production is prevented and wherein the animal, which is a homozygous MIF deficient mutant, is a suitable bioreactor for production of high affinity anti-MIF antibodies.

It is a further object of the invention to provide a transgenic animal genome comprising a homozygous disruption of the endogenous MIF gene, wherein said disruption comprises the insertion of a selectable marker sequence, and wherein said disruption results in said animal, which lacks an endogenous MIF as compared to a wild type animal and wherein said animal is a bioreactor for anti-MIF antibodies possessing high affinity.

Another object of the invention is to provide a method for producing a transgenic animal lacking endogenous MIF, said method comprising the steps of: (A) introducing a MIF targeting construct comprising a selectable marker sequence into a embryonic stem cell; (B) introducing said animal embryonic stem cell into a animal embryo; (C) transplanting said embryo into a pseudopregnant animal; (D) allowing said embryo to develop to term; and (B) identifying a transgenic animal whose genome comprises a disruption of the endogenous MIF gene at least one allele; (F) breeding the transgenic animal of step E to obtain a transgenic animal whose genome comprises a homozygous disruption of the endogenous MIF gene ($MIF^{-/-}$), wherein said disruptions results in an animal which lacks at least one endogenous MIF as compared to a wild type animal.

BRIEF DESCRIPTION OF THE DRAWING FIGURES

Figure 4:
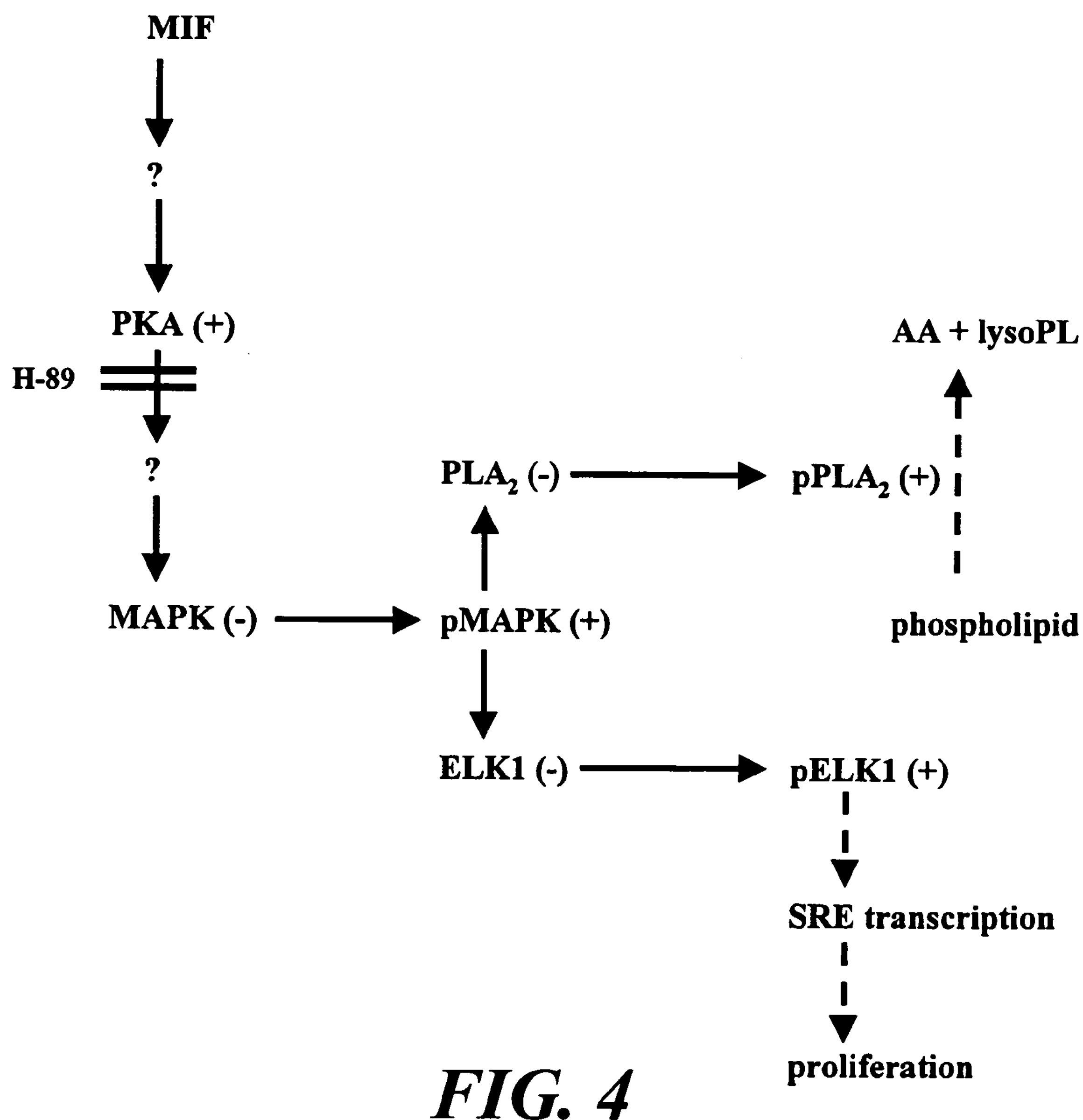

FIG. 4 shows the MIF mediated signaling events that occur in the protein kinase A (PKA) and MAP kinase (MAPK) signaling cascade, as described by Mitchell et al., *J. Biol. Chem.* 274: 18100-6 (1999).

Figure 5:
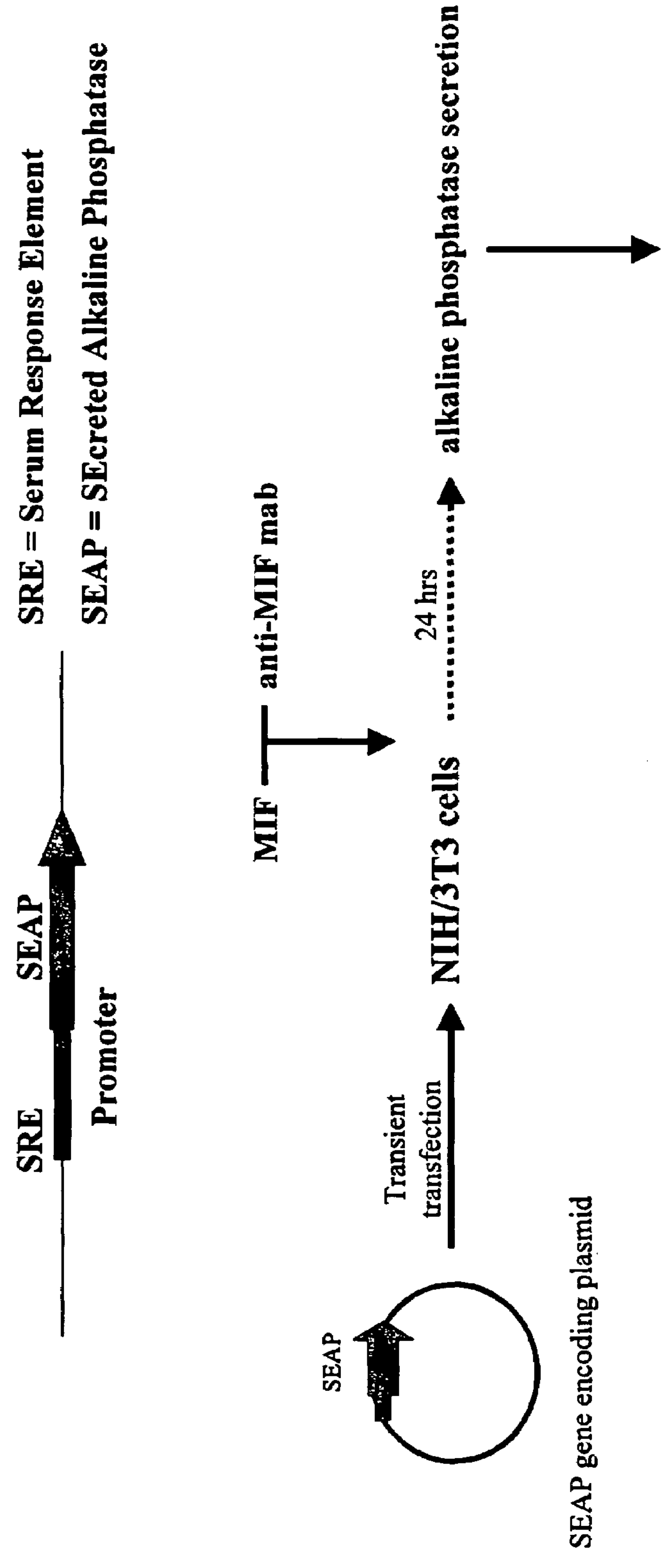

FIG. 5 depicts the transcription-based assay for determining anti-MIF antibody neutralization activity using the SRE-SEAP transcription and secretion assay.

Figure 6:
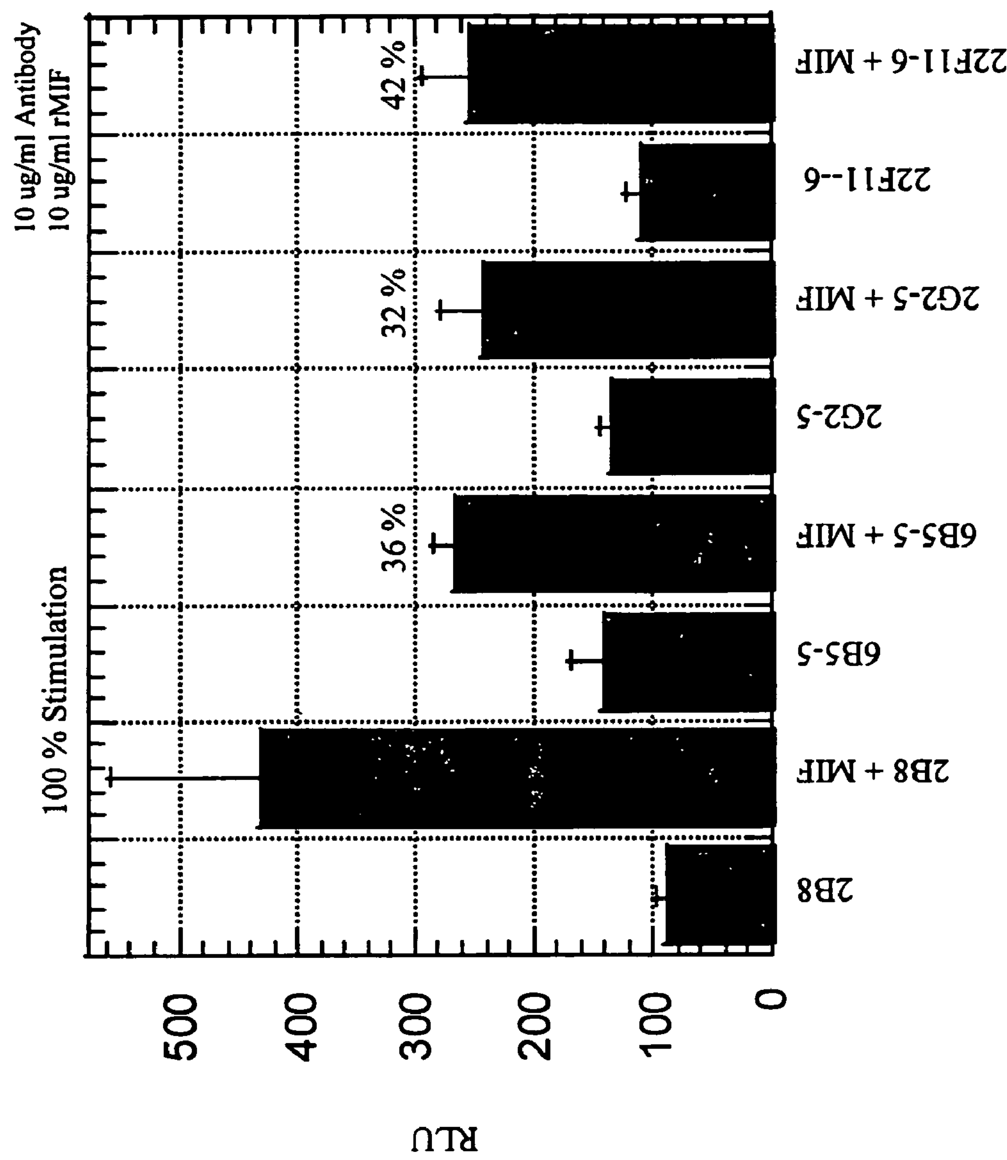

FIG. 6 shows the percent inhibition of induced by anti-MIF antibodies on MIF induced SRE-SEAP transcription and secretion 10: g/ml antibody and 10: g/ml rMIF were used in each reaction.

Figure 7:
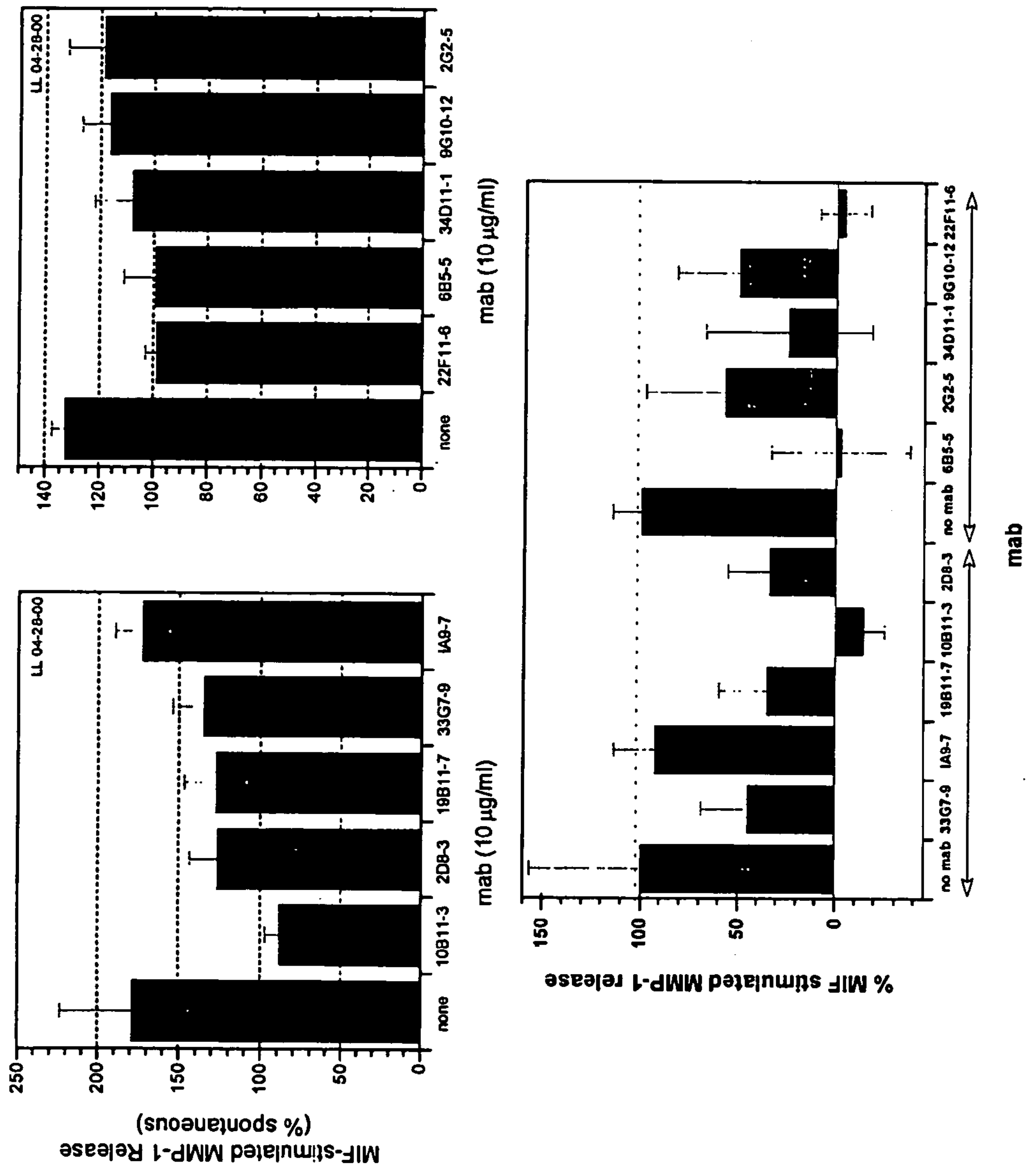

FIG. 7 shows the anti-MIF Mab effects on MIF stimulated MMP-1 release from dermal fibroblasts.

Figure 8:
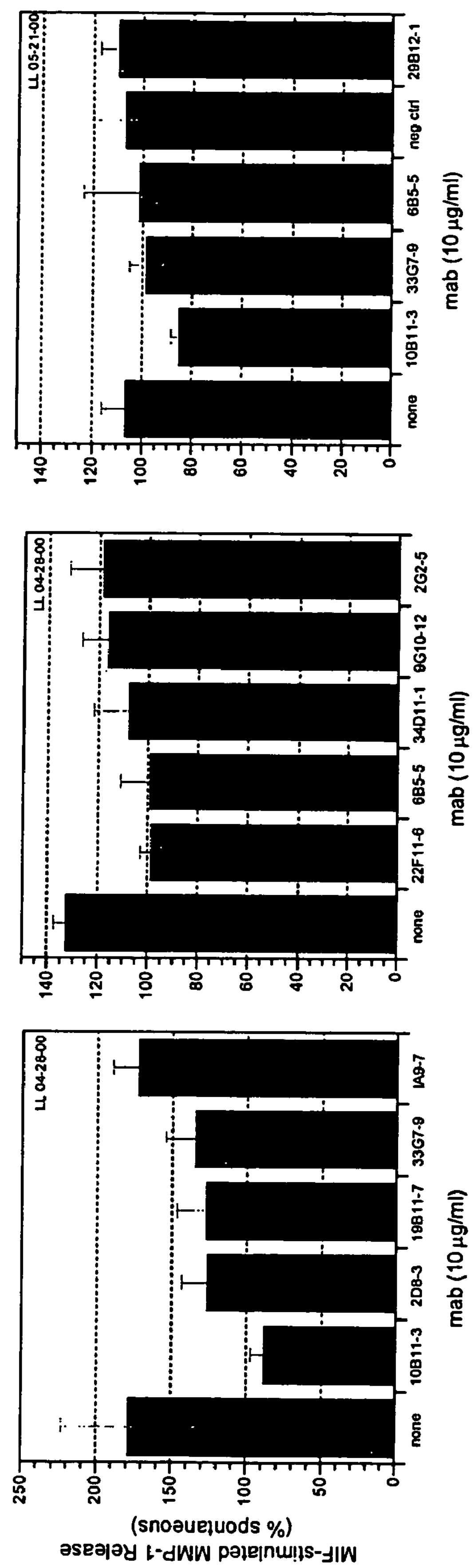

FIG. 8 shows the anti-MIF Mab effects on VEGF-stimulated proliferation of human umbilical vein endothelial (HUVE) cells.

Figure 9:
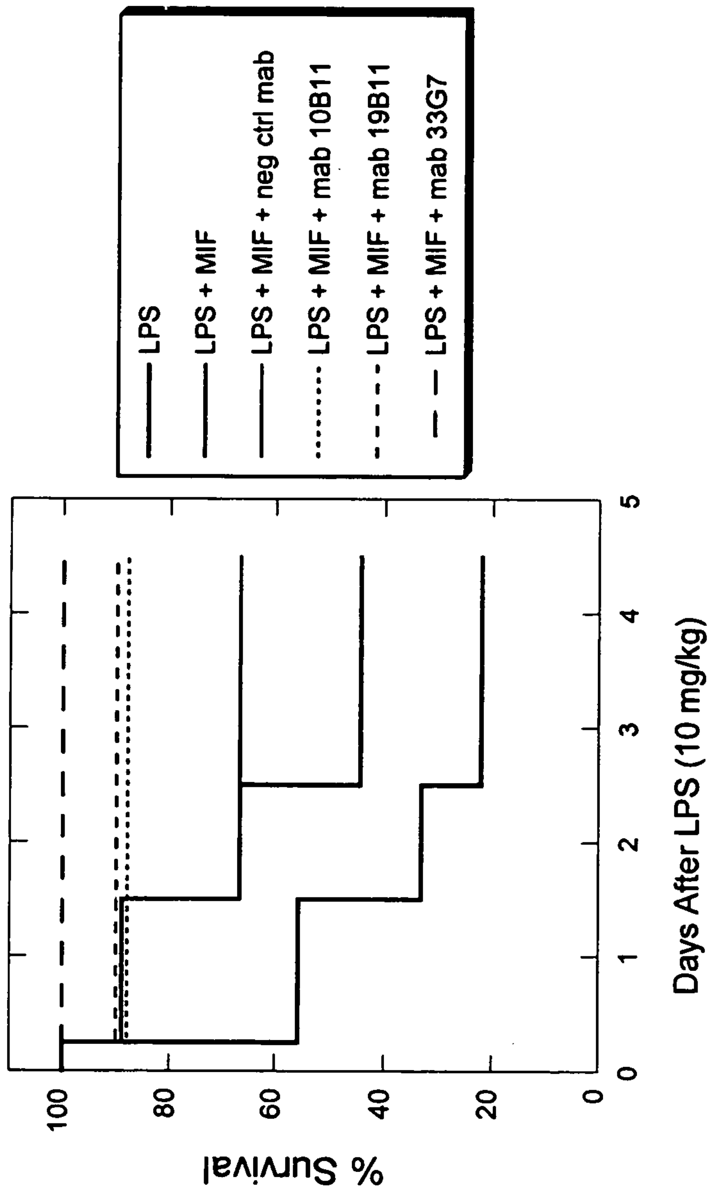

FIG. 9 shows anti-MIF Mab effects on MIF+LPS induced lethality in BALB/c mice when 10 mg LPS/kg body weight is administered per mouse.

Figure 10:
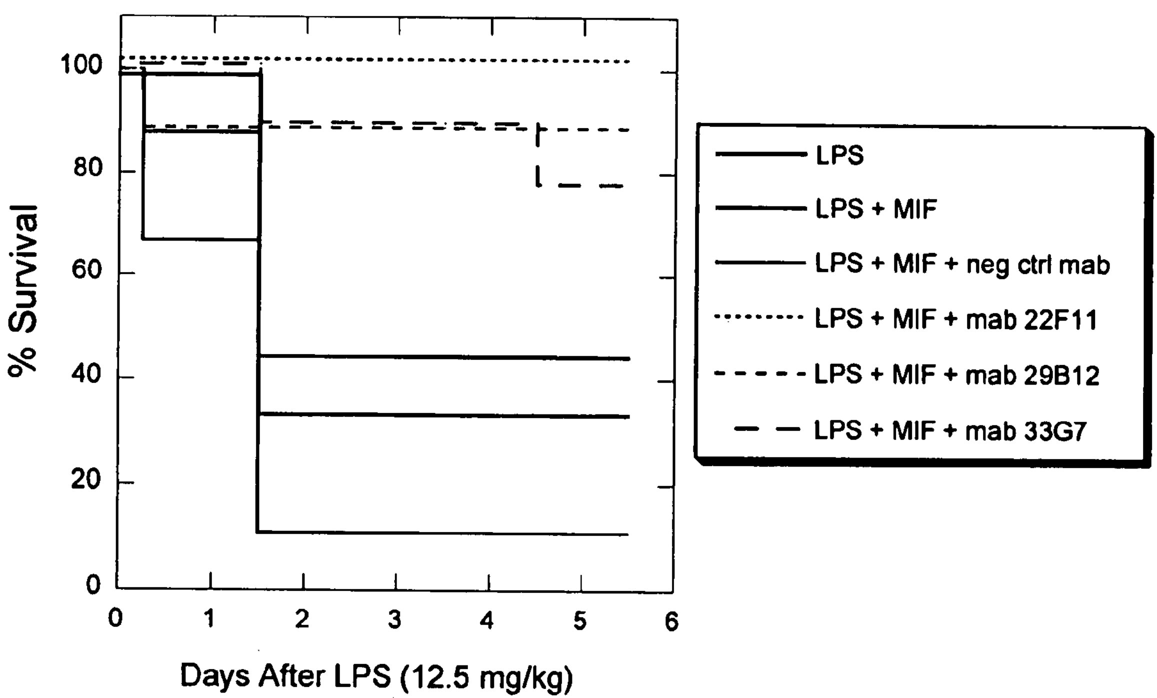

FIG. 10 shows anti-MIF Mab effects on MIF+LPS induced lethality in BALB/c mice when 12.5 mg LPS/kg body weight is administered per mouse.

Figure 11:
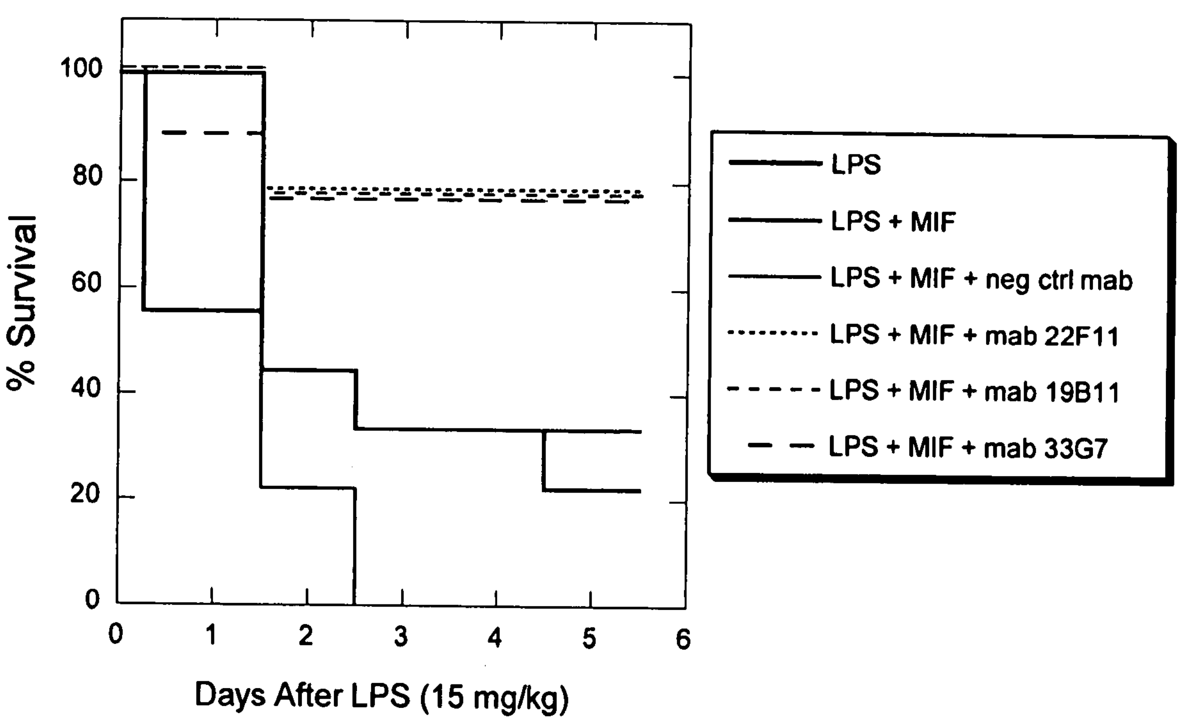

FIG. 11 shows anti-MIF Mab effects on MIF+LPS induced lethality in BALB/c mice when 15 mg LPS/kg body weight is administered per mouse.

Figure 12A:
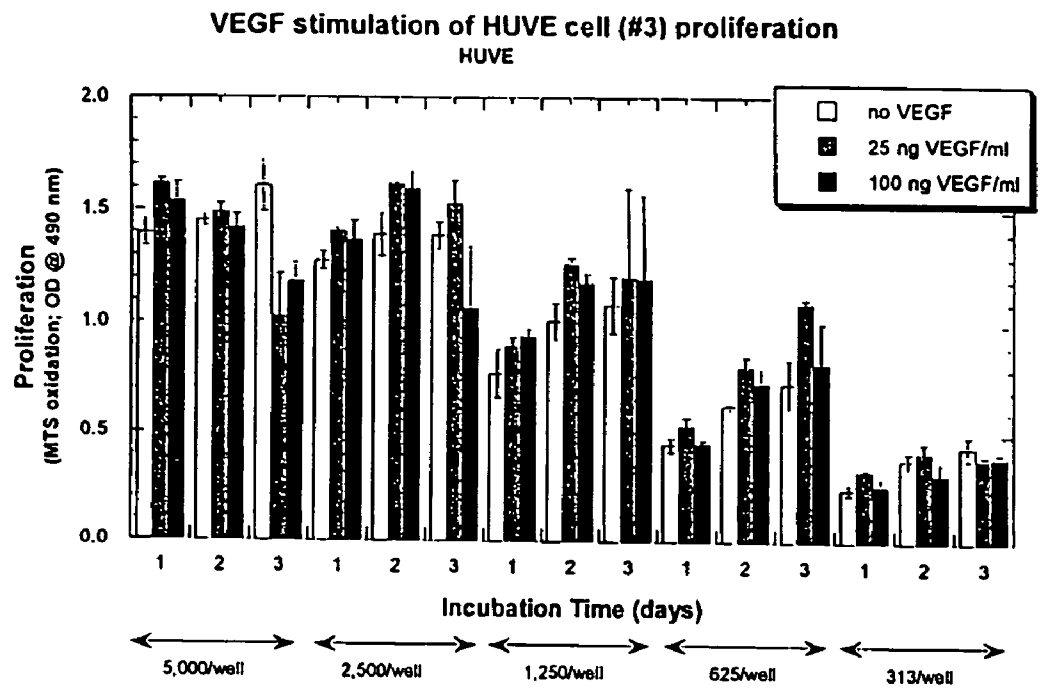
Figure 12B:
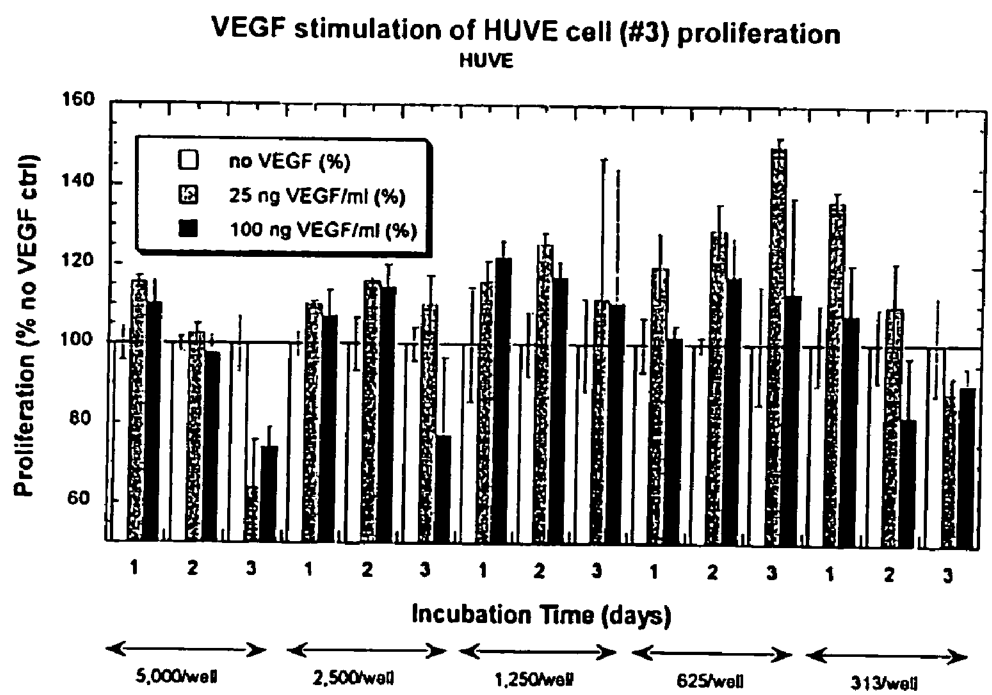

FIGS. 12A and 12B show the results of an assay that measured the effect of VEGF stimulation of HUVE cell proliferation over time in the absence of VEGF or at concentrations of 25 ng or 100 ng of VEGF over time.

Figure 13:
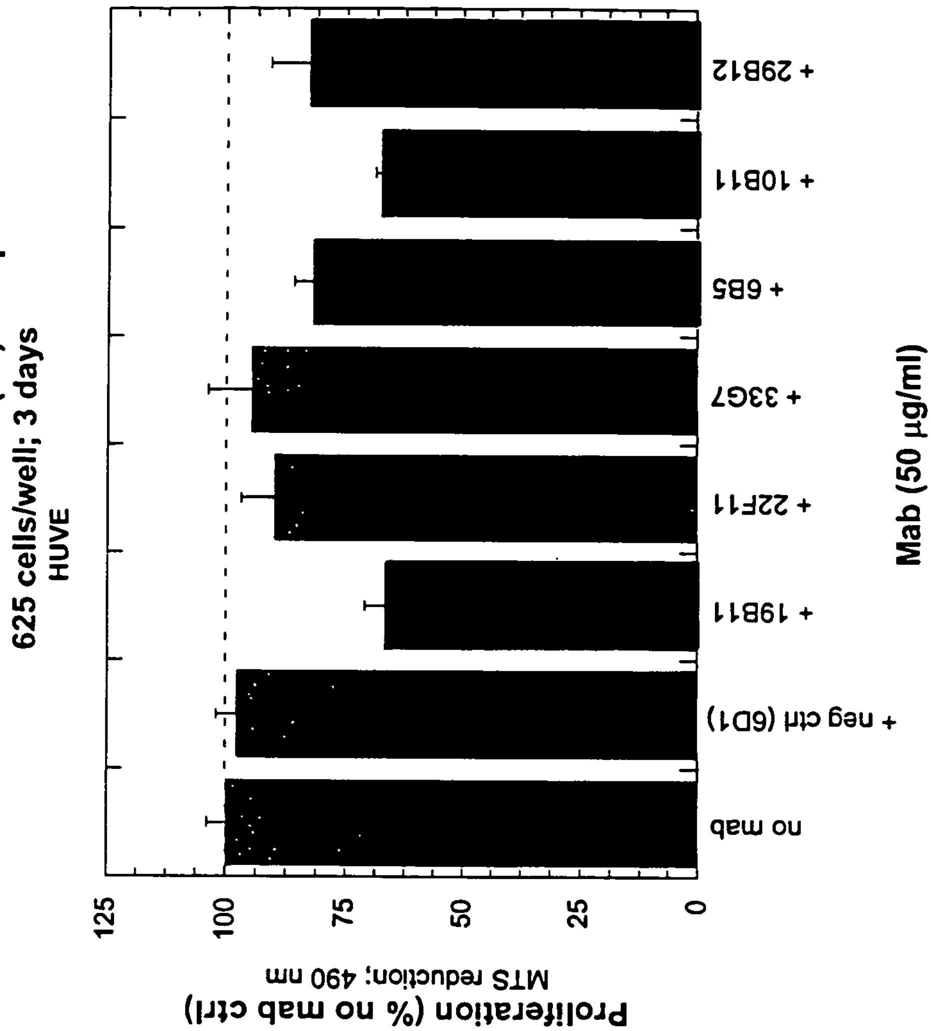

FIG. 13 shows the results of an assay that evaluated effect of anti-MIF antibody on HOVE cells proliferation (various antibodies tested) at a concentration of 50 mg/ml in wells containing 625 cells/well after three (3) days.

Figure 14:
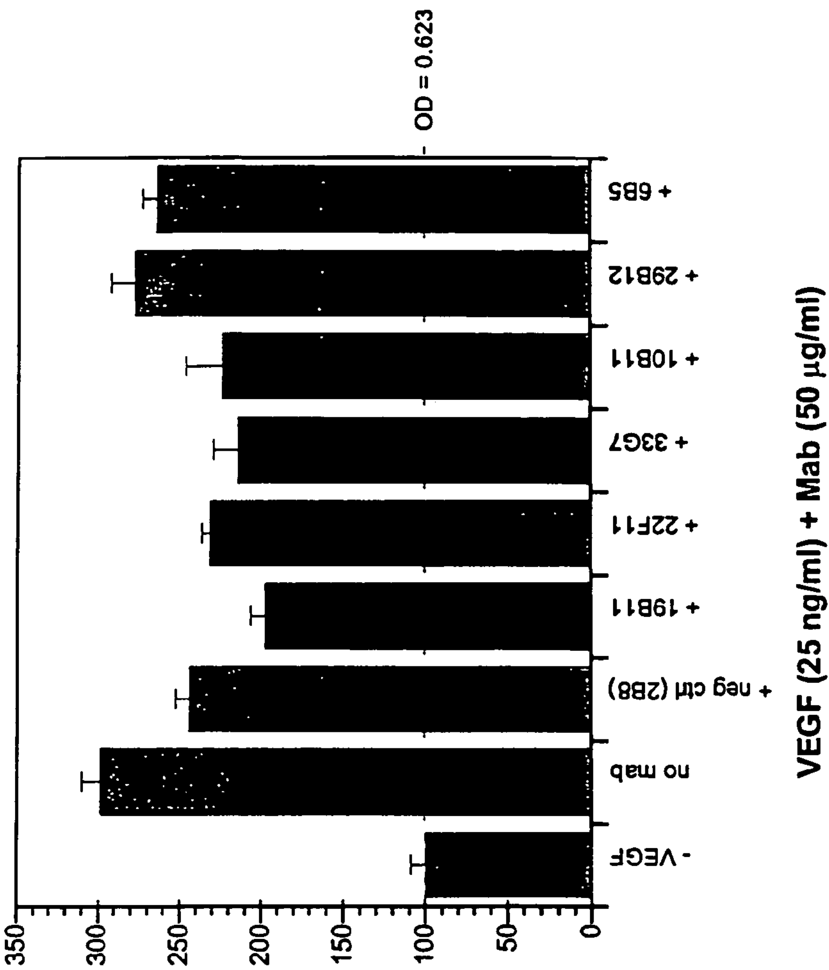

FIG. 14 shows the results of an assay that, similar to the assay shown in FIG. 13, compares the effect of different anti-MIF antibodies at a concentration of 50 mg/ml on HUVE cell proliferation in microwells containing 2500 cells/well after five (5) days.

Figure 15:
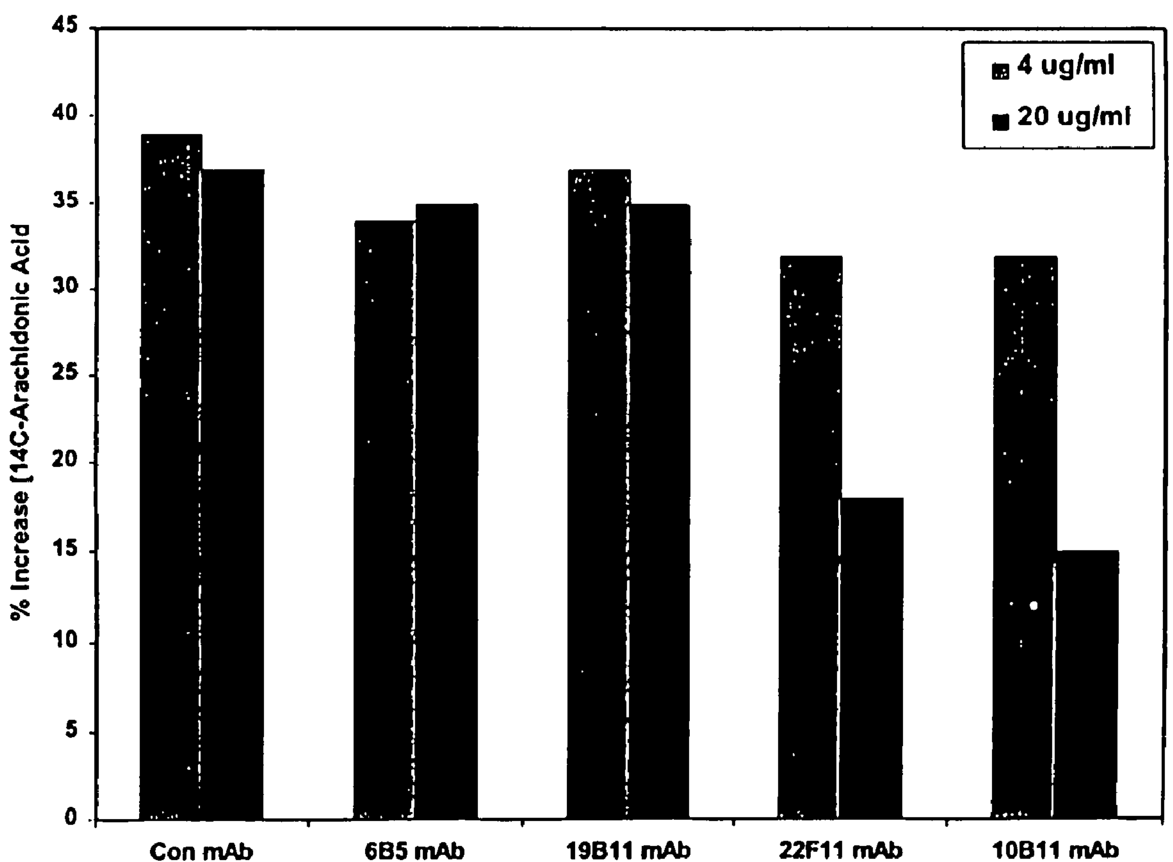

FIG. 15 shows the results of an assay that compares the effect of different anti-MIF antibodies on MIF-enhanced archidonic acid release in RAW264.7 cells transfected with the MIF gene (at antibody concentrations of 4 mg/ml and 20 mg/ml).

Figure 16:
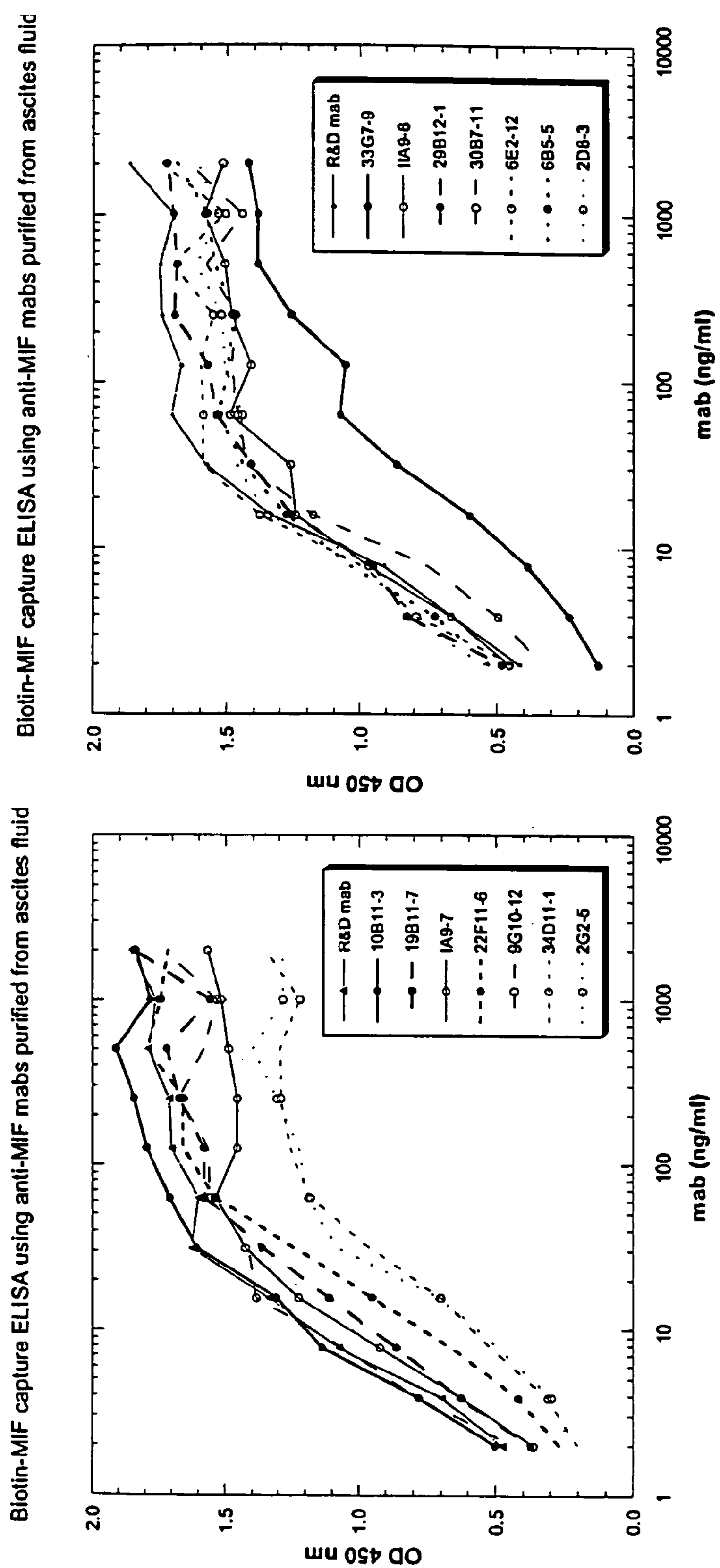

FIG. 16 contains an assay that compares binding of two lead candidate anti-MIF mabs, which were immobilized, particularly with respect to the capture of biotin-human MIF at different antibody concentrations.

FIG. 17 contains the amino acid sequences of the light chains of lead anti-MIF antibodies 6B5, 10B11, 19B11, 22F11, 29B12, and 33G7 (SEQ ID NOs: 1-48).

FIG. 18 contains the amino acid sequence of the light chain of anti-MIF antibody 6B5 and a DNA nucleotide sequence that encodes the 6B5 light chain polypeptide (SEQ ID NOs: 49 and 50).

FIG. 19 contains the amino acid sequence of the light chain of anti-MIF antibody 10B11 and a DNA nucleotide sequence that encodes the 10B11 light chain polypeptide (SEQ ID NOs: 51 and 52).

FIG. 20 contains the amino acid sequence of the light chain of anti-MIF antibody 19B11 and a DNA nucleotide sequence that encodes the 19B11 light chain polypeptide (SEQ ID NOs: 53 and 54).

FIG. 21 contains the amino acid sequence of the light chain of anti-MIF antibody 22F11 and a DNA nucleotide sequence that encodes the 22F11 light chain polypeptide (SEQ ID NOs: 55 and 56).

FIG. 22 contains the amino acid sequence of the light chain of anti-MIF antibody 29B12 and a DNA nucleotide sequence that encodes the 29B12 light chain polypeptide (SEQ ID NOs: 57 and 58).

FIG. 23 contains the amino acid sequence of the light chain of anti-MIF antibody 33G7 and a DNA nucleotide sequence that encodes the 33G7 light chain polypeptide (SEQ ID NOs: 59 and 60).

FIG. 24 contains the amino acid sequences of the heavy chains of lead anti-MIF antibodies 6B5, 10B11, 19B11, 22F11, 29B12, and 33G7 (SEQ ID NOs: 61-107).

FIG. 25 contains the amino acid sequence of the heavy chain of anti-MIF antibody 6B5 and a DNA nucleotide sequence that encodes the 6B5 heavy chain polypeptide (SEQ ID NOs: 108 and 109).

FIG. 26 contains the amino acid sequence of the heavy chain of anti-MIF antibody 10B11 and a DNA nucleotide sequence that encodes the 10B11 heavy chain polypeptide (SEQ ID NOs: 110 and 111).

FIG. 27 contains the amino acid sequence of the heavy chain of anti-MIF antibody 19B11 and a DNA nucleotide sequence that encodes the 19B11 heavy chain polypeptide (SEQ ID NOs: 112 and 113).

FIG. 28 contains the amino acid sequence of the heavy chain of anti-MIF antibody 22F11 and a DNA nucleotide sequence that encodes the 22F11 heavy chain polypeptide (SEQ ID NOs: 114 and 115).

FIG. 29 contains the amino acid sequence of the heavy chain of anti-MIF antibody 29B12 and a DNA nucleotide sequence that encodes the 29B12 heavy chain polypeptide (SEQ ID NOs: 116 and 117).

FIG. 30 contains the amino acid sequence of the heavy chain of anti-MIF antibody 33G7 and a DNA nucleotide sequence that encodes the 33G7 heavy chain polypeptide (SEQ ID NOs: 118 and 119).

DETAILED DESCRIPTION OF THE INVENTION

A. Definitions

By "MIF" or "macrophage migration inhibitory factor" is meant the protein or nucleic acid encoding the protein which is responsible for attracting macrophages to a site. A preferred MIF is mammalian MIF, with most preferred being a human MIF. "MIF" also includes GIF (glycosylation-inhibiting factor), MIF-1, MIF-2, MIF-3, MIF-like proteins, and fragments of the MIF or MIF-like proteins. Additional forms of MIF encompassed by the term include those listed in Table 1, and as described in Weiser et al., (1989) and U.S. patent application Ser. Nos. 08/243,342; 08/462,350; 08/462,350 and 08/602,929; in PCT applications WO 96/09384; WO 90/11301; WO 94/26923; WO 95/31468 (to MIF-3); and in U.S. Pat. Nos. 5,328,990; 5,350,687; 4,299,814; 4,708,937 and European Patent No. 263072 (to macrophage inhibitory related peptides 8 and 14). The "MIF" proteins can also be in the form of a fusion protein.

By "knock-out animal," "KO animal," and "transgenic animal" is meant an animal in which a MIF gene has been functionally disrupted or inactivated. This inactivation refers to a modification of the gene in a manner which decreases or prevents expression of that gene and/or its product in a cell. The expression of the gene's product is completely suppressed. A functionally disrupted gene includes a modified gene which expresses a truncated polypeptide having less than the entire coding sequence of the wild-type gene.

By "animal" is meant to include preferably such mammals as primates, bovines, canines, felines, oviries, porcines, and rodents, etc. Preferable rodents include mice, hamsters, rabbits and guinea pigs. However, animals can include any eukaryote.

By "antibody" is intended to refer broadly to any immunologic binding agent, such as IgG (including $IgG_1$, $IgG_2$, $IgG_3$, and $IgG_4$), 1gM, IgA, IgD, 1gE, as well as antibody fragments. As used herein, "isotype" refers to the antibody class (e.g., IgM or $IgG_1$) that is encoded by heavy chain constant region genes. As used herein, "isotype switching" refers to the phenomenon by which the class, or isotype, of an antibody changes from one immunoglobulin (Ig) class to one of the other Ig classes. Antibodies in the broadest sense covers intact monoclonal antibodies, polyclonal antibodies, as well as biologically active fragments of such antibodies and altered antibodies.

By "monoclonal antibody" is meant an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256: 495-7 (1975), or may be made by recombinant DNA methods (see, e.g., U.S. Pat. No. 4.816,567). The "monoclonal antibodies" may also be isolated from phage antibody libraries using the techniques described for example in Clackson et al., *Nature* 352: 624-8 (1991) and Marks et al. *J. Mol. Biol.,* 222: 581-97 (1991).

The monoclonal antibodies herein specifically include "chimeric" antibodies (immunoglobulins) in which a portion of the heavy and/or light chain is identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired therapeutic activity, e.g., high affinity recognition of a MIF protein (U.S. Pat. No. 4,816,567; Morrison et al., *Proc. Natl. Acad. Sci. USA,* 81: 6851-5 (1984)).

"Humanized" forms of non-human (e.g., murine) antibodies are chimeric immunoglobulins, immunoglobulin chains or fragments thereof (such as Fv, Fab, Fab', $F(ab')_2$ or other antigen-binding subsequences of antibodies), which contain minimal sequence derived from a non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat, rabbit or other mammal having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc). For further details, see Jones et al., *Nature* 321: 522-5 (1986); Reichmann et al., *Nature* 332: 323-9 (1988); and Presta *Curr. Op. Struct. Biol.* 2: 593-6 (1992).

By "antibody fragment" or "immunogenic fragment" is meant an immunoglobulin, including segments of proteolytically-cleaved or recombinantly-prepared portions of an antibody molecule that are capable of selectively reacting with a particular antigen or antigen family (e.g., MIF). Nonlimiting examples of such proteolytic and/or recombinant fragments include "Fab", "$F(ab')_2$", and "Fab", "scFv" and "Fv" fragments. Recombinant techniques for producing Fv fragments are set forth in WO 88/0 1649, WO 88/-06630, WO 88/07085, WO 88/07086, and WO 88/09344. By a "$V_H$" fragment is meant that the variable region has at least a portion of a heavy chain variable region capable of being used as an antigen binding functionality. The preparation and use of a light chain variable region (VL) as an antigen binding functionality is set forth in an article by Williams et al., *Proc. Natl. A cad. Sci.* (*USA*) 86: 5537-41 (1989).

By "high-affinity antibody" is meant an antibody which binds to a MIF or GIF epitope with an affinity lower than $10^{-8}$ M (e.g., $10^{-9}$M, $10^{-10}$ M, etc.). These antibodies should be capable of recognizing the native MIF or GIF epitopes, unlike MIF antibodies 15.5 and 3D9, which recognize primarily denatured MIF with only weak recognition of native, undenatured MIF. Available antibodies against MIF include XIV 15.5 and 3D9. These all exhibit affinities less than $10^{-6}$M against native, soluble MIF protein. As a result, the in vivo biological potency is weak and is achieved at 20-30 mg/kg of antibody, which is too high for medical usage. Accordingly, the anti-MIF or anti-GIF antibodies produced by the knock-out animal will preferably yield a therapeutic response in a human when administered at dosages of about to about 15 mg/kg or less.

By "nucleic acid" is meant to include DNA, genomic DNA, RNA, mRNA and cDNA. The preferred nucleic acids of the invention include those that encode immunoglobulins or fragments thereof which recognize MIF. The term also may encompass a MIF targeting construct for the purpose of making a $MIF^{-/-}$ mouse.

By "gene" is meant the segment of DNA involved in producing a polypeptide chain. It includes regions preceding and following the coding region, as well as intervening sequences (e.g., introns) between the coding sequences (exons).

By "homologous recombination" is meant the process by which a nucleic acid molecule with similar genetic information aligns itself with a second nucleic acid molecule and exchanges nucleotide strands. A nucleotide sequence of the recombinant nucleic acid which is effective to achieve homologous recombination at a predefined position of a target nucleic acid therefore indicates a nucleotide sequence which facilitates the exchange of nucleotides strands between the recombinant nucleic acid molecule at a defined position of a target gene. The effective nucleotide sequence generally comprises a nucleotide sequence which is complementary to a desired target nucleic acid molecule (e.g., the gene locus to be modified), thus promoting nucleotide base pairing. Any nucleotide sequence can be employed as long as it facilitates homologous recombination at a specific and selected position along the target nucleic acid molecule (e.g., a gene encoding a MIF protein).

By "not functional" or "functionally inactive" is meant that the MIF protein is not operational or the MIF gene cannot synthesize a functional MIF protein.

"Expression vector" is given a functional definition, and any DNA sequence which is capable of effecting expression of a specified DNA code in a suitable host is included in this term. As at present, such vectors are frequently in the form of plasmids, thus "plasmid" and "expression vector" are often used interchangeably. However, the invention is intended to include such other forms of expression vectors which serve equivalent functions and which may, from time to time, become known in the art. Typically an "expression vector" is a nucleic acid molecule comprising (1) a promoter and other sequences (e.g., leader sequences) necessary to direct expression of a desired gene or DNA sequence, and (2) the desired gene or DNA sequence. Optionally, the nucleic acid molecule may comprise a poly A signal sequence to enhance the stability of the gene transcript and/or to increase gene transcription and expression.

"Transformation" refers to the introduction of DNA into a recipient host cell that changes the genotype and consequently results in a change in the recipient cell. "Transformation" and "transfection" are often used interchangably.

"Host cells" refers to cells which have been recombinantly transformed with vectors constructed using recombinant DNA techniques. One preferred host cell, may be a $MIF^{-/-}$ deficient cell. A less preferred host cell is one in which the cell is $MIF^{-/+}$. Additionally, host cells may also be those cells transfect with a nucleic acid encoding an immunoglobulin derived from a $MIF^{-/-}$ of the invention.

In descriptions of processes for isolation of antibodies from recombinant hosts, the terms "cell," "cell culture" and "cell line" are used interchangeably to denote the source of antibody, unless it is clearly specified otherwise. In other words, recovery of antibody from the "cells" may mean either from spun down whole cells, or from the cell culture containing both the medium and the suspended cells.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated nucleic acid molecule" which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition. Thus, for exanple, an isolated nucleic acid molecule which encodes a particular CDR polypeptide consists essentially of the nucleotide coding sequence for the subject molecular recognition unit.

By "modulating" or "regulating" is meant the ability of an agent to alter from the wild-type level observed in the individual organism the wild-type activity of a MIF. MIF activity can be regulated at transcription, translation, nucleic acid or protein stability or protein activity.

B. Method of Preparing a Knock-out Mouse or Other Transgenic Animal

Transgenic animals typically can be prepared by homologous recombination. Gene deletion or knockout can be performed as described by Capecchi, *Science* 244: 1288-92 (1982); Brinster, *Int. J. Dev. Biol.* 37: 89-99 (1993); and DOETSCHMAN, IN TRANSGENIC ANIMAL TECHNOLOGY: A LABORATORY HANDBOOK 115-146 (C. A. Pinkert et al., ed., 1994). Knock-out animals can be prepared using embryonic stem (ES) cells or ES-like cells.

C. ES Cells

The genome of ES cells can be manipulated in vitro by introducing a desired foreign DNA by such techniques as electroporation, microinjection, precipitation reactions, transfection or retroviral insertion (Bradley et al., *Nature* 309: 255-6 (1984); Gossler et al., *Proc. Natl. Acad. Sci. U.S.A.* 83: 9065-9 (1986); ROBERTSON ET AL., TERATOCARCINOMAS AND EMBRYONIC STEM CELLS: A PRACTICAL APPROACH (1987); Kuehn et al., *Nature* 326: 295-8 (1987); Thompson et al., *Cell* 56: 313-21 (1989); Zimmer et al., *Nature* 338: 150-3 (1989); and Doetschrnan (1994).

ES-like cell lines have been identified and can be used as described by:

| | |
|---|---|
| Hamsters | Doetschman et al., Dev. Biol. 127: 224-7 (1988) |
| Pigs | Notarianni et al., J. Reprod. Fertil. Suppl. 41: 51-6 (1990); Piedrahita et al., Theriogenology 34: 879-90 1 (1990); and Strojek et al., Theriogenology 33: 901-13 (1990) |
| Sheep | Piedrahita et al. (1990). |

Other animals and methods of obtaining transgenic animals, using methods other than ES cells or ES-like cells, include those of lannaccone et al., *Dev. Biol.* 163: 288-92 (1994) for rats; Stice et al., *Theriogenology* 41: 301 (Abstract) (1994) for bovine fetuses, and Wheeler, *J. Reprod. Fertil.* 6 (Suppl.): 1-6 (1994) and Gerfen et al., *Anim. Biotech.* 6: 1-14 (1995) for pigs. The methods by Chemey et al., *Theriogenology* 41: 175 (1994) can be used for culturing bovine primordial germ cell-derived cell lines in culture. In addition to ES or ES-like cells, inner cell mass cells of blastocysts from animals such as bovines can be used as described by Van-Stekelenburg-Hamers et al., *Mol. Reprod. Dev.* 40: 444-54 (1995) and Collas et al., *Mol. Reprod. Dev.* 38: 264-7 (1994).

D. Nuclear Transfer

Homologous recombination events can also be used with nuclear transfer or transplantation. Using this technique eliminates the need for ES or ES-like cell lines. Nuclear transfer ca be performed using the methods described by Campbell et al., *Nature* 380: 64-8 (1996).

E. Homologous Recombination

In one aspect of the invention, a targeting vector is employed to insert a selectable marker into a predefined position of a gene (e.g., the gene encoding a MIF protein). The position is selected to achieve functional disruption of the gene upon insertion of the selectable marker. For such purposes, a preferred embodiment is a recombinant nucleic acid molecule comprising: (1) a 5' nucleotide sequence that is effective to achieve homologous recombination at a first predefined position of a mammalian MIF gene operably linked to (2) the 5' terminus of a first selectable nucleotide sequence which confers a first selection characteristic on a cell in which it is present, and (3) a 3' nucleotide sequence which is effective to achieve homologous recombination at a second predefined position of the MIF gene, operably linked to the 3' terminus of the first selectable nucleotide sequence. The recombinant nucleic acid molecule is effective to achieve homologous recombination in a mammalian chromosome at predefined location, which contains a gene encoding a MIF protein. Fragments of the targeting vector are also within the scope of the invention, e.g., recombinant nucleic acid molecules comprising elements (1) and (2), or comprising elements (2) and (3), etc.

Any nucleotide sequence can be employed, as long as it facilitates homologous recombination at a specific and selected position along the target nucleic acid molecule. Generally, there is an exponential dependence of targeting efficiency on the extent or length of homology between the targeting vector and the target locus. Selection and use of sequences effective for homologous recombination is described, e.g., in Deng et al., *Mol. Cell. Bio.* 12: 3365-71 (1992); Bollag et al., *Annu. Rev. Genet.* 23: 199-225 (1989); Waldman et al., *Mol. Cell. Bio.* 8: 5350-7 (1988).

An aspect of the present invention is to suppress or functionally disrupt expression of a MIF gene. The phrases "disruption of the gene", "gene disruption," "suppressing expression," "gene suppression," "functional inactivation of the gene," or "functional gene inactivation" refer to modification of the gene in a manner which prevents expression of that gene and/or its product (e.g., a MIF protein) in a cell. The expression of the gene's product is completely suppressed. A functionally disrupted gene, e.g., a functionally disrupted MIF gene, includes a modified gene that expresses a truncated MIF polypeptide having less than the entire coding sequence of the wild-type MIF gene. A gene can also be functionally disrupted by affecting its mRNA structure in such a way to create an untranslatable message, e.g., frame-shift, decreased stability, etc.

In accordance with the present invention, a MIF gene is modified in such a manner which is effective to disrupt expression of the corresponding gene product. Thus, a functionally disrupted recombinant MIF gene does not express a functional MIF polypeptide or expresses a functional MIF polypeptide at levels which are substantially less than wild-type levels of MIF. The gene can be modified in any effective position, e.g., enhancers, promoters, regulatory regions, noncoding sequences, coding sequences, introns, exons, etc., so as to decrease or prevent expression of that gene in a cell. Insertion into a region of a MIF gene, e.g., a MIF-1, MIF-2 or MIF-3 gene, is usually accomplished by homologous recombination. A recombinant nucleic acid molecule comprising regions of gene homology and a nucleotide sequence coding for a selectable marker gene is inserted into the promoter and/or coding region and/or noncoding regions of a MIF gene, whereby expression of the gene is functionally disrupted. When this knockout construct is then inserted into a cell, the construct can integrate into the genomic DNA. Thus, progeny of the cell will only express only one functional copy of the gene; the other copy will no longer express the gene product, or will express it at a decreased level, as the endogenous nucleotide sequence of the gene is now disrupted by the inserted nucleotide sequence. If desired, the functional gene can be inactivated in a second analogous step.

The nucleotide sequence effective for homologous recombination is operably linked to a nucleotide sequence, preferably a selectable marker nucleotide sequence or gene, which is to be inserted into the desired target nucleic acid. For example, an aspect of the present invention is to replace all or part of the nucleotide coding sequence for a MIF protein, with a nucleotide sequence for a selectable marker.

The recombinant nucleic acid is preferably inserted into a cell with chromosomal DNA that contains the endogenous gene to be knocked out. In the cell, the recombinant nucleic acid molecule can integrate by homologous recombination with the DNA of the cell in such a position so as to prevent or interrupt transcription of the gene to be knocked out. Such insertion usually occurs by homologous recombination (i.e., regions of the targeting vector that are homologous or complimentary to endogenous DNA sequences hybridize to each other when the targeting vector is inserted into the cell; these regions can then recombine so that part of the targeting vector is incorporated into the corresponding position of the endogenous genomic DNA).

As discussed, one or more nucleotide sequences can be inserted into a MIF gene to suppress its expression. It is desirable to detect the presence of the nucleotide sequence in the gene. Such detection can be accomplished in various ways, including by nucleic acid hybridization (e.g., Northern or Southern blot), antibody binding to a protein epitope encoded by the inserted nucleic acid, or by selection for a phenotype of the inserted sequence. Accordingly, such an inserted nucleotide sequence can be referred to as a first selectable nucleotide sequence. A first selectable nucleotide sequence preferably confers a first selection characteristic on a cell in which it is present. By the phrase "selection characteristic," it is meant, e.g., a characteristic which is expressed in a cell and which can be chosen in preference to another or other characteristics. The selectable nucleotide sequence, also known as selectable marker gene, can be any nucleic acid molecule that is detectable and/or assayable after it has been incorporated into the genomic DNA of the mammal. The selection characteristic can be a positive characteristic, i.e., a characteristic which is expressed or acquired by cells and whose presence enables selection of such cells. A positive selection characteristic can enable survival of the cell or organism, e.g., antibiotic resistance, ouabain-resistance (a gene for an ouabain-resistant sodium/potassium ATPase protein). Examples of positive selection characteristics and a corresponding selection agent include, e.g., Neo and G418 or kanomycin; Hyg and hygromycin; hisD and histidinol; Gpt and xanthine; Ble and bleomycin; and Hprt and hypoxanthine. See, e.g., U.S. Pat. No. 5,464,764 and Capecchi, *Science* 244: 1288-92 (1989). The presence of the selectable gene in the targeted sequence can also be identified by using binding ligands which recognize a product of the selectable gene, e.g., an antibody can be used to identify a polypeptide product coded for by the selectable gene, an appropriate ligand can be used to identify expression of a receptor polypeptide encoded by the selectable gene, or by assaying for expression of an enzyme encoded by the selectable gene. Preferably, the selectable marker gene encodes a polypeptide that does not naturally occur in the mammal.

The selectable marker gene can be operably linked to its own promoter or to another promoter from any source that will be active or can easily be activated in the cell into which it is inserted. However, the selectable marker gene need not have its own promoter attached, as it may be transcribed using the promoter of the gene into which it is inserted. The selectable marker gene can comprise one or more sequences to drive and/or assist in its expression, including, e.g., ribosome-recognition sequences, enhancer sequences, sequences that confer stability to the polypeptide or RNA, and/or a polvA sequence attached to its 3' end to terminate transcription of the gene. A positive selectable marker facilitates selection for recombinants in which the positive selectable marker has integrated into the target nucleic acid by homologous recombination. A gene targeting vector in accordance with the present invention can also further comprise a second selection characteristic encoded by a second selectable gene to further assist in the selection of correctly targeted recombinants. A negative selection marker permits selection against cells in which only non-homologous recombination has occurred. In one preferred embodiment, the second selectable marker gene confers a negative selection characteristic upon a cell in which it has been introduced. Such negative selection characteristics can be arranged in the targeting vector in such a way to facilitate discrimination between random integration events and homologous recombination. By the term "negative selection", it is meant a selection characteristic which, when acquired by the cell, results in its loss of viability (i.e., it is lethal to the cell). A nucleoside analog, gancyclovir, which is preferentially toxic to cells expressing HSV tk (herpes simplex virus thymidine kinase), can be used as a negative selection agent, as it selects for cells which do not have an integrated HSV tk selectable marker. FIAU (1,2-deoxy-2-fluoro-∀-d -arabinofuransyl-5-iodouracil) can also be used as a negative selection agent to select for cells lacking HSV tk. Other negative selectable markers can be used analogously. Examples of negative selection characteristics and a corresponding enzyme include thymidine kinase (HSV tk) and acyclovir, gancyclovir, or FIAU; Hprt and 6-thioguanine or 6-thioxanthine; diphtheria toxin; ricin toxin; cytosine deaminase and fluorocytosine.

The negative selectable marker is typically arranged on the gene targeting vector 5' or 3' to the recombinogenic homology regions so that double-crossover replacement recombination of the homology regions transfers the positive selectable marker to a predefined location on the target nucleic acid, but does not transfer the negative selectable marker. For example, a tk cassette can be located at the 3' end of a murine MIF gene, about 150 base pairs from the 3' stop codon. More than one negative selectable marker can also be utilized in a targeting vector. The positioning of, for example, two negative selection vectors at the 5' and 3' ends of a targeting vector further enhances selection against target cells which have randomly integrated the vector. Random integration sometimes results in the rearrangement of the vector, resulting in excision of all or part of the negative selectable marker prior to the random integration event. When this occurs, negative selection cannot be used to eliminate those cells which have incorporated the targeting vector by random integration rather than homologous recombination. The use of more than one negative selectable marker substantially enhances the likelihood that random integration will result in the insertion of at least one of the negative selectable markers. For such purposes, the negative selectable markers can be the same or different.

The use of a positive-negative selection scheme reduces the background of cells having incorrectly integrated, targeted construct sequences. Positive-negative selection typically involves the use of two active selectable markers: (1) a positive selectable marker (e.g., neo) that can be stably expressed following random integration or homologous targeting, and (2) a negative selectable marker (e.g., tk) that can only be stably expressed following random integration. By combining both positive and negative selection, host cells having the correctly targeted homologous recombination event can be efficiently obtained. Positive-negative selection schemes can be performed as described in, e.g., U.S. Pat. No. 5,464,764; and WO 94/06908. It is recognized, however, that one or more negative selectable markers are not required to carry out the present invention, e.g., produce a transgenic animal in which a MIF gene is functionally inactivated or disrupted.

A recombinant nucleic acid molecule according to the present invention can also comprise all or part of a vector. A vector is, e.g., a nucleic acid molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR54O, pRIT5 (Pharmacia). Eukaryotic: PWLNEO, pSV2CAT, pOG44, pXT1, pSG (Stratagene), pSVK3, PBPV, PMSG, pSVL (Pharmacia). However, any other vector, e.g., plasmids, viruses, or parts thereof, may be used as long as they are replicable and viable in the desired host. The vector can also comprise sequences that enable it to replicate in the host whose genome is to be modified. The use of such vector can expand the interaction period during which recombination can occur, increasing the targeting efficiency.

In accordance with an aspect of the present invention, the function of a MIF gene, such as MIF-1, is disrupted or knocked out by the insertion of an exogenous or heterologous sequence into it, interrupting its function. For example, the exogenous or heterologous sequence can be inserted into a region of the gene, such as MIF-1 before its first start codon. The nucleotide sequence coding for a selectable characteristic can be inserted into the MIF gene in such a manner by homologous recombination so that it is operably linked to an endogenous MIF gene promoter. Upon integration of the selectable marker gene into the desired predefined position of the MIF gene, expression of the selectable characteristic is driven by the endogenous MIF gene promoter, permitting its detection in those cells in which the construct has integrated.

The selectable marker gene can also be integrated at positions downstream of (3' to) the first start codon of the MIF gene. The MIF gene can be integrated out-of-reading frame or in-reading frame with the MIF polypeptide so that a fusion polypeptide is made, where the fusion polypeptide is less active than the normal product. By detecting only those cells which express the characteristic, cells can be selected which contain the integrated sequence at the desired location. A convenient way of carrying out such selection is using antibiotic resistance. As described herein, neomycin resistance is utilized as the selectable characteristic. Cells grown in the presence of a toxic concentration of G418 will normally die. Acquisition of the neomycin resistance gene (neo) by homologous recombination rescues cells from the lethal effect, thereby facilitating their selection.

The MIF gene is knocked-out or functionally interrupted by the integration event. The insertion of the selectable gene ahead of the MIF coding sequence effectively isolates it from a promoter sequence, disabling its expression. If the selectable gene contains a transcription terminator, then transcription of the gene using the MIF promoter will terminate immediately after it and will rarely result in the transcription of a MIF coding sequence. The MIF gene can also be knocked out by a deletion without a replacement, such as a site-directed deletion of a part of the gene. Deleted regions can be coding regions or regulatory regions of the gene.

A MIF gene can be modified at any desired position. It can be modified so that a truncated MIF polypeptide is produced having one or more activities of the complete MIF polypeptide. As already discussed, such a modified gene is a functionally disrupted gene.

If desired, the insertion(s) can be removed from the recombinant gene. For example, a neomycin cassette can replace exons of a mouse MIF gene to functionally inactivate it. The neomycin cassette can be subsequently removed from the MIF gene, e.g., using a recombinase system. The Cre-lox site specific recombination system is especially useful for removing sequences from a recombinant gene. To utilize the Cre-lox system, recombinase recognition sites are integrated into the chromosome along with the selectable gene to facilitate its removal at a subsequent time. For guidance on recombinase excision systems, see, e.g., U.S. Pat. Nos. 5,626,159, 5,527,695, and 5,434,066. See also, Orban et al., *Proc. Natl. Acad. Sci. USA* 89: 6861-5 (1992); O'Gorman et al., *Science* 251: 1351-5 (1991); and Sauer et al., *Nuc. Acids Res.* 17: 147-61 (1989).

A nucleic acid comprising a nucleotide sequence coding without interruption means that the nucleotide sequence contains an amino acid coding sequence for a polypeptide, with no non-coding nucleotides interrupting or intervening in the coding sequence, e.g., absent intron(s) or the noncoding sequence, as in a cDNA.

Another aspect of the present invention relates to host cells comprising a recombinant nucleic acid of the invention. A cell into which a nucleic acid is introduced is a transformed cell. Preferred nucleic acids include the knockout cassettes described above, as well as nucleic acids encoding a high affinity antibody or fragment thereof which is produced by a $MIF^{-/-}$ knockout animal. Host cells include, mammalian cells, e.g., murine Ltk-, murine embryonic stem cells, COS-7, CHO, HeLa, insect cells, such as Sf9 and Drosophila, bacteria, such as *E. coli, Streptococcus, bacillus*, yeast, fungal cells, plants, embryonic stem (ES) cells (e.g., mammalian, such as mouse), neuronal cells (primary or immortalized), e.g., NT-2, NT-2N, PC-12, SY-5Y, neuroblastoma. See, also Goeddel, *Methods in Enzymology* 185: 3-7 (1990) A nucleic acid can be introduced into the cell by any effective method including, e.g., calcium phosphate precipitation, electroporation, injection, pressure, DEAE-Dextran mediated transfection, fusion with liposomes, and viral transfection. When the recombinant nucleic acid is present in a mouse cell, it is preferably integrated by homologous recombination into the mouse cell gene locus. Additional methods are as described in SAMBROOK ET AL., MOLECULAR CLONING: A LABORATORY MANUAL (1989).

A transformed cell can contain a recombinant gene integrated into its chromosome at the targeted gene locus. A targeting vector which comprises sequences effective for homologous recombination at a particular gene locus, when introduced into a cell under appropriate conditions, will recombine with the homologous sequences at the gene locus, introducing a desired selectable gene into it. When recombination occurs such that insertion results, the nucleic acid is integrated into the gene locus. The gene locus can be the chromosomal locus which is characteristic of the species, or it can be a different locus, e.g., translocated to a different chromosomal position, on a supernumerary chromosome, on an engineered "chromosome," etc.

As discussed below, the present invention also relates to transgenic animals containing one or more modified MIF genes. The transgenic animals produced in accordance with the present invention can be used as a source to establish primary or established, e.g., immortalized, cell lines according to various methods as the skilled worker would know. Since the animals (either homozygotes or heterozygotes) contain a modified MIF gene, the corresponding cell lines would be expected to have the same genotype. The cell lines can be derived from any desired tissue or cell-type, including, e.g., liver, epithelia, neuron, fibroblast, mammary, lung, kidney, pancreas, stomach, thyroid, prostate, osteoblasts, osteoclasts, osteocytes, osteoprogenitor cells, muscle (e.g., smooth), etc.

Cell lines produced in accordance with the present invention are useful for a variety of purposes. In one aspect of the invention, it is desirable to create panels of cell lines which differ in the expression of one or more genes. For example, the present invention describes and enables the production of cell lines which lack a MIF gene, such as the MIF-1 gene. A MIF-functionally-disrupted cell line differs from the parental (i.e., starting) cell line by the expression of the MIF gene. The availability of such pairs of cell lines, i.e., plus or minus for MIF expression (or any other desired gene, e.g., MIF-2), is useful to distinguish the effects of MIF from those of other MIF genes products. A cell line functionally-disrupted in one or more desired proteases (e.g., MIF-1, MIF-2, etc.), in combination with the parental cell line intact for other MIF or MIF-like proteins, can be employed to specifically distinguish its activity (e.g., MIF-1) from all other MIF proteins. Such genetic dissection can be used to develop, e.g., drugs and therapeutics which target a specific gene product.

Gene functionally-disrupted cell lines can also be utilized to produce transgenic, either chimeric, heterozygous, or homozygous, animals, e.g., non-human mammals. Such transgenic animals are useful as models to study the physiological role of a desired gene and to identify agents which specifically target the desired gene or a biological pathway in which it acts. Thus, an aspect of the invention is method of administering to a mammal functionally-disrupted for a MIF or MIF-like gene, e.g., MIF, an amount of an agent effective to restore MIF activity.

The present invention also relates to a non-human transgenic animal, preferably a mammal, more preferably a mouse, which comprises a macrophage MIF gene, which has been engineered employing a recombinant nucleic acid according to the present invention. Generally, a transformed host cell, preferably a totipotent cell, whose endogenous gene has been modified using a recombinant nucleic acid as described above is employed as a starting material for a transgenic embryo. The preferred methodology for constructing such a transgenic embryo involves transformed embryonic stem (ES) cells prepared as described herein employing a targeting vector comprising a recombinant nucleic acid according to the invention. A particular gene locus, e.g., MIF-1, is modified by targeted homologous recombination in cultured ES or ES-like cells employing a targeting vector comprising a recombinant nucleic acid according to the invention. The ES or ES-like cells are cultured under conditions effective for homologous recombination. Effective conditions include any culture conditions which are suitable for achieving homologous recombination with the host cell chromosome, including effective temperatures, pH, medias, additives to the media in which the host cell is cultured (e.g., for selection, such as G418 and/or FIAU), cell densities, amounts of DNA, culture dishes, etc. Cells having integrated the targeting vector are selected by the appropriate marker gene present in the vector. After homologous recombination has been accomplished, the cells contain a chromosome having a recombinant gene. In a preferred embodiment, this recombinant gene contains a positive selectable marker gene fused to endogenous MIF gene sequences. The transformed or genetically modified ES or ES-like cells can be used to generate transgenic non-human mammals, e.g., mice, by injection into blastocysts and allowing the chimeric blastocysts to mature, following transfer into a pseudopregnant mother. See, e.g., TERATOMACARCINOMA AND EMBRYONIC STEM CELLS: A PRACTICAL APPROACH (E. J. Robertson, ed., IRL Press). Various stem cells can be used, as known in the art, e.g., AB-1, HM-1 D3, CC1.2, E-14T62a, or RW4. Offspring born to foster mothers may be screened initially for mosaic coat color, where a coat color selection strategy has been employed. Alternatively, DNA from tail or other suitable tissue of the offspring can be used to screen for the presence of the DNA targeting vector. Offspring that appear to be mosaics are then crossed to each other, if it believed they carry the modified gene in their germ line, in order to generate MIF deficient homozygotes. See, e.g., U.S. Pat. Nos. 5,557,032 and 5,532,158.

In addition to the ES or ES-like cell methods described herein, transgenic animals can be created by other methods, e.g., by pronuclear injection of recombinant genes into pronuclei of one-cell embryos, incorporating an artificial yeast chromosome into embryonic stem cells, gene targeting methods and embryonic stem cell methodology. See, e.g., U.S. Pat. Nos. 4,736,866; 4,873,191; 4,873,316; 5,082,779; 5,304,489; 5,174,986; 5,175,384; 5,175,385; and 5,221,778; and Gordon et al., *Proc. Natl. Acad. Sci. U.S.A.,* 77: 7380-4 (1980); Palmiter et al., *Cell* 41: 343-5 (1985); Palmiter et al., *Ann. Rev. Genet.* 20: 465-99 (1986); Askew et al., *Mol. Cell. Bio.* 13: 4115-24 (1993); Games et al., *Nature* 373: 523-7 (1995); Valancius et al., *Mol. Cell. Bio.* 11: 1402-8 (1991); Staceyetal., *Mol. Cell. Bio.* 14:1009-16 (1994); Hasty et al., *Nature* 350: 243-6 (1995); and Rubinstein et al., *Nucl. Acid Res.* 21: 2613-7 (1993).

As discussed, one aspect of the invention relates to a knock-out mammal, such as a mouse, comprising cells which contain at least one functionally disrupted, recombinant MIF gene (e.g., heterozygous or homozygous) at a chromosomal MIF gene locus. The cells and animals can be created in accordance with the examples below by inserting an exogenous nucleotide sequence into the MIF gene. However, other methods can be used to create a functionally interrupted gene. For example, a termination codon can be inserted into a MIF gene, using, e.g., a replacement type vector as described in Rubinstein et al., *Nucleic Acid Res.* 21: 2613-7 (1993) or a tag-and-exchange strategy as described in Askew et al., *Mol. Cell. Bio.* 13: 4115-24 (1993), etc. Functional interruption of a MIF gene can also be achieved classically by mutagenesis, such as chemical or radiation mutagenesis.

A recombinant nucleic acid molecule according to the present invention can be introduced into any non-human mammal, including a mouse (HOGAN ET AL., MANIPULATING THE MOUSE EMBRYO: A LABORATORY MANUAL (Cold Spring Harbor Laboratory, Cold Spring Harbor, N.Y., 1986)), pig (Hammer et al., *Nature* 315: 343-5 (1985)), sheep (Hammer et al., *Nature* 315: 343-345 (1985)), cattle, rat, or primate. See also, e.g., Church, *Trends in Biotech.* 5: 13-9 (1987); Clark et al., *Trends in Biotech.* 5: 20-4 (1987); DePamphilis et al., *BioTechniques* 6: 662-80 (1988); and STRATEGIES IN TRANSGENIC ANIMAL SCIENCE (Glenn M. Monastersky and James M. Robl, eds. 1995).

In the examples below, a murine MIF gene is modified by homologous recombination utilizing a gene targeting vector comprising regions of the murine MIF gene. To carry out genetic modification of another mammalian MIF gene, e.g., a rat or a primate, it may be desirable to obtain analogous regions of the target MIF gene. A MIF gene from another species, using a murine or human MIF gene, can be accomplished by various methods known in the art, e.g., PCR using a mixture of oligonucleotides based on a consensus sequence or MIF (e.g., Leytus et al., *Biochemistry* 27: 1067-74 (1988)), nucleic acid hybridization using oligonucleotides, cDNA, etc., at a desired stringency (e.g., SAMBROOK ET AL., MOLECULAR CLONING, 1989).

A transgenic animal according to the present invention can comprise one or more MIF genes which have been modified by genetic engineering. For example, a transgenic animal comprising a MIF gene which has been modified by targeted homologous recombination in accordance with the present invention can comprise other mutations, including modifications at other gene loci and/or transgenes. Modifications to these gene loci and/or introduction of transgenes can be accomplished in accordance with the methods of the present invention, or other methods as the skilled worker would know. For instance, double-mutants can be made by conventional breeding, i.e., crossing animals and selecting for a desired phenotype and/or genotype. In one embodiment of the invention, a transgenic animal can be constructed having at least a defective MIF-1 gene (e.g., a knock-out) and one or more other MIF or MIF-like genes coding for a MIF or MIF-like protein. In a preferred embodiment, the latter genes are null or functionally-disrupted. Such an animal can be homozygous (−/−) or heterozygous (−/+) for the desired loci, or a combination thereof.

For other aspects of the nucleic acids, polypeptides, antibodies, etc., reference is made to standard textbooks of molecular biology, protein science, and immunology. See, e.g., Davis et al., BASIC METHODS IN MOLECULAR BIOLOGY (Elsevir Sciences Publishing, Inc., New York 1986); Hames et al., NUCLEIC ACID HYBRIDIZATION (IL Press 1985), SAMBROOK ET AL., (1989); CURRENT PROTOCOLS IN PROTEIN SCIENCE (F. M. Ausubel et al., eds. John Wiley & Sons, Inc.), CURRENT PROTOCOLS IN HUMAN GENETICS (Nicholas C. Dracopoli et al., eds. John Wiley & Sons, Inc. 1994); CURRENT PROTOCOLS IN PROTEIN SCIENCE (John E. Coligan et al., eds. John Wiley & Sons, Inc. 1995); and CURRENT PROTOCOLS IN IMMUNOLOGY (John E. Coligan et al., ed. John Wiley & Sons, Inc. 1991).

F. Method of Raising Antibodies in a Knock-Out Animal

Antibodies can be obtained from the blood serum of a $MIF^{-/-}$ animal immunized with a MIF antigen.

i. MIF Antigen

The MIF antigen used to raise antibodies can be from a complete MIF protein from any species, fragments thereof and fusion proteins containing all or a portion of a MIF protein. MIF sequences include, but at not limited to, any of the following:

TABLE 1

| Name | GenPept Accession No. | Publication or Deposit |
|---|---|---|
| L-dopachrome-methyl ester tautomerase (macrophage MIF homolog) of *Trichuris trichiura* | P81748 | |
| D-dopachrome tautomerase (murine) | O35215 | Esumi et al., Mamm. Genome 9: 753-7 (1998). |
| Macrophage MIF homolog (BMMIF) (*Brugia malayi*) | P91850 | Pastrana et al., Infect. Immun. 66: 5955-63 (1998). |
| L-Dopachrome-methyl ester tautomerase (macrophage MIF homolog) *Trichinella spiralis* | P81529 | Pennock et al., Biochem. J. 335: 495-8 (1998). |
| L-Dopachrome-methyl ester tautomerase (macrophage MIF homolog) *Trichuris muris* | P81530 | Pennock et al., (1998) |
| MIF-Like Protein C52E4.2. *Caenorhabditis elegans* | Q18785 | |
| Macrophage MIF (Glycosylation-inhibiting factor) (GIF). *Sus scrofa* | P80928 | |
| Macrophage MIF (Glutathione-binding 13 kD Protein). *Rattus norvegicus* | P30904 | Sakai et al., Biochem. Mol. Biol. Int. 33: 439-46 (1994) |
| Macrophage MIF (Glycosylation-inhibiting factor, GIF).; *Homo sapiens* | P14174 | Weiser et al., Proc. Natl. Acad. Sci. U.S.A. 86: 7522-6 (1989); Mikayama et al., Proc. Natl. Acad. Sci. U.S.A. 90: 10056-60 (1993); Kato et al., Proc. Natl. Acad. Sci. U.S.A. 93: 3007-10 (1996) |
| Macrophage MIF(P12A). Bovine | P80177 | Galat et al., Eur. J. Biochem. 224: 417-21 (1994). |
| Macrophage MIF (delayed early response protein 6, DER6) (Glycosylation-inhibiting factor). Murine | P34884 | Bernhagen et al., Nature 365: 756-9 (1993); Mikayama et al., (1993). |
| Macrophage MIF. *Gallus gallus* | Q02960 | Wistow et al., Proc. Natl. Acad. Sci. U.S.A. 90: 1272-5 (1993). |
| Chain B, Macrophage MIF Y95f Mutant. *Mus musculus* | 5822094 | |
| Chain A, Macrophage MIF Y95f Mutant. *Mus musculus* | 5822093 | |
| Chain C, Macrophage MIF Y95f Mutant. *Mus musculus* | 5822092 | |
| Macrophage MIF. *Sus scrofa* | AAD50507 | Abraham et al., Domest. Anim. Endocrinol. 15: 389-6 (1998). |
| Macrophage MIF (glycosylation-inhibiting factor). *Homo sapiens* | 4505185 | Mikayama et al., (1993); Paralkar et al., Genomics 19: 48-51 (1994); Kozak et al., Genomics 27: 405-11 (1995); Budarf et al., Genomics 39: 235-6 (1997). |
| Chain C, Macrophage MIF with Pro-1 Mutated To Gly-1. *Homo sapiens.* | 5542327 | Lubetsky et al., Biochemistry 38: 7346-54 (1999). |
| Chain B, Macrophage MIF with Pro-1 Mutated To Gly-1. *Homo sapiens.* | 5542326 | Lubetsky et al., (1999). |
| Chain A, Macrophage MIF with Pro-1 Mutated To Gly-1. *Homo sapiens* | 5542325 | Lubetsky et al., (1999). |
| Chain C, Macrophage MIF with Alanine Inserted Between Pro-1 And Met-2. *Homo sapiens* | 5542179 | Lubetsky et al., (1999). |
| Chain B, Macrophage MIF With Alanine Inserted Between Pro-1 And Met-2.Met-2. *Homo sapiens* | 5542178 | Lubetsky et al., (1999). |
| Chain A, Macrophage MIF with Alanine Inserted Between Pro-1 and Met-2. *Homo sapiens* | 5542177 | Lubetsky et al., (1999). |
| Macrophage migration inhibitory factor-like protein. *Trichuris trichiura* | CAB46355 | |
| Macrophage MIF. *Bos taurus* | AAD38354 | |

TABLE 1-continued

| Name | GenPept Accession No. | Publication or Deposit |
|---|---|---|
| Macrophage MIF. *Wuchereria bancrofti* | AAC82615 | |
| Chain C, Macrophage MIF. *Homo sapiens* | 1942979 | Sun et al., Proc. Natl. Acad. Sci. U.S.A. 93: 5191-6 (1996) |
| Chain B, Macrophage MIF. *Homo sapiens* | 1942978 | Sun et al., (1996). |
| Chain A, Macrophage MIF. *Homo sapiens* | 1942977 | Sun et al., (1996). |
| Macrophage MIF. *Meriones unguiculatus* | AAC02629 | |
| Macrophage MIF. *Brugia malayi* | AAB60943 | |
| Macrophage MIF. Bovine | S32394 | Galat et al., FEBS Lett. 319: 233-6 (1993). |
| Macrophage migration inhibitory factor DER6 - mouse. | A44499 | Lanahan et al., Mol. Cell. Biol. 12: 3919-29 (1992); Wistow et al., (1993); Bernhagen et al., (1993); Mikayama et al., (1993); and Mitchell et al., J. Immunol. 154: 3863-70 (1995). |
| Macrophage inhibitory factor (F5 cells) - human (fragment). | A61386 | Oki et al., Lymphokine Cytokine Res. 10: 273-80 (1991). |
| Macrophage migration inhibitory factor. *Homo sapiens* | CAA80598 | Bernhagen et al., (1993); and Wistow et al., (1993). |
| MIF (rat liver), 115 aa | AAB32392 | Sakai et al., Biochem. Mol. Biol. Int. 33: 439-46 (1994). |
| p12a isoform = macrophage migration-inhibitory factor [cattle, Peptide, 114 aa]. | AAB32021 | Galat et al., (1994). |
| Macrophage MIF {N-terminal partial peptide, 39 aa} *Bos taurus*. | AAB26003 | Galat et al., (1993). |
| Macrophage MIF. *Rattus norvegicus* | AAB04024 | |
| Macrophage MIF. *Mus musculus* | CAA80583 | Bernhagen et al., (1993). |
| Macrophage MIF. *Mus musculus* | AAA91638 | Kozak et al., (1995). |
| Macrophage migration inihibitory factor. *Mus musculus* | AAA91637 | Bozza et al., Genomics 27: 412-19 (1995). |
| MIF. *Mus musculus* | AAA74321 | Mitchell et al., J. Immunol. 154: 3863-7 (1995). |
| Macrophage MIF. *Gallus gallus* | AAA48939 | Wistow et al., (1993). |
| Macrophage MIF. *Homo sapiens* | AAA36179 | Wistow et al., (1993). |
| Macrophage MIF. *Homo sapiens* | AAA21814 | Paralkar et al., (1994) |
| Macrophage MIF.-3 (human) | | U.S. Pat. Nos. 5,986,060; 5,650,295; ATCC No. 75712 |
| Macrophage MIF.-2 | | Hirose et al., Microbiol. Immunol. 35: 235-45 (1991). |
| Sequence 8 from U.S. Pat. No. 5,807,714 (antigen-specific glycosylation inhibiting factor (AgGIF)) | g5960276 | U.S. Pat. No. 5,897,714 |
| Sequence 4 from U.S. Pat. No. 5,807,714 (antigen-specific glycosylation inhibiting factor (AgGIF)) | g5960275 | U.S. Pat. No. 5,807,714 |
| Sequence 4 from U.S. Pat. No. 5,807,714 (antigen-specific glycosylation inhibiting factor (AgGIF)) | g5960274 | U.S. Pat. No. 5,897,714 |
| Sequence 4 from U.S. Pat. No. 5,807,714 (antigen-specific glycosylation inhibiting factor (AgGIF)) | g5960273 | U.S. Pat. No. 5,897,714 |
| Chain A, Human glycosylation-inhibiting factor | g1942169 | Kato et al., (1996). |
| Chain B, Human glycosylation-inhibiting factor | g1942170 | Kato et al., (1996). |

TABLE 1-continued

| Name | GenPept Accession No. | Publication or Deposit |
|---|---|---|
| Chain C, Human glycosylation-inhibiting factor | g1942171 | Kato et al., (1996). |
| Glycosylation-inhibiting factor - human | g2135300 | Weiser et al., (1989); and Paralkar et al., (1994). |
| Glycosylation-inhibiting factor - bovine | g1085446 | Galat et al., (1994). |
| Glycosylation-inhibiting factor | g402717 | Mikayama et al., (1993). |
| Glycosylation-inhibiting factor | g402702 | Mikayama et al., (1993). |

G. Method of Preparing Cell Lines Which Express Anti-MIF Antibodies

Once antibody secreting cells, which produce antibodies of a desired anti-MIF affinity, are isolated, these cells can be utilized using standard procedures to produce cell lines which produce the desired antibodies.

i. Hybridoma Preparation

Hybridomas secreting monoclonal antibodies can be prepared as described by Kohler and Milstein, *Nature* 256: 495-7 (1975) or by Galfré et al., *Methods Enzymol.* 73 (Pt. B): 3-46 (1981). Briefly, homozygous deficient MIF mice (MIF−/−) are immunized by subcutaneous injection of about 0.1 to 100 μg (preferably 10 μg) of MIF protein in complete Freund's adjuvant, followed approximately 2 weeks later by intraperitoneal injection of about 10 μg of MIF in incomplete Freund's adjuvant. Antisera is collected about 1 week later and is analyzed in a micro-ELISA using microtiter plates coated with MIF protein (about 1 μ/ml) and detection of bound immunoglobulins with horseradish peroxidase-conjugated rabbit anti-mouse IgG. The specific antibody concentration in these antisera is retrospectively calculated by ELISA on microtiter plates coated with the respective antigen using purified monoclonal antibodies for calibration. After an interval of at least 4 weeks, the mice are boosted intraperitoneally with 10 μg of MIF protein in saline on days 4 and 2 before the cell fusion. Spleen cells are isolated and fused with either P3×63.Ag.8-6.5.3 or Sp2/O-AG14 myeloma cells. After selection in hypoxanthine-aminopterine-thyinidine medium, the supernatants are screened for specific antibody production with an one-site, non-competitive, micro-ELISA using microtiter plates coated with MIF and detection of bound immunoglobulins as described above. Positive clones are used for the production of ascites in pristane-primed mice. The IgG fraction of the monoclonal antibodies can be purified from ascites by affinity-chromatography on protein A-Sepharaose.

It should be noted that injection schedules, the animal immunized, and the amount and type of MIF antigen used (e.g., MIF fusion protein, MIF peptides or porteins) can be varied as would be known to the skilled artisan. See, e.g., Ed Harlow et al., Aintibodies: A Laboratory Manual (1988).

ii. Antigen

The MIF antigen used to immunize the knock-out mice or other knock-out animal can be derived from various sources. MIF can be purified from biological samples by chromatography or other purification procedure. Alternatively, MIF can be prepared recombinantly in eukaryotes or prokaryotes as previously described. Whole MIF proteins can be injected into the animal, as well as MIF peptides. MIF peptides for use in raising anti-peptide anti-MIF antibodies are preferably greater than 6 consecutive MIF amino acids in length. Peptides can be prepared synthetically, recombinantly or by proteolytic cleavage of the MIF protein to produce proteolytic MIF fragments. Recombinant forms of MIF or MIF peptides can be in the form of a fusion protein, wherein MIF is fused to another protein or polypeptide such as maltose binding protein (MBP), β-galactosidase or other suitable protein. MIF peptides can also be expressed recombinantly.

H. Diseases to be Treated Using Anti-MIF Antibodies

Diseases mediated by MIF include inflammatory diseases, retinopathy, e.g. diabetic or SLE-associated retinopathy, delayed type hypersensitivity (DTH), conditions mediated by DTH, cancer, pathological conditions induced by viruses and other pathogens, adult respiratory distress syndrome (ARDS), autoimmune diseases, endotoxic shock, pathological conditions involving neovascularization and trauma.

In the instance of septic shock, MIF has been reported to be a major secreted protein released by anterior pituitary cells in response to lipopolysaccharide (LPS) and may be a critical mediator of septic shock (Calandra et al., *Nature* 377: 68-71 (1995); and Bernhagen et al., *Nature* 365: 756-9 (1993). Some have suggested that the counteraction or neutralization of MIF may serve as an adjunct therapy in sepsis (Bozza et al., *J. Exp. Med.* 189: 341-6 (1999)).

In cancer, MIF has been reported to be spontaneous expressed by human cancer cells (Shimizu et al., *Biochem. Biophys. Res. Commun.* 264: 751-8 (1999); and Bini et al., *Electrophoresis* 18: 2832-41 (1997)). MIF reportedly also mediates or is produced in elevated quantities in colonic adenomas (Shkolnik et al., *Am. J Gastroenterol.* 82: 1275-8 (1987)), human T-cell leukemia virus (HTLV) induced T-cell leukemia (Koeffler et al., *Blood* 64: 482-90 (1984)), prostatic adenocarcinoma (Meyer-Siegler et al., *Urology* 48: 448-52 (1996)), pseudolymphoma, sacroidosis, and acute myeloblastic leukemia (AML). Hypoxia can also induce transcription of MIF and MIF found, in the serum of head and neck cancer patients, has been correlated with the degree of hypoxia occurring in these patients (Koong et al., *Cancer Res.* 60: 883-7 (2000)). MIF has been reported to suppress p53 activity and has been suggested as a link between inflammation and tumorigenesis (Hudson et al., *J. Exp. Med.* 190:1375-82(1999)). Anti-MIF antibodies have been shown to inhibit growth and visualization of colon tumors in mice (Ogawa, 1999).

Delayed type hypersensitivity (DTH) related diseases include atopic dermatitis (Shimizu et al., *Biochem. Biophys. Res. Commun.* 240: 173-8 (1997)). Autoimmune diseases with potential MIF involvement include Gaucher's Disease, rheumatoid arthritis (see Leech et al., *Arthritis Rheum.* 42: 1601-8 (1999); Onodera et al., *J. Biol. Chem.* 275: 444-50 (2000); and Onodera et al., *Cytokine* 11: 163-7 (1999)), asthma, immunologically induced kidney disease and systemic lupus erythematosus. In rheumatoid arthritis, MIF seems to act by inducing expression of matrix metalloproteinases (MMPs), such as MMP-1 and MMP-3, by synoviocyte fibroblasts (Onodera et al., 2000). MIF also has been indicated to play a role in psoriasis (Steinhoff et al., *Br. J. Dermatol.* 141: 1061-6 (1999)). Moreover, although it was known that MIF played a role in experimental glomerulonephritis (GN), only recently have researchers reported that MIF is markedly up-regulated in proliferative forms of human GN and that this up-regulation correlated with leukocyte infiltration, histologic damage and renal function impairment (Lan et al., *Kidney Int.* 57: 499-509 (2000)).

In one aspect, the anti-MIF antibodies or the immunogenic fragments thereof are contemplated for use in modulating the diseases and conditions described above. Preferably, the antibodies or their immunogenic fragments would inhibit the activity of MIF in a subject, wherein the subject is preferably human. More specifically, the anti-MIF antibodies contemplated are proposed for use alone or as an adjunct therapy to prevent disease progression. Some anti-MIF antibodies, prepared by methods other than those disclosed herein and with different specificities and affinities, have been shown to, for example, protect mice against (1) LPS-induced septic shock related death (Bernhagen et al., 1993)); (2) lethal peritonitis induced by cecal ligation and puncture (CLP) (Calandra et al., *Nature Med.* 6: 164-70 (2000)), anti-glomerular basement membrane (GBM) induced glomerulonephritis (Lan et al., *J. Exp. Med.* 185: 1455-65 (1997)), collagen type II induced rheumatoid arthritis in mice (Mikulowska et al., *J. Immunol.* 158: 5514-7 (1997)) and adjuvant induced arthritis in rats (Leech et al., *Arthritis Rheum.* 41: 910-7 (1998)), and has slowed 38C13 B cell lymphoma growth and vascularization in mice (Chesney et al., *Mol. Med.* 5: 1181-91(1999)), and carcinoma growth and neovascularization (Ogawa et al., *Cytokine* 12: 309-14 (2000)).

I. Anti-MIF Antibody or Antibody Fragment Compositions and Administration

An antibody or fragment thereof of the invention is administered to subjects in a biologically compatible form suitable for pharmaceutical administration in vivo. By "biologically compatible form suitable for administration in vivo" is meant a form of the antibody or fragment to be administered in which any toxic effects are outweighed by the therapeutic effects of the antibody or fragment. An antibody or fragment can be administered in any pharmacological form, optionally in a pharmaceutically acceptable carrier. Administration of a therapeutically effective amount of the antibody or fragment thereof is defined as an amount effective, at dosages and for periods of time necessary to achieve the desired result (e.g., inhibition of the progression or proliferation of the disease being treated). For example, a therapeutically active amount of an antibody or fragment thereof may vary according to such factors as the disease stage (e.g., stage I versus stage IV), age, sex, medical complications, and weight of the individual, and the ability of the antibody or fragment thereof to elicit a desired response in the individual. The dosage regimen may be adjusted to provide the optimum therapeutic response. For example, several divided doses may be administered daily, or the dose may be proportionally reduced as indicated by the exigencies of the therapeutic situation.

The active compound, an antibody or fragment thereof, by itself or in combination with other active agents, such as conventional anti-cancer drugs, steroids (e.g., glucocorticoids and cortico steroids) and additional antibodies or fragments thereof. Examples of steroids for use in combination with anti-MIF antibodies include dexamethasone and cortisol. Examples of glucocorticoids include: 21-Acetoxypregnenolone, Alclometasone, Algestone, Amcinonide, Beclomethasone, Betamethasone, Budesonide, Chloroprednisone, Clobetasol, Clobetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Flucinolone Acetonide, Fluocinonide, Fluocortin Butyl, Fluocortolone, Fluorometholone, Fluperolone Acetate, Fluprednidene Acetate, Fluprednisolone, Flurandrenolide, Fluticasone Propionate, Formocortal, Halcinonide, Halobetasol Propionate, Halometasone, Halopredone Acetate, Hydrocortamate, Hydrocortisone, Loteprednol Etabonate, Mazipredone, Medrysone, Meprednisone, Methylprednisolone, Mometasone Furoate, Paramethasone, Prednicarbate, Prednisolone, Prednisolone 25-Diethylaminoacetate, Prednisolone Sodium Phosphate, Prednisone, Prednival, Prednylidene, Rimexolone, Tixocortol, Triamcinolone, Triamcinolone, Acetonide, Triamcinolone Benetonide, Triamcinolone Hexacetonide. The immunoconjugate, alone or in combination with other agents, may be administered in a convenient manner such as by injection (subcutaneous, intramuscularly, intravenous, etc.), inhalation, transdermal application or rectal administration. Depending on the route of administration, the active compound may be coated with a material to protect the active compound from the action of enzymes, acids and other natural conditions, which may inactivate the compound. A preferred route of administration is by intravenous (I.V.) injection. Examples of conventional anti-cancer drugs include, but are not limited to methotrexate, taxol, cisplatin, tamoxifen, et seq.

To administer an antibody or fragment thereof by other than parenteral administration, it may be necessary to coat the antibody or fragment thereof with, or co-administer the antibody or fragment thereof with, a material to prevent its inactivation. For example, an antibody or fragment thereof can be administered to an individual in an appropriate carrier or diluent, co-administered with enzyme inhibitors or in an appropriate carrier or vector, such as a liposome. Pharmaceutically acceptable diluents include saline and aqueous buffer solutions. Liposomes include water-in-oil-in-water emulsions, as well as conventional liposomes (Strejan et al., *J Neuroimmunol.* 7: 27 (1984)). Additional pharmaceutically acceptable carriers and excipients are known in the art or as described in REMINGTOM'S PHARMACEUTICAL SCIENCES (18th ed. 1990).

The active compound may also be administered parenterally or intraperitoneally. Dispersions of the active compound also can be prepared in glycerol, liquid polyethylene glycols, and mixtures thereof and in oils. Under ordinary conditions of storage and use, these preparations may contain one or more preservatives to prevent the growth of microorganisms.

Pharmaceutical compositions suitable for injectable use include sterile, aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorBio acid, thimerosal and the like. In many cases, it will be preferable to include isotonic agents, for example, sugars, polyalcohols, such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating an active compound (e.g., an anti-MIF antibody or fragment thereof) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof When the active compound is suitably protected, as described above, the protein may be orally administered, for example, with an inert diluent or an assimilable edible carrier. As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. All compositions discussed above for use with an anti-MIF antibody or fragment thereof may also comprise supplementary active compounds in the composition.

It is especially advantageous to formulate parenteral compositions in dosage unit form for ease of administration and uniformity of a dosage. "Dosage unit form," as used herein, refers to physically discrete units suited as unitary dosages for the mammalian subjects to be treated; each unit containing a predetermined quantity of active compound is calculated to produce the desired therapeutic effect in association with the required pharmaceutical carrier. The specification for the dosage unit forms of the invention are dictated by and directly dependent on: (A) the unique characteristics of the active compound and the particular therapeutic effect to be achieved; and (B) the limitations inherent in the art of compounding such an active compound for the treatment of sensitivity in individuals.

J. In Vitro Functional Assays for Testing MIF-Neutralizing Antibodies

Several assays are available for testing whether a particular anti-MIF antibody produced from a MIF knockout animal, or a humanized antibody a portion of which is derived from an anti-MIF antibody produced from a knock out animal neutralize MIF-induced activity.

Figure 1:
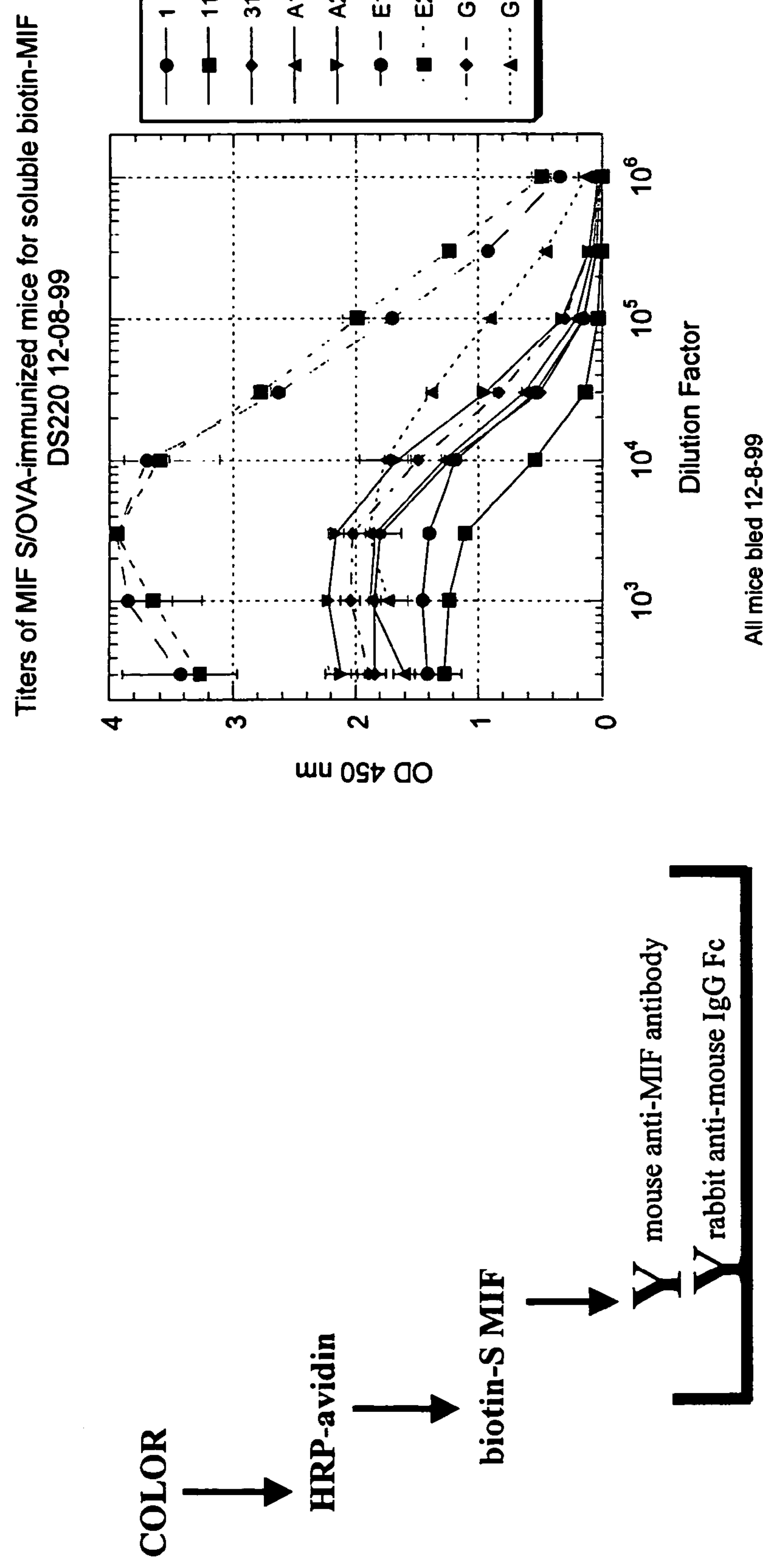
FIG. 1 shows the generation of high affinity, anti-MIF Mabs in MIF gene knock out mice as assayed by ELISA of the first fusion which was produced by human MIF S/OVA immunized mice (E1).
Figure 2:
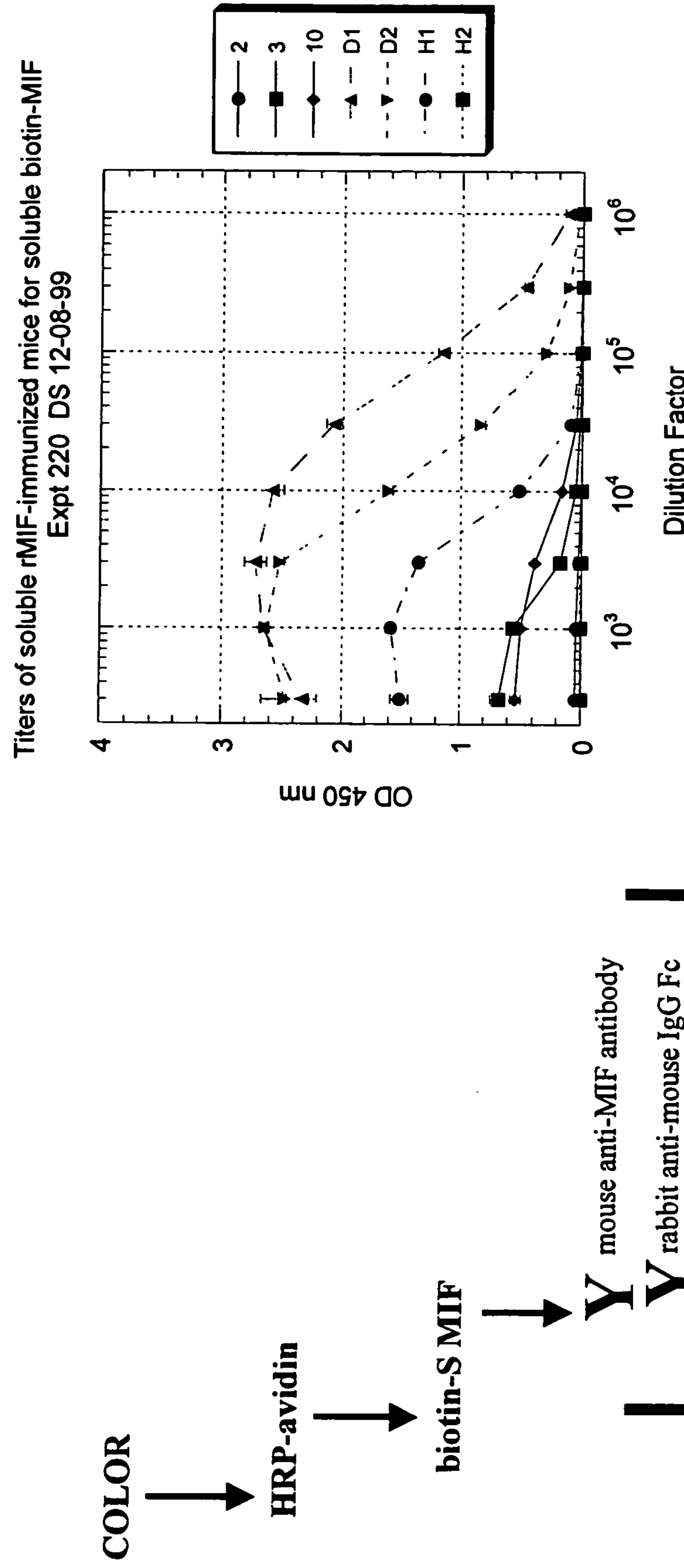
FIG. 2 shows the generation of high affinity, anti-MIF Mabs in MIF gene 5 knockout mice as tested by ELISA of the second fusion, which was produced by immunizing mice with solubler MIF. The antigen used in the ELISA for detection was biotin-MIF.
Figure 3:
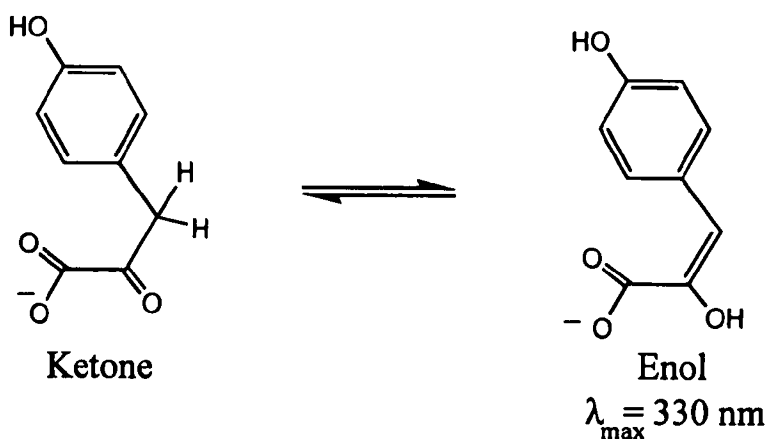
FIG. 3 shows that MIF catalyzes keto-enol tautomerase to tautomerizep-hydroxyphenylpyruvate.
Figure 3:
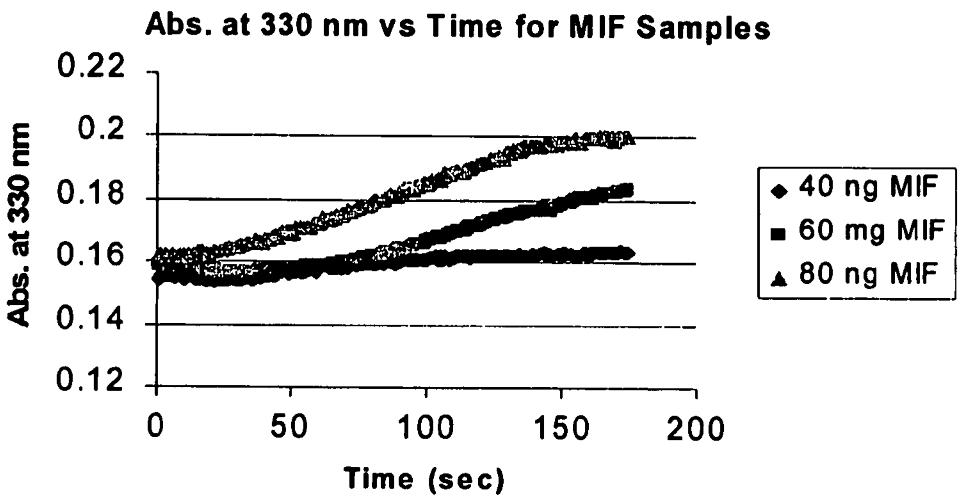

For example, one assay is the phenylpyruvate tautomerase (PPT) assay. This assay is based on the fact that MIF interconverts the enol- and keto-forms of phenylpyruvate and (p-hydroxyphenyl)pyruvate (Hermanowski-Vostka et al., *Biochem.* 38: 12841-9 (1999)). As shown in FIG. 3, MIF catalyzes the tautomerization of p-hydroxyphenylpyruvate. MIF also has been shown to possess D-dopachrome tautomerase and thiol protein oxidoreductase activities (Matsunaga et al., *Cell. Mol. Biol.* 45: 1035-40 (1999)). Accordingly, similar assays could be developed for the D-dopachrome and thiol protein oxidoreductase activities, as is described for the PPT assay.

Another in vitro assay can be performed in, for example NIH-3T3 cells, to determine the MIF activity inhibition based on the role of MIF (see FIG. 4) in the activation of the p44/p42 extracellular signal-regulated (ERK) mitogen-activated protein kinases (MAP) pathways, as discussed by Mitchell et al., *J. Biol. Chem.* 274: 18100-6 (1999). The activation of ELC by ERK ½ is discussed by Mitchell et al., (1999). The assay is a transcription-based assay for testing the efficacy of MIF neutralization by anti-MIF antibodies. A construct comprising a serum response element (SRE), promoter and Secreted alkaline phosphatase (SEAP) is created and transiently transfected into an appropriate cell line, such as NIH-3T3 cells. The expression of the SEAP gene is proportional to the transcriptional activation of ELK1 (e.g., EL1–pELK1$^{+}$). The impact of anti-MIF antibodies on MIF stimulated SRE-mediated transcription ascedrtained by measuring the alkaline phosphatase concentrations secreted (see FIG. 5). The alkaline phosphatase can be assessed using, for example a chemiluminescence detection system. Similar studies can be performed on MIF signaling events involving other phosphorylation of pathways involving transcription activation of AP-1, NF-KB and other factors.

Other in vitro studies for examining the activity of MIF signaling includes growth arrest and apoptosis studies. The potential target interactions include a MIF-mediated cascade involving override of 53 effects, tumor necrosis factor ∀ (TNF), sodium nitroprusside and glucocorticoids. In vitro assay systems, such as those described above, could be suitably altered to study each of these interactions, and thereby study the anti-MIF activity of the antibodies or fragments thereof in inhibiting said MIF activity.

Another assay would be based on MIF induction of MMP-1 release from cells. As discussed, MIF can up-regulate the matrix metalloproteinases (MMPs), such as MMP-1 (interstitial collagenase) and MMP-3 (stromelysin) (Onodera et al., 2000). Anti-MIF antibodies can then be tested for their ability to inhibit MIF induced MMP-1 release, for example, from human adult dermal fibroblasts. Other cells which produce MMPs would also be suitable for such assays, such as MMP-1 release from RA synovial fibroblasts.

Still another bioassay includes anti-MIF antibody inhibition of VEGF-stimulated endothelial cells. These assays include changes in proliferation and regulation of cell cycle and apoptosis.

K. In Vivo Models for Testine MIF-Neutralizing Antibodies

There are several in vivo models for testing the efficacy of a particular anti-MIF monoclonal antibody in an animal model. Lipopolysaccharide (LPS) induced disease is an animal model in which to examine septic shock (see, e.g., Bernhagen et al., *Nature* 365: 756-9 (1993)). Spontaneous mouse glomerulonephritis (GN) in mice strains such as female NZB/W F1 and NZM2410; GN can also be rapidly induced by injection of rabbit anti-GBM (glomerular basement membrane) serum (Lan et al., *J. Exp. Med.* 185:1455-65 (1997)). The animal models of adjuvant-induced arthritis (see Leech et al., *Arthritis Rheum.* 41: 910-7 (1998)) in rats, and collagen type II induced arthritis in mice (see Mikulowska et al., *J. Immunol.* 158: 5514-7 (1997)) are appropriate animal models for studying methods of treating human rheumatoid arthritis.

These animal models would be used to determine the inhibitory activity of anti-MIF monoclonal antibodies on MIF-induced activity in each of these diseases. For example, in the MIF/LPS lethality animal model, mice would be preinjected with an anti-MIF monoclonal antibody or negative control antibody. Two hours later the mice would receive an injection of MIF and LPS. Seven hours after the injection of MIF and LPS, the mice would receive an injection of MIF alone. The number of mice which survive this regimen of LPS-induced lethality would then be examined as compared to the control mice receiving an antibody other than an anti-MIF antibody (control) or mice not receiving any LPS. Survival would be plotted, typically at 24 hr, 48 hr, 72 hr and 96 hr after the MIF and LPS injection.

Uses

The present invention further is directed to use of anti-MIF antibodies for treatment and prophylaxsis of diseases, wherein suppression or modulation of MIF is therapeutically beneficial. Examples thereof include diseases involving cytokine-mediated toxicity. More specific examples are inflammatory diseases and autoimmune diseases, such as rheumatoid arthritis and other autoimmune diseases, graft-vs-host disease, TNF induced toxicity, endotoxin associated toxicity, septic shock, infections such as malarial, bacterial and viral infections, allergy, etc. Also, anti-MIF antibodies can be used to suppress undesirable immune responses. Such antibodies may be administered alone or in combination with other active agents, as described above.

The examples and methods provided below serve merely to illustrate particular embodiments of the invention and are not meant to limit the invention.

EXAMPLE 1

Preparation of a MIF Knock-Out Mouse

Targeting vector construction and generation of $MIF^{-/-}$ Mice. A mouse MIF genomic fragment is isolated from a 129SV/J genomic library (Bozza et al., *Genomics* 27: 412-19 (1995)), and a 6.1 kb XbaI fragment containing the 5' upstream region, exons 1-3, and the 3' region is subcloned in pBluescript®. The vector is digested with EcoRV (sites present in the 3' region of the gene and in the polylinker of the plasmid), releasing a 0.7 kb fragment. The vector is religated and digested with AgeI, which disrupts part of exon 2, the second intron, and exon 3. The neo cassette is inserted by blunt ligation after end-filling the vector and the neo cassette. The disrupted genomic vector is digested with XbaI/XhoI and ligated into the HSV-TK vector. The targeting vector is linearized with XhoI, and 30 μg is transfected by electroporation into $10^7$ J1 embryonic stem (ES) cells that are maintained on a feeder layer of neo embryonic fibroblasts in the presence of 500 U/ml of leukemia inhibitory factor. After 8 days of selection with G418 (200 μg/ml) and FIAU (2 μg), 30 clones are analyzed by Southern blot hybridization using the 0.7 kb EcoRV/XbaI 3' fragment as a probe. An ES cell line clone displaying a novel 7 kb XbaI allele predicted to occur after homologous recombination is injected into day 3.5 C57BL/6 blastocysts. The blastocysts are transferred into pseudopregnant females. Chimeric mice are bred with C57BL/6 mice and agouti offspring can be analyzed for the MIF disrupted allele by Southern blot hybridization.

Results. The mouse MIF gene can be disrupted by replacing part of exons 2 and 3 with a neo cassette. The targeting vector is electroporated in J1 ES cells and G418-FIAU-resistant colonies are isolated. Correctly targeted ES cells are used to generate chimeric animals by injection into C57BL/6 blastocysts. Highly chimeric animals transmitted the mutated allele through the germline. Homozygous mice are generated by intercrosses of heterozygous mice. Northern blot analysis from liver RNA of lipopolysaccharide (LPS)-treated animals can be used to confirm that the gene disruption creates a null mutation (Bozza et al., *J. Exp. Med.* 189: 341-6 (1999)). ELISA of serum from LPS-treated animals can be used to further confirm the absence of MIF protein in the $MIF^{-/-}$ mice (see Bozza et al., 1999). As described by Bozza et al., of the 218 animals obtained from heterozygous matings described above, 16% were homozygous for the null allele. The newborn $MIF^{-/-}$ mice developed normally in size and behavior and were fertile. The litter size of heterozygous and homozygous matings were normal. Both gross examination and histopathological analysis of several organs (kidney, liver, spleen, adrenal, thymus, lungs, heart, brain and intestine) of $MIF^{-/-}$ mice revealed no abnormalities. Flow cytometric analysis of splenocytes and thymocytes of $MIF^{-/-}$ mice demonstrated normal lymphocyte populations (Bozza et al., 1999).

EXAMPLE 2

Preparation of Anti-MIF Antibodies in a MIF Knock Out Mouse

Six week old mice, which are MIF knock out mice, are immunized by subcutaneous injection of 100 μg of MIF protein, MIF peptides fragment in Freund's Complete Adjuvant on day one, followed by a similar injection in Freund's Incomplete Adjuvant at day 10. Intraperitoneal injections are then performed at weekly intervals of 100 μg of MIF (or a MIF peptide fragment) in phosphate buffered saline (PBS). Blood is collected by supraorbital functions.

EXAMPLE 3

Preparation of Hybridomas

For hybridoma fusion, the spleen of the mice immunized in Example 2 are isolated and $1\times10^8$ splenocytes are fused to an equal number of Ag8 myeloma cells using the standard polyethylene glycol protocol. Selection in hypoxanthine/aminopterine/thymidine is initiated directly after replating the cell suspension into fifteen 96-well flat bottom plates. Supernatants are screened 10-14 days after the hybridoma fusion. Positive hybridomas can then be repeatedly subcloned.

Analysis of antibody affinity can be assayed by ELISA. For example, one μg of protein/ml PBS is coated in a 96-well polyvinylplate for 3 hours at 37° C. After three washes with PBS/0.05% Tween-20, the plates are blocked with PBS/0.1% bovine serum albumin (BSA) for 1 hour at 37° C. Again three washes are performed before the first antibody is incubated. Sera or antibodies are diluted in PBS/0.05% Tween-20/1% fetal calf serum (FCS). The serum incubation is performed for 1 hour at 37° C., followed by 3 washes. The enzyme conjugate RAMPO (Dakopats), is diluted 1000-fold and incubated for 1 h at 37° C. Tetra methyl benzidine (TMB) is used as the substrate for the peroxidase reaction. This reaction is stopped after 15 minutes, at room temperature by adding equal volume of 1 N $H_2SO_4$, at which time the optical density can be measured at 450 nm. As noted in Table 2 below, no high affinity anti-MIF generating hybridomas were produced from BALB/c mice, whereas using the MIF knockout mouse, numerous anti-MIF producing hybridomas were generated.

TABLE 2

Generation of Mabs that Bind MIF with High Affinity

| mouse | immu-nogen | #fusions | fusion date | #hybridomas generated | #anti-MIF hybridomas |
|---|---|---|---|---|---|
| BALB/c | MIF | 2 | Dec. 22, 1998 | 573 | 0 |
| BALB/c | MIF | 2 | Mar. 11, 1999 | 344 | 0 |
| BALB/c | MIF | 2 | May 10, 1999 | 384 | 0 |
| BALB/c | MIF | 3 | Aug. 05, 1999 | 500 | 0 |
| BALB/c | MIF/OVA | 1 | Dec. 21, 1999 | ? | 0 |
| MIF KO | MIF/OVA | 4 | Dec. 21, 1999 | 3242 | 671 |
| MIF KO | MIF | 3 | Feb. 14, 2000 | 2304 | 12 |

KO = MIF knockout mouse

EXAMPLE 4

Phenylpyruvate Tautomerase Assay

The assay for relative phenylpyruvate tautomerase activity of MIF was modified from Lubetsdy et al., *Biochemistry,* 38: 7346-7354 (1999). We used p-hydroxyphenylpyruvate (HPP) (Aldrich) as substrate. HPP was dissolved in 50 mM ammonium acetate (pH 6.0) at room temperature for overnight and stored in refrigerator until use. For catalytical activity measurement, 20 μl of HPP was added to 1.96 ml of 0.435 M boric acid (pH 6.2) and allowed to equilibrate in 1 ml quartz cuvette at room temperature for five minutes. To initiate the catalytic activity, 20 μl of 0.01 mg/ml rhMIF was added to above solution and thoroughly mixed. Activity was measured by following the increase in absorbance at 330 nm for five minutes. To study the effect of mouse anti-MIF anticlonal antibodies on the phenylpyruvate tautomerase activity of rhMIF, 0.2 μg of rhMIF is pre-incubation with 12.5 μg of antibody at 25° C. for one hour, then the 30 μl protein mixture was added to 1.97 ml of assay solution that contains HPP. For each antibody clone, the mean activity (slope of absorbance increase) was calculated from triplicate measurements. The relative activity was calculated by taking the percentage for the slope of the antibody-rhMIF samples to that of the rhMIF alone.

As shown in FIG. 3, when anti-MIF monoclonal antibodies (12.5 μg monoclonal antibody) are added to the reaction mixture containing MIF (0.2 μg MIF), the antibodies inhibits PPT activity. These results are summarized in Table 3 below. The outcomes are presented in the percent MIF-induced PPT activity remaining after the addition of each anti-MIF antibody.

TABLE 3

Ant-MIF Mabs Effects on MIF Phenylpyruvate tautomerase activity (12.5 Mg Mab + 0.2 μg MIF)

| Antibody | Subelone Off-Rate | % MIF PPT Activity |
|---|---|---|
| 30B7-11 | <1.0E−06 | −12 |
| 19B11-7 | 1.0E−05 | 0 |
| 22F11-6 | 2.0E−05 | 65 |
| 34D11-1 | 5.0E−05 | 54 |
| 2D8-3 | 8.0E−06 | 57 |
| 33G7-9 | <1.0E−06 | 67 |
| 6B5-5 | <1.0E−06 | 82 |
| 2G2-5 | 6.0E−05 | 92 |
| 9G10-12 | 3.6E−05 | 98 |
| 2B8 (murine anti-CD2O Mab) | — | 105 |
| 1OB11-3 | 9.0E−06 | 136 |
| IA9-7 | 2.0E−05 | 136 |
| 29B12-1 | <1.0E−06 | 146 |
| IIA9-8 | <1.0E−06 | 159 |
| 6E2-12 | <1.0E−06 | 188 |

EXAMPLE 5

Anti-MIF Mab Inhibition of MIF Induced SRE-SEAP Transcription/Secretion

The results depicted in FIG. 6 demonstrate that the addition of anti-MIF antibodies to a reaction containing MIF inhibited the stimulation of MIF induced SRE-SEAP transcription and secretion. The most inhibitory of the antibodies tested were the 6B5-5, 2G2-5 and 22F11-6 antibodies.

EXAMPLE 6

MIF Stimulated MMP-1 Release Assay

MIF is known to stimulate MMP-1 release from normal synovial fibroblasts or rheumatoid arthritis [Onodera, et al. (2000)]. When anti-MIF antibodies are added along with MIF, MIF stimulated MIMP-1 release from the fibroblasts is inhibited (FIG. 7). The antibodies 10B11-3, 2D8-3, 19B11-7 and 33G7-9 all inhibit MIF-induced MMP-1 release (FIG. 7, upper left panel). Additionally, 22F11-6, 6B5-5, 34D11-1, 9G10-12 and 2G2-5 also inhibit MIF induced MMP-I release (FIG. 7, upper right panel). Of these, the antibodies which prevent MIF-induced MMP-1 release, according to FIG. 7, lower panel, were 10B11-3, 6B5-5 and 22F11-6. Additional antibodies were tested for MIF inhibitory activity of MMP-1 release as seen in FIG. 8. In all instances, the concentration of antibody administered was 10 μg/ml. The results from this Example and Example 5 above can be summarized in Table 4 below:

TABLE 4

Anti-MIF Monoclonal Antibody Effects on In Vitro Bioassays

| MAB | Subclone Off-Rate | % MIF PPT Activity | 10 μg mab/ml MIF Stimulated SRE Transcription (% MIF Activity) | 10 μg mab/ml MIF Stimulated MMP-1 Release (% MIF Activity) | Binds Human MIF | Binds Murine MIF |
|---|---|---|---|---|---|---|
| None | — | — | 100% | 100% | N/A | N/A |
| 10B11-3 | 9.0E−06 | 136 | 0 (−83%) | 0 (−14.2%) | <0.1E−09 Kd | − |
| 22F11-6 | 2.0E−05 | 65 | 42% | 0 (−4.3%) | <0.1E−09 Kd | + |
| 6B5-5 | <1.0E−06 | 82 | 36% | 0 (−2.5%) | ++ | − |
| 2D8-3 | 8.0E−06 | 57 | 0 (−21%) | + | | |
| 34D11-1 | 5.0E−05 | 54 | 0% | + | | |
| 33G7-9 | <1.0E−06 | 67 | 5% | + | ++ | ++ |
| 29B12-1 | <1.0E−06 | 146 | 25% | + | ++ | − |
| 19B11-7 | 1.0E−05 | 0 | 29% | + | <0.1E−09 Kd | +++ |
| 2G2-5 | 6.0E−05 | 92 | 32% | + | ++ | − |
| 6E2-12 | <1.0E−06 | 188 | 0 (−250%) | − | | |
| 30B7-11 | <1.0E−06 | −12 | 0 (−53%) | − | | |
| IA9-7 | 2.0E−05 | 136 | 0 (−46%) | − | | |
| 9G10-12 | 3.6E−05 | 98 | 0 (−22%) | − | | |
| IIA9-8 | 1.0E−06 | 159 | 122% | − | | |
| Mab | | | | | Kd | |
| 24-31 (murine anti-CD154 mab) | | — | | − | | |
| IDEC-114 (anti-CD80 mab) | | | | | 2.2E−09 | |
| IDEC-152 (anti-BD23 mab) | | | | | 1.2E−09 | |

Also supplied in Table 4 is the human MIF and murine MIF binding capabilities of each of the listed antibodies.

EXAMPLE 7

MIF/LPS Lethality Model For Assessing Anti-MIF Antibodies

BALB/c mice were injected (all injections i.p. in this experiment) with lipopolysaccharide (LPS strain: E cell 0111: BY, Sigma Catalog #L2630) at 10 mg LPS/kg body weight. Some of the LPS-treated mice were then injected with 5 mg/kg monoclonal antibody (negative control) or an anti-MIF antibody (specific to human MIF). Additionally, MIF (R&R MIF Lot #US1600MBCO) was administered to said mice at a concentration of 2.5 mg/kg at the time of LPS injection (T=0) and seven hours later (T=7 hours). Mice pre-treated with anti-MIF monoclonal antibody at T=−2 hours had a greater percent survival than animals which received LPS and MIF or LPS and MIF and the negative-control antibody. These results are in FIG. 9.

A similar experiment was conducted wherein BALB/c mice were treated as described above, except that 12.5 mg/kg of LPS was administered instead of 10 mg/kg. As shown in FIG. 10, mice pre-treated with anti-MIF again had greater survival percentage than animals which did not receive antibody or which received the negative-control antibody.

Further, another similar experiment was effected except that 15.0 mg/kg LPS body weight was administered (rather than the previous 10.0 or 12.5 mg/kg body weight). Again, the animals which received anti-MIF had better survival percentages than animals which did not receive antibody or received the negative-control antibody.

These results are summarized in Table 5 as well as other activities of the tested antibodies specific to MIF.

TABLE 5

Anti-MIF Mab Effects on MIF + LPS Lethality in BALB/c Mice

| MAB | % MIF PPt Activity | 10 μg mab/ml MIF Stimulated SRE Transcription (% MIF Activity) | 10 μg mab/ml MIF Stimulated MMP-1 Release (% MIF Activity) | Binds Human MIF | Binds Murine MIF | Blocks LPS Lethality |
|---|---|---|---|---|---|---|
| 10B11-3 | 136 | 0 (−83%) | 0 (−14.2%) | <0.1E−09 Kd | − | |
| 22F11-6 | 65 | 42% | 0 (−4.3%) | <0.1E−09 Kd | + | + |
| 6B5-5 | 82 | 36% | 0 (−2.5%) | ++ | − | |
| 2D8-3 | 57 | 0 (−21%) | + | | | |
| 34D11-1 | 54 | 0% | + | | | |
| 33G7-9 | 67 | 5% | + | ++ | ++ | + |
| 29B12-1 | 146 | 25% | + | ++ | − | + |
| 19B11-7 | 0 | 29% | + | <0.1E−09 Kd | +++ | + |
| 2G2-5 | 92 | 32% | + | ++ | − | |
| 6E2-12 | 188 | 0 (−250%) | − | | | |

TABLE 5-continued

Anti-MIF Mab Effects on MIF + LPS Lethality in BALB/c Mice

| MAB | % MIF PPt Activity | 10 μg mab/ml MIF Stimulated SRE Transcription (% MIF Activity) | 10 μg mab/ml MIF Stimulated MMP-1 Release (% MIF Activity) | Binds Human MIF | Binds Murine MIF | Blocks LPS Lethality |
|---|---|---|---|---|---|---|
| 30B7-11 | −12 | 0 (−53%) | − | | | |
| IA9-7 | 136 | 0 (−46%) | − | | | |
| 9G10-12 | 98 | 0 (−22%) | − | | | |
| IIA9-8 | 159 | 122% | − | | | |
| 24-31 (murine anti-CD154 mab) | | | − | | | − |

The characteristics of two of the lead candidate antibodies are summarized below in Table 6:

TABLE 6

| | Mab 10B11-3 | Mab 22F11-6 |
|---|---|---|
| human MIF Kd < 50 nm | <0.1 nM | <0.1 nM |
| Neutralizes MIF in vitro 10 μg/ml MIF stimulated transcription SRE: SEAP | 100% | 58% |
| Neutralizes MIF in vitro 10 μg/ml MIF stimulated MMP-1 release | 100% | 100% |

The following Table 7 lists the antibodies generated from MIF knockout (KO) mice as well as anti-CD80 and anti-CD23 antibodies.

TABLE 7

Summary of Anti-MIF mabs generated from MIF gene knockout mice

| Hybridoma | Fusion | Parent CGM Off-Rate #1 | Parent CGM Off-Rate #2 | Subclone CGM Off-Rate | HYBRIDOMA STATUS |
|---|---|---|---|---|---|
| 29B12-1 | 1 | 3.5E−05 | <1.0E−06 | <1.0E−06 | purified from ascites fluid |
| 30B7-11 | 1 | 9.4E−06 | <6.0E−06 | <1.0E−06 | purified from ascites fluid |
| IIA9-8 | 1 | 3.6E−05 | <6.0E−06 | <1.0E−06 | purified from ascites fluid |
| 6B5-5 | 1 | 1.7E−05 | 3.0E−05 | <1.0E−06 | purified from ascites fluid |
| 33G7-9 | 1 | 1.8E−05 | — | <1.0E−06 | purified from ascites fluid |
| 6E2-12 | 1 | 2.9E−05 | 6.0E−05 | <1.0E−06 | purified from ascites fluid |
| 2D8-3 | 1 | 8.8E−05 | 4.5E−05 | 8.0E−06 | purified from ascites fluid |
| 10B11-3 | 1 | 1.7E−05 | <1.0E−06 | 9.0-E06 | purified from ascites fluid |
| 19B11-7 | 1 | 3.4E−06 | <1.0E−06 | 1.0E−06 | purified from ascites fluid |
| L2E1-9 | 1 | 1.0E−05 | <1.0E−05 | 1.0E−06 | expanded for CGM |
| IA9-7 | 1 | 4.5E−05 | <1.0E−06 | 2.0E−05 | purified from ascites fluid |
| 22F11-6 | 1 | 6.6E−05 | 2.0E−05 | 2.0E−05 | purified from ascites fluid |
| 7E10-11 | 1 | 9.4E−05 | 8.0E−05 | 2.0E−05 | expanded for CGM |
| 25D11 | 1 | 3.0E−05 | | | purified from CGM |
| 25D-11 | | 2.8E−05 | | | subclones frozen |
| 9G10-12 | 1 | 2.8E−05 | <1.0E−06 | 3.6E−05 | purified from ascites fluid |
| 22A5-12 | 1 | 9.2E−05 | 5.0E−05 | 4.0E−05 | expanded for CGM |
| 14H5 | 1 | 4.0E−05 | | | subclones frozen |
| 34D11-1 | 1 | 7.1E−05 | 1.0E−05 | 5.0E−05 | purified from ascites fluid |

TABLE 7-continued

Summary of Anti-MIF mabs generated from MIF gene knockout mice

| Hybridoma | Fusion | Parent CGM Off-Rate #1 | Parent CGM Off-Rate #2 | Subclone CGM Off-Rate | HYBRIDOMA STATUS |
|---|---|---|---|---|---|
| IDEC-114 (anti-CD80 mab) | | | | 5.4E−05 | |
| 2G2-5 | 1 | 9.4E−05 | 4.0E−5 | 6.0E−05 | purified form ascites fluid |
| L3A11-5 | 2 | 1.0E−05 | 8.0E−05 | 7.0E−05 | expanded for CGM |
| L4A10-8 | 2 | 1.0E−05 | 5.0E−05 | 8.0E−05 | expanded for CGM |
| K8H8-9 | 2 | 1.0E−05 | <1.0E−05 | 9.0-E−05 | expanded for CGM |
| 33C4 | 1 | 9.4E−05 | | | subclones frozen |
| L4C9-4 | 2 | 2.0E−04 | 8.0E−05 | 1.0E−05 | purified from CGM |
| K5C9-8 | 2 | 2.0E−04 | 1.0E−05 | 1.0E−05 | expanded for CGM |
| L1A6-7 | 2 | 3.0E−04 | N/D | 1.0E−05 | purified from CGM |
| 22C11-8 | 1 | 2.0E−04 | 1.6E−04 | 1.6E−04 | ready to purify from CGM |
| IIB1-4 | 1 | 2.2E−05 | 1.0E−05 | 2.0E−04 | expanded for CGM |
| 11H2-9 | 1 | 8.1E−05 | 1.5E−04 | 2.0E−04 | expanded for CGM |
| 33F6-10 | 1 | 7.8E−05 | 2.0E−04 | 2.0E−04 | expanded for CGM |
| 19D3-9 | 1 | 6.3E−05 | 3.0E−04 | 2.0E−04 | purified from CGM |
| L4G3 | 2 | 2.0E−04 | | | subclones frozen |
| 5A11-10 | 1 | 8.9E−05 | 3.0E−05 | 4.0E−05 | expanded for CGM |
| IDEC-152 (anti-CD23 mab) | | | | 4.8E−04 | |
| Total monoclonal hybridomas | | | | | 34 |
| Total mabs purified from ascites fluid | | | | | 14 |
| Total mabs to be purified from CGM | | | | | 20 |

EXAMPLE 8

Identification of Sequences

The DNA and amino acid sequences of several lead candidate antibodies were identified, particularly for 6B5, 10B11, 19B11, 22F11, 29B12 and 33G7 and are contained in FIGS. 17-30. These sequences may be further mutated in order to enhance binding affinity.

EXAMPLE 9

Administration of an Anti-MIF Antibody for Therapy

Anti-MIF antibody is administered at doses that may range from 1-5 mg/kg to patients with an inflammatory disease who are not being treated with other drugs, or to those who are being treated with steroids such as Dexamethasone or other anti-inflammatory drugs. In certain cases of chronic inflammatory conditions such as asthma, RA or nephritis, the combination treatment with anti-MIF antibody and, for example, steroids may lead to the reduction of the steroid maintenance dose. Under such conditions the antibody may be used as a steroid salvage therapy which will bring the steroid dose down to avoid the side effects of steroid high dose therapy. The anti-MIF antibody may be administered i.v., i.m. or s.c. at intervals that may vary from weekly to monthly dosing regimens.

Although the present invention has been described in detail with reference to examples above, it is understood that various modifications can be made without departing from the spirit of the invention. All references discussed above are hereby incorporated by reference in their entirety.

What is claimed is:

1. A method of preparing a high-affinity anti-migration inhibitory factor (anti-MIF) antibody or fragment thereof comprising the steps of:

(a) preparing a transgenic mouse in which both alleles of the endogenous genes encoding a MIF protein are functionally knocked out by a method comprising (i) introducing a MIF-targeting construct into a mouse embryonic stem (ES) cell;

(ii) introducing the modified mouse ES cell into a mouse embryo;

(iii) transplanting the modified embryo into a pseudopregnant mouse;

(iv) allowing said modified embryo to develop to term; and (v) identifying a transgenic mouse with germ cells in which at least one allele of the endogenous MIF gene is functionally knocked out; and (vi) breeding the transgenic mouse of step (v) to obtain a transgenic ($MIF^{-/-}$) mouse in which both alleles of the endogenous MIF genes encoding said MIF protein are functionally knocked out;

(b) immunizing said transgenic mouse with a MIF protein or a polypeptide fragment thereof; and (c) obtaining a high affinity anti-MIF antibody or fragment thereof from said animal.

2. The method of claim 1, wherein the high affinity anti-MIF antibody or fragment thereof recognizes and binds to MIF-1 or fragment thereof, MIF-2 or fragment thereof, or MIF-3 or fragment thereof.

3. A method for producing a transgenic mouse lacking an endogenous MIF gene, wherein said mouse produces high affinity anti-MIF antibodies, said method comprising:

(a) introducing a MIF targeting construct comprising a selectable marker sequence into a mouse embryonic stem (ES) cell;

(b) introducing the modified mouse ES cell into a mouse embryo;

(c) transplanting the modified embryo into a pseudopregnant mouse;

(d) allowing said modified embryo to develop to term; and (e) identifying a transgenic mouse whose genome comprises a disruption of the endogenous MIF gene of at least one allele;

(f) breeding the transgenic mouse of step (e) to obtain a transgenic mouse whose genome comprises a homozygous disruption of the endogenous MIF gene ($MIF^{-/-}$), wherein said disruption results in a mouse which lacks endogenous MIF as compared to a wild type mouse; and (g) immunizing the transgenic ($MIF^{-/-}$) mouse with complete MIF protein, a peptide fragment of a MIF protein, or a fusion protein containing all or a part of a MIF protein.

4. The method of claim 3, comprising immunizing the transgenic ($MIF^{-/-}$) mouse with a MIF protein produced by cellular expression of an endogenous MIF gene or a recombinant DNA expression construct encoding a MIF protein.

5. The method of claim 3, comprising immunizing the transgenic ($MIF^{-/-}$) mouse with a MIF peptide that is greater than 6 consecutive MIF amino acids in length, which peptide is prepared synthetically, recombinantly, or by proteolytic cleavage of a MIF protein.

6. The method of claim 3, comprising immunizing the transgenic ($MIF^{-/-}$) mouse with a MIF peptide of length selected from 6, 7, 8, 9, 10, 11, 12, 13, 14, 15, 16, 17, 18, 19, 20, 25, 30, 35, 40, 45 and 50 amino acids in length.

7. The method of claim 3, comprising immunizing the transgenic ($MIF^{-/-}$) mouse with a fusion protein comprising a MIF protein or a MIF peptide that is fused to a non-MIF protein or polypeptide.

8. The method of claim 7, wherein the fusion protein comprises a MIF protein or a MIF peptide that is fused to maltose binding protein or β-galactosidase.

9. The method of claim 1, wherein step (b) comprises immunizing said transgenic mouse with a human MIF protein or a polypeptide fragment thereof.

10. The method of claim 1, wherein the anti-MIF antibody obtained in step (c) binds to MIF with an equilibrium dissociation constant (Kd) that is less than $10^{-10}$ M.

11. The method of claim 3, wherein step (g) comprises immunizing the transgenic $MIF^{-/-}$ mouse with a complete human MIF protein, a peptide fragment of a human MIF protein, or a fusion protein containing all or a part of a human MIF protein.

12. The method of claim 3, wherein the transgenic $MIF^{-/-}$ mouse immunized in step (g) produces anti-MIF antibodies that bind to MIF with an equilibrium dissociation constant (Kd) that is less than $10^{-10}$ M.

* * * * *

SEQUENCE LISTING

```
<160> NUMBER OF SEQ ID NOS: 119

<210> SEQ ID NO 1
<211> LENGTH: 22
<212> TYPE: PRT
<213> ORGANISM: Mus sp.

<400> SEQUENCE: 1

Met Asp Phe Gln Val Gln Ile Ile Ser Phe Leu Leu Ile Ser Ala Ser
  1               5                  10                  15

Val Ile Met Ser Arg Gly
            20


<210> SEQ ID NO 2
```

-continued

```
<211> LENGTH: 20
<212> TYPE: PRT
<213> ORGANISM: Mus sp.

<400> SEQUENCE: 2

Met Ser Val Leu Thr Gln Val Leu Gly Leu Leu Leu Leu Trp Leu Thr
  1               5                  10                  15

Asp Ala Arg Cys
             20


<210> SEQ ID NO 3
<211> LENGTH: 33
<212> TYPE: PRT
<213> ORGANISM: Mus sp.

<400> SEQUENCE: 3

Met Glu Ala Pro Ala Gln Leu Leu Phe Gln Leu Ser Glu Met Glu Thr
  1               5                  10                  15

Asp Thr Leu Leu Leu Trp Val Leu Leu Leu Trp Val Pro Gly Ser Thr
             20                  25                  30

Gly


<210> SEQ ID NO 4
<211> LENGTH: 20
<212> TYPE: PRT
<213> ORGANISM: Mus sp.

<400> SEQUENCE: 4

Met Ser Val Leu Thr Gln Val Leu Gly Leu Leu Leu Leu Trp Leu Thr
  1               5                  10                  15

Gly Ala Arg Cys
             20


<210> SEQ ID NO 5
<211> LENGTH: 24
<212> TYPE: PRT
<213> ORGANISM: Mus sp.

<400> SEQUENCE: 5

Met Gly Ile Lys Met Glu Ser Gln Phe Gln Val Leu Met Phe Leu Leu
  1               5                  10                  15

Leu Trp Val Ser Gly Ala Cys Ala
             20


<210> SEQ ID NO 6
<211> LENGTH: 20
<212> TYPE: PRT
<213> ORGANISM: Mus sp.

<400> SEQUENCE: 6

Met Ser Val Leu Thr Gln Val Leu Gly Leu Leu Leu Leu Trp Leu Thr
  1               5                  10                  15

Gly Ala Arg Cys
             20


<210> SEQ ID NO 7
<211> LENGTH: 22
<212> TYPE: PRT
<213> ORGANISM: Mus sp.

<400> SEQUENCE: 7

Gln Ile Val Leu Thr Gln Ser Pro Ala Ile Met Ser Ala Phe Pro Gly
```

-continued

```
 1               5                  10                  15

Glu Lys Val Thr Ile Thr
             20


<210> SEQ ID NO 8
<211> LENGTH: 22
<212> TYPE: PRT
<213> ORGANISM: Mus sp.

<400> SEQUENCE: 8

Asp Ile Gln Met Thr Gln Ser Pro Ala Ser Leu Ser Val Ser Val Gly
 1               5                  10                  15

Glu Thr Val Thr Ile Thr
             20


<210> SEQ ID NO 9
<211> LENGTH: 22
<212> TYPE: PRT
<213> ORGANISM: Mus sp.

<400> SEQUENCE: 9

Asn Ile Val Leu Thr Gln Ser Pro Ala Ser Leu Ala Leu Ser Leu Gly
 1               5                  10                  15

Gln Arg Ala Thr Ile Ser
             20


<210> SEQ ID NO 10
<211> LENGTH: 22
<212> TYPE: PRT
<213> ORGANISM: Mus sp.

<400> SEQUENCE: 10

Asp Ile Gln Met Thr Gln Ser Pro Ala Ser Leu Ser Ala Ser Val Gly
 1               5                  10                  15

Glu Thr Val Thr Ile Thr
             20


<210> SEQ ID NO 11
<211> LENGTH: 22
<212> TYPE: PRT
<213> ORGANISM: Mus sp.

<400> SEQUENCE: 11

Asp Ile Val Met Thr Gln Ser Pro Ser Ser Leu Ala Met Ser Val Gly
 1               5                  10                  15

Gln Arg Val Thr Met Ser
             20


<210> SEQ ID NO 12
<211> LENGTH: 22
<212> TYPE: PRT
<213> ORGANISM: Mus sp.

<400> SEQUENCE: 12

Asp Ile Gln Met Thr Gln Ser Pro Ala Ser Leu Ser Ala Ser Val Gly
 1               5                  10                  15

Glu Thr Val Thr Ile Thr
             20


<210> SEQ ID NO 13
<211> LENGTH: 11
<212> TYPE: PRT
```

<213> ORGANISM: Mus sp.

<400> SEQUENCE: 13

Cys Ser Ala Ser Ser Ser Val Ser Tyr Met His
1 5 10

<210> SEQ ID NO 14
<211> LENGTH: 12
<212> TYPE: PRT
<213> ORGANISM: Mus sp.

<400> SEQUENCE: 14

Cys Arg Ala Ser Glu Asn Ile Tyr Ser Asn Leu Ala
1 5 10

<210> SEQ ID NO 15
<211> LENGTH: 16
<212> TYPE: PRT
<213> ORGANISM: Mus sp.

<400> SEQUENCE: 15

Cys Arg Thr Ser Glu Ser Val Asp Ser Tyr Ala Ser Ser Phe Met His
1 5 10 15

<210> SEQ ID NO 16
<211> LENGTH: 12
<212> TYPE: PRT
<213> ORGANISM: Mus sp.

<400> SEQUENCE: 16

Cys Arg Ala Ser Glu Asn Ile Tyr Ser Tyr Leu Thr
1 5 10

<210> SEQ ID NO 17
<211> LENGTH: 17
<212> TYPE: PRT
<213> ORGANISM: Mus sp.

<400> SEQUENCE: 17

Cys Lys Ser Ser Gln Ser Leu Leu Asn Ile Asn Gln Lys Ser Tyr Leu
1 5 10 15

Ala

<210> SEQ ID NO 18
<211> LENGTH: 12
<212> TYPE: PRT
<213> ORGANISM: Mus sp.

<400> SEQUENCE: 18

Cys Arg Ala Ser Glu Asn Ile Phe Asn Tyr Leu Ser
1 5 10

<210> SEQ ID NO 19
<211> LENGTH: 15
<212> TYPE: PRT
<213> ORGANISM: Mus sp.

<400> SEQUENCE: 19

Trp Phe Gln Gln Lys Pro Gly Thr Ser Pro Lys Leu Trp Ile Tyr
1 5 10 15

<210> SEQ ID NO 20
<211> LENGTH: 15
<212> TYPE: PRT

<213> ORGANISM: Mus sp.

<400> SEQUENCE: 20

Trp Tyr Gln Gln Lys Gln Gly Lys Ser Pro Gln Leu Leu Val Tyr
1 5 10 15

<210> SEQ ID NO 21
<211> LENGTH: 15
<212> TYPE: PRT
<213> ORGANISM: Mus sp.

<400> SEQUENCE: 21

Trp Tyr Gln Gln Lys Pro Gly Gln Ser Pro Lys Leu Leu Ile Tyr
1 5 10 15

<210> SEQ ID NO 22
<211> LENGTH: 15
<212> TYPE: PRT
<213> ORGANISM: Mus sp.

<400> SEQUENCE: 22

Trp Phe Gln Gln Lys Gln Gly Lys Ser Pro Gln Leu Leu Val Tyr
1 5 10 15

<210> SEQ ID NO 23
<211> LENGTH: 15
<212> TYPE: PRT
<213> ORGANISM: Mus sp.

<400> SEQUENCE: 23

Trp Tyr Gln Gln Lys Pro Gly Gln Ser Pro Lys Leu Leu Val Tyr
1 5 10 15

<210> SEQ ID NO 24
<211> LENGTH: 15
<212> TYPE: PRT
<213> ORGANISM: Mus sp.

<400> SEQUENCE: 24

Trp Tyr Gln Gln Lys Gln Gly Lys Ser Pro Gln Leu Leu Val Tyr
1 5 10 15

<210> SEQ ID NO 25
<211> LENGTH: 7
<212> TYPE: PRT
<213> ORGANISM: Mus sp.

<400> SEQUENCE: 25

Gly Thr Ser Asn Leu Ala Ser
1 5

<210> SEQ ID NO 26
<211> LENGTH: 7
<212> TYPE: PRT
<213> ORGANISM: Mus sp.

<400> SEQUENCE: 26

Ala Ala Thr Asn Leu Ala Asp
1 5

<210> SEQ ID NO 27
<211> LENGTH: 7
<212> TYPE: PRT
<213> ORGANISM: Mus sp.

<400> SEQUENCE: 27

```
Leu Ala Ser Asn Leu Glu Ser
  1               5
```

<210> SEQ ID NO 28
<211> LENGTH: 7
<212> TYPE: PRT
<213> ORGANISM: Mus sp.

<400> SEQUENCE: 28

```
Asp Ala Lys Thr Leu Ala Glu
  1               5
```

<210> SEQ ID NO 29
<211> LENGTH: 7
<212> TYPE: PRT
<213> ORGANISM: Mus sp.

<400> SEQUENCE: 29

```
Phe Ala Ser Thr Arg Glu Ser
  1               5
```

<210> SEQ ID NO 30
<211> LENGTH: 7
<212> TYPE: PRT
<213> ORGANISM: Mus sp.

<400> SEQUENCE: 30

```
Asn Val Lys Thr Leu Thr Asp
  1               5
```

<210> SEQ ID NO 31
<211> LENGTH: 32
<212> TYPE: PRT
<213> ORGANISM: Mus sp.

<400> SEQUENCE: 31

```
Gly Val Pro Val Arg Phe Ser Gly Ser Gly Ser Gly Thr Ser Tyr Ser
  1               5                  10                  15

Leu Thr Ile Ser Arg Met Glu Ala Glu Asp Ala Ala Thr Tyr Tyr Cys
             20                  25                  30
```

<210> SEQ ID NO 32
<211> LENGTH: 32
<212> TYPE: PRT
<213> ORGANISM: Mus sp.

<400> SEQUENCE: 32

```
Gly Val Pro Ser Arg Phe Ser Gly Ser Gly Ser Gly Thr Gln Tyr Ser
  1               5                  10                  15

Leu Asn Ile Tyr Ser Leu Gln Pro Glu Asp Phe Gly Ser Tyr Tyr Cys
             20                  25                  30
```

<210> SEQ ID NO 33
<211> LENGTH: 32
<212> TYPE: PRT
<213> ORGANISM: Mus sp.

<400> SEQUENCE: 33

```
Gly Val Pro Ala Arg Phe Ser Gly Ser Gly Ser Arg Thr Asp Phe Thr
  1               5                  10                  15

Leu Thr Ile Asp Pro Val Glu Ala Asp Asp Ala Ala Thr Tyr Tyr Cys
             20                  25                  30
```

-continued

<210> SEQ ID NO 34
<211> LENGTH: 32
<212> TYPE: PRT
<213> ORGANISM: Mus sp.

<400> SEQUENCE: 34

```
Gly Val Pro Ser Ser Phe Ser Gly Ser Gly Ser Gly Thr Gln Phe Ser
  1               5                  10                  15

Leu Lys Ile Ile Ser Leu Gln Pro Glu His Phe Gly Ser Tyr Tyr Cys
             20                  25                  30
```

<210> SEQ ID NO 35
<211> LENGTH: 32
<212> TYPE: PRT
<213> ORGANISM: Mus sp.

<400> SEQUENCE: 35

```
Gly Val Pro Asp Arg Phe Ile Gly Ser Gly Ser Gly Thr Asp Phe Thr
  1               5                  10                  15

Leu Thr Ile Ser Ser Val Gln Ala Glu Asp Leu Ala Asp Tyr Phe Cys
             20                  25                  30
```

<210> SEQ ID NO 36
<211> LENGTH: 32
<212> TYPE: PRT
<213> ORGANISM: Mus sp.

<400> SEQUENCE: 36

```
Gly Val Pro Ser Arg Phe Ser Gly Ser Gly Ser Gly Thr Gln Phe Ser
  1               5                  10                  15

Leu Lys Ile Asn Ser Leu Gln Pro Glu Asp Phe Gly Ser Tyr Tyr Cys
             20                  25                  30
```

<210> SEQ ID NO 37
<211> LENGTH: 9
<212> TYPE: PRT
<213> ORGANISM: Mus sp.

<400> SEQUENCE: 37

```
Gln Gln Arg Ser Ser Tyr Pro Trp Thr
  1               5
```

<210> SEQ ID NO 38
<211> LENGTH: 9
<212> TYPE: PRT
<213> ORGANISM: Mus sp.

<400> SEQUENCE: 38

```
Gln His Phe Trp Gly Thr Pro Tyr Thr
  1               5
```

<210> SEQ ID NO 39
<211> LENGTH: 9
<212> TYPE: PRT
<213> ORGANISM: Mus sp.

<400> SEQUENCE: 39

```
Gln Gln Ser Asn Glu Asp Pro Arg Thr
  1               5
```

<210> SEQ ID NO 40
<211> LENGTH: 9

<212> TYPE: PRT
<213> ORGANISM: Mus sp.

<400> SEQUENCE: 40

Gln His His Tyr Gly Arg Pro Tyr Thr
1 5

<210> SEQ ID NO 41
<211> LENGTH: 9
<212> TYPE: PRT
<213> ORGANISM: Mus sp.

<400> SEQUENCE: 41

Gln Gln His Tyr Ser Thr Pro Pro Thr
1 5

<210> SEQ ID NO 42
<211> LENGTH: 9
<212> TYPE: PRT
<213> ORGANISM: Mus sp.

<400> SEQUENCE: 42

Gln His His Tyr Asp Thr Pro Tyr Thr
1 5

<210> SEQ ID NO 43
<211> LENGTH: 12
<212> TYPE: PRT
<213> ORGANISM: Mus sp.

<400> SEQUENCE: 43

Phe Gly Gly Gly Thr Lys Leu Glu Ile Lys Arg Thr
1 5 10

<210> SEQ ID NO 44
<211> LENGTH: 12
<212> TYPE: PRT
<213> ORGANISM: Mus sp.

<400> SEQUENCE: 44

Phe Gly Gly Gly Thr Lys Leu Glu Ile Lys Arg Thr
1 5 10

<210> SEQ ID NO 45
<211> LENGTH: 12
<212> TYPE: PRT
<213> ORGANISM: Mus sp.

<400> SEQUENCE: 45

Phe Gly Gly Gly Thr Gln Leu Glu Ile Lys Arg Thr
1 5 10

<210> SEQ ID NO 46
<211> LENGTH: 12
<212> TYPE: PRT
<213> ORGANISM: Mus sp.

<400> SEQUENCE: 46

Phe Gly Gly Gly Thr Lys Leu Glu Ile Lys Arg Thr
1 5 10

<210> SEQ ID NO 47
<211> LENGTH: 12
<212> TYPE: PRT
<213> ORGANISM: Mus sp.

<400> SEQUENCE: 47

```
Phe Gly Ser Gly Thr Lys Leu Glu Ile Lys Arg Thr
  1               5                  10
```

<210> SEQ ID NO 48
<211> LENGTH: 12
<212> TYPE: PRT
<213> ORGANISM: Mus sp.

<400> SEQUENCE: 48

```
Phe Gly Arg Gly Thr Lys Leu Glu Ile Lys Arg Thr
  1               5                  10
```

<210> SEQ ID NO 49
<211> LENGTH: 390
<212> TYPE: DNA
<213> ORGANISM: Mus sp.
<220> FEATURE:
<221> NAME/KEY: CDS
<222> LOCATION: (1)..(390)

<400> SEQUENCE: 49

```
atg gat ttt cag gtg cag att ttc agc ttc ctg cta atc agt gcc tca       48
Met Asp Phe Gln Val Gln Ile Phe Ser Phe Leu Leu Ile Ser Ala Ser
  1               5                  10                  15

gtc ata atg tcc aga gga caa att gtt ctc acc cag tct cca gca atc       96
Val Ile Met Ser Arg Gly Gln Ile Val Leu Thr Gln Ser Pro Ala Ile
             20                  25                  30

atg tct gca ttt ccg ggg gag aag gtc acc ata acc tgc agt gcc agc      144
Met Ser Ala Phe Pro Gly Glu Lys Val Thr Ile Thr Cys Ser Ala Ser
         35                  40                  45

tca agt gta agt tac atg cac tgg ttc cag cag aag cca ggc act tct      192
Ser Ser Val Ser Tyr Met His Trp Phe Gln Gln Lys Pro Gly Thr Ser
     50                  55                  60

ccc aaa ctc tgg att tat ggg aca tcc aac ctg gct tct gga gtc cct      240
Pro Lys Leu Trp Ile Tyr Gly Thr Ser Asn Leu Ala Ser Gly Val Pro
 65                  70                  75                  80

gtt cgc ttc agt ggc agt gga tct ggg acc tct tac tct ctc aca atc      288
Val Arg Phe Ser Gly Ser Gly Ser Gly Thr Ser Tyr Ser Leu Thr Ile
                 85                  90                  95

agc cga atg gag gct gaa gat gct gcc act tat tac tgc cag caa agg      336
Ser Arg Met Glu Ala Glu Asp Ala Ala Thr Tyr Tyr Cys Gln Gln Arg
            100                 105                 110

agt agt tac ccg tgg acg ttc ggt gga ggc acc aag ctg gaa atc aaa      384
Ser Ser Tyr Pro Trp Thr Phe Gly Gly Gly Thr Lys Leu Glu Ile Lys
        115                 120                 125

cgt acg                                                              390
Arg Thr
    130
```

<210> SEQ ID NO 50
<211> LENGTH: 130
<212> TYPE: PRT
<213> ORGANISM: Mus sp.

<400> SEQUENCE: 50

```
Met Asp Phe Gln Val Gln Ile Phe Ser Phe Leu Leu Ile Ser Ala Ser
  1               5                  10                  15

Val Ile Met Ser Arg Gly Gln Ile Val Leu Thr Gln Ser Pro Ala Ile
             20                  25                  30

Met Ser Ala Phe Pro Gly Glu Lys Val Thr Ile Thr Cys Ser Ala Ser
```

-continued

```
        35                  40                  45

Ser Ser Val Ser Tyr Met His Trp Phe Gln Gln Lys Pro Gly Thr Ser
     50                  55                  60

Pro Lys Leu Trp Ile Tyr Gly Thr Ser Asn Leu Ala Ser Gly Val Pro
 65                  70                  75                  80

Val Arg Phe Ser Gly Ser Gly Ser Gly Thr Ser Tyr Ser Leu Thr Ile
                 85                  90                  95

Ser Arg Met Glu Ala Glu Asp Ala Ala Thr Tyr Tyr Cys Gln Gln Arg
            100                 105                 110

Ser Ser Tyr Pro Trp Thr Phe Gly Gly Gly Thr Lys Leu Glu Ile Lys
        115                 120                 125

Arg Thr
    130


<210> SEQ ID NO 51
<211> LENGTH: 387
<212> TYPE: DNA
<213> ORGANISM: Mus sp.
<220> FEATURE:
<221> NAME/KEY: CDS
<222> LOCATION: (1)..(387)

<400> SEQUENCE: 51

atg agt gtg ctc act cag gtc ctg ggg ttg ctg ctg ctg tgg ctt aca       48
Met Ser Val Leu Thr Gln Val Leu Gly Leu Leu Leu Leu Trp Leu Thr
  1               5                  10                  15

gat gcc aga tgt gac atc cag atg act cag tct cca gcc tcc cta tct       96
Asp Ala Arg Cys Asp Ile Gln Met Thr Gln Ser Pro Ala Ser Leu Ser
             20                  25                  30

gta tct gtg gga gaa act gtc acc atc aca tgt cga gca agt gag aat      144
Val Ser Val Gly Glu Thr Val Thr Ile Thr Cys Arg Ala Ser Glu Asn
        35                  40                  45

att tac agt aat tta gca tgg tat cag cag aaa cag gga aaa tct cct      192
Ile Tyr Ser Asn Leu Ala Trp Tyr Gln Gln Lys Gln Gly Lys Ser Pro
     50                  55                  60

cag ctc ctg gtc tat gct gca aca aac tta gca gat gga gtg ccg tca      240
Gln Leu Leu Val Tyr Ala Ala Thr Asn Leu Ala Asp Gly Val Pro Ser
 65                  70                  75                  80

agg ttc agt ggc agt gga tca ggc aca cag tat tcc ctc aat atc tac      288
Arg Phe Ser Gly Ser Gly Ser Gly Thr Gln Tyr Ser Leu Asn Ile Tyr
                 85                  90                  95

agc ctg cag cct gaa gat ttt gga agt tat tac tgt caa cat ttt tgg      336
Ser Leu Gln Pro Glu Asp Phe Gly Ser Tyr Tyr Cys Gln His Phe Trp
            100                 105                 110

ggt act ccg tac acg ttc gga ggg ggg acc aag ctg gaa atc aaa cgt      384
Gly Thr Pro Tyr Thr Phe Gly Gly Gly Thr Lys Leu Glu Ile Lys Arg
        115                 120                 125

acg                                                                  387
Thr


<210> SEQ ID NO 52
<211> LENGTH: 129
<212> TYPE: PRT
<213> ORGANISM: Mus sp.

<400> SEQUENCE: 52

Met Ser Val Leu Thr Gln Val Leu Gly Leu Leu Leu Leu Trp Leu Thr
  1               5                  10                  15

Asp Ala Arg Cys Asp Ile Gln Met Thr Gln Ser Pro Ala Ser Leu Ser
             20                  25                  30
```

-continued

```
Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Tyr Ser Leu Asn Ile Tyr
                85                  90                  95

Ser Leu Gln Pro Glu Asp Phe Gly Ser Tyr Tyr Cys Gln His Phe Trp
            100                 105                 110

Gly Thr Pro Tyr Thr Phe Gly Gly Gly Thr Lys Leu Glu Ile Lys Arg
        115                 120                 125

Thr


<210> SEQ ID NO 53
<211> LENGTH: 438
<212> TYPE: DNA
<213> ORGANISM: Mus sp.
<220> FEATURE:
<221> NAME/KEY: CDS
<222> LOCATION: (1)..(438)

<400> SEQUENCE: 53

atg gaa gcc cca gct cag ctt ctc ttc cag ctc tca gag atg gag aca       48
Met Glu Ala Pro Ala Gln Leu Leu Phe Gln Leu Ser Glu Met Glu Thr
  1               5                  10                  15

gac aca ctc ctg cta tgg gtg ctg ctg ctc tgg gtt cca ggt tcc aca       96
Asp Thr Leu Leu Leu Trp Val Leu Leu Leu Trp Val Pro Gly Ser Thr
            20                  25                  30

ggt aac att gtg ctg acc caa tct cca gct tct ttg gct ctg tct cta      144
Gly Asn Ile Val Leu Thr Gln Ser Pro Ala Ser Leu Ala Leu Ser Leu
        35                  40                  45

ggg cag agg gcc acc ata tcc tgc aga acc agc gaa agt gtt gat agt      192
Gly Gln Arg Ala Thr Ile Ser Cys Arg Thr Ser Glu Ser Val Asp Ser
    50                  55                  60

tat gcc agt agt ttt atg cac tgg tac cag cag aaa cca gga cag tca      240
Tyr Ala Ser Ser Phe Met His Trp Tyr Gln Gln Lys Pro Gly Gln Ser
 65                  70                  75                  80

ccc aaa ctc ctc atc tat ctt gca tcc aac cta gaa tct ggg gtc cct      288
Pro Lys Leu Leu Ile Tyr Leu Ala Ser Asn Leu Glu Ser Gly Val Pro
                85                  90                  95

gcc agg ttc agt ggc agt ggg tct agg aca gac ttc acc ctc acc att      336
Ala Arg Phe Ser Gly Ser Gly Ser Arg Thr Asp Phe Thr Leu Thr Ile
            100                 105                 110

gat cct gtg gag gct gat gat gct gca acc tat tac tgt cag caa agt      384
Asp Pro Val Glu Ala Asp Asp Ala Ala Thr Tyr Tyr Cys Gln Gln Ser
        115                 120                 125

aat gag gat cct cgg acg ttc ggt gga ggc acc cag ctg gaa atc aaa      432
Asn Glu Asp Pro Arg Thr Phe Gly Gly Gly Thr Gln Leu Glu Ile Lys
    130                 135                 140

cgt acg                                                              438
Arg Thr
145


<210> SEQ ID NO 54
<211> LENGTH: 146
<212> TYPE: PRT
<213> ORGANISM: Mus sp.

<400> SEQUENCE: 54
```

```
Met Glu Ala Pro Ala Gln Leu Leu Phe Gln Leu Ser Glu Met Glu Thr
  1               5                  10                  15

Asp Thr Leu Leu Leu Trp Val Leu Leu Leu Trp Val Pro Gly Ser Thr
             20                  25                  30

Gly Asn Ile Val Leu Thr Gln Ser Pro Ala Ser Leu Ala Leu Ser Leu
         35                  40                  45

Gly Gln Arg Ala Thr Ile Ser Cys Arg Thr Ser Glu Ser Val Asp Ser
     50                  55                  60

Tyr Ala Ser Ser Phe Met His Trp Tyr Gln Gln Lys Pro Gly Gln Ser
 65                  70                  75                  80

Pro Lys Leu Leu Ile Tyr Leu Ala Ser Asn Leu Glu Ser Gly Val Pro
                 85                  90                  95

Ala Arg Phe Ser Gly Ser Gly Ser Arg Thr Asp Phe Thr Leu Thr Ile
            100                 105                 110

Asp Pro Val Glu Ala Asp Asp Ala Ala Thr Tyr Tyr Cys Gln Gln Ser
        115                 120                 125

Asn Glu Asp Pro Arg Thr Phe Gly Gly Gly Thr Gln Leu Glu Ile Lys
    130                 135                 140

Arg Thr
145


<210> SEQ ID NO 55
<211> LENGTH: 387
<212> TYPE: DNA
<213> ORGANISM: Mus sp.
<220> FEATURE:
<221> NAME/KEY: CDS
<222> LOCATION: (1)..(387)

<400> SEQUENCE: 55

atg agt gtg ctc act cag gtc ctg ggg ttg ctg ctg ctg tgg ctt aca       48
Met Ser Val Leu Thr Gln Val Leu Gly Leu Leu Leu Leu Trp Leu Thr
  1               5                  10                  15

ggt gcc aga tgt gac atc cag atg act cag tct cca gcc tcc cta tct       96
Gly Ala Arg Cys Asp Ile Gln Met Thr Gln Ser Pro Ala Ser Leu Ser
             20                  25                  30

gca tct gtg gga gaa act gtc acc atc aca tgt cga gca agt gag aat      144
Ala Ser Val Gly Glu Thr Val Thr Ile Thr Cys Arg Ala Ser Glu Asn
         35                  40                  45

att tac agt tat tta aca tgg ttt cag cag aaa cag gga aaa tct cct      192
Ile Tyr Ser Tyr Leu Thr Trp Phe Gln Gln Lys Gln Gly Lys Ser Pro
     50                  55                  60

cag ctc ctg gtc tat gat gca aaa acc tta gca gaa ggt gtg cca tca      240
Gln Leu Leu Val Tyr Asp Ala Lys Thr Leu Ala Glu Gly Val Pro Ser
 65                  70                  75                  80

agt ttc agt ggc agt gga tca ggc aca cag ttt tct ctt aag atc atc      288
Ser Phe Ser Gly Ser Gly Ser Gly Thr Gln Phe Ser Leu Lys Ile Ile
                 85                  90                  95

agc ctg cag cct gaa cat ttt ggg agt tat tac tgt caa cat cat tat      336
Ser Leu Gln Pro Glu His Phe Gly Ser Tyr Tyr Cys Gln His His Tyr
            100                 105                 110

ggt cga cca tac acg ttc gga ggg ggg acc aag ctg gaa atc aaa cgt      384
Gly Arg Pro Tyr Thr Phe Gly Gly Gly Thr Lys Leu Glu Ile Lys Arg
        115                 120                 125

acg                                                                  387
Thr


<210> SEQ ID NO 56
```

-continued

```
<211> LENGTH: 129
<212> TYPE: PRT
<213> ORGANISM: Mus sp.

<400> SEQUENCE: 56

Met Ser Val Leu Thr Gln Val Leu Gly Leu Leu Leu Leu Trp Leu Thr
  1               5                  10                  15

Gly Ala Arg Cys Asp Ile Gln Met Thr Gln Ser Pro Ala Ser Leu Ser
             20                  25                  30

Ala Ser Val Gly Glu Thr Val Thr Ile Thr Cys Arg Ala Ser Glu Asn
         35                  40                  45

Ile Tyr Ser Tyr Leu Thr Trp Phe Gln Gln Lys Gln Gly Lys Ser Pro
     50                  55                  60

Gln Leu Leu Val Tyr Asp Ala Lys Thr Leu Ala Glu Gly Val Pro Ser
 65                  70                  75                  80

Ser Phe Ser Gly Ser Gly Ser Gly Thr Gln Phe Ser Leu Lys Ile Ile
                 85                  90                  95

Ser Leu Gln Pro Glu His Phe Gly Ser Tyr Tyr Cys Gln His His Tyr
            100                 105                 110

Gly Arg Pro Tyr Thr Phe Gly Gly Gly Thr Lys Leu Glu Ile Lys Arg
        115                 120                 125

Thr


<210> SEQ ID NO 57
<211> LENGTH: 414
<212> TYPE: DNA
<213> ORGANISM: Mus sp.
<220> FEATURE:
<221> NAME/KEY: CDS
<222> LOCATION: (1)..(414)

<400> SEQUENCE: 57

atg ggc atc aag atg gag tca cag att ctg gtc ctc atg ttt ctt ctg       48
Met Gly Ile Lys Met Glu Ser Gln Ile Leu Val Leu Met Phe Leu Leu
  1               5                  10                  15

ctc tgg gta tct ggt gcc tgt gca gac att gtg atg aca cag tct cca       96
Leu Trp Val Ser Gly Ala Cys Ala Asp Ile Val Met Thr Gln Ser Pro
             20                  25                  30

tcc tcc ctg gct atg tca gta gga cag agg gtc act atg agc tgc aag      144
Ser Ser Leu Ala Met Ser Val Gly Gln Arg Val Thr Met Ser Cys Lys
         35                  40                  45

tcc agt cag agc ctt tta aat atc aat caa aag agc tat ttg gcc tgg      192
Ser Ser Gln Ser Leu Leu Asn Ile Asn Gln Lys Ser Tyr Leu Ala Trp
     50                  55                  60

tac cag cag aaa cca gga cag tct cct aaa ctt ctg gta tac ttt gca      240
Tyr Gln Gln Lys Pro Gly Gln Ser Pro Lys Leu Leu Val Tyr Phe Ala
 65                  70                  75                  80

tcc act agg gaa tct ggg gtc cct gat cgc ttc ata ggc agt gga tct      288
Ser Thr Arg Glu Ser Gly Val Pro Asp Arg Phe Ile Gly Ser Gly Ser
                 85                  90                  95

ggg aca gat ttc act ctt acc atc agc agt gtg cag gct gaa gac ctg      336
Gly Thr Asp Phe Thr Leu Thr Ile Ser Ser Val Gln Ala Glu Asp Leu
            100                 105                 110

gca gat tac ttc tgt cag caa cat tat agt act cct ccc acg ttc ggt      384
Ala Asp Tyr Phe Cys Gln Gln His Tyr Ser Thr Pro Pro Thr Phe Gly
        115                 120                 125

tct ggg acc aag ctg gaa atc aaa cgt acg                              414
Ser Gly Thr Lys Leu Glu Ile Lys Arg Thr
    130                 135
```

-continued

<210> SEQ ID NO 58
<211> LENGTH: 138
<212> TYPE: PRT
<213> ORGANISM: Mus sp.

<400> SEQUENCE: 58

Met Gly Ile Lys Met Glu Ser Gln Ile Leu Val Leu Met Phe Leu Leu
1 5 10 15

Leu Trp Val Ser Gly Ala Cys Ala Asp Ile Val Met Thr Gln Ser Pro
20 25 30

Ser Ser Leu Ala Met Ser Val Gly Gln Arg Val Thr Met Ser Cys Lys
35 40 45

Ser Ser Gln Ser Leu Leu Asn Ile Asn Gln Lys Ser Tyr Leu Ala Trp
50 55 60

Tyr Gln Gln Lys Pro Gly Gln Ser Pro Lys Leu Leu Val Tyr Phe Ala
65 70 75 80

Ser Thr Arg Glu Ser Gly Val Pro Asp Arg Phe Ile Gly Ser Gly Ser
85 90 95

Gly Thr Asp Phe Thr Leu Thr Ile Ser Ser Val Gln Ala Glu Asp Leu
100 105 110

Ala Asp Tyr Phe Cys Gln Gln His Tyr Ser Thr Pro Pro Thr Phe Gly
115 120 125

Ser Gly Thr Lys Leu Glu Ile Lys Arg Thr
130 135

<210> SEQ ID NO 59
<211> LENGTH: 387
<212> TYPE: DNA
<213> ORGANISM: Mus sp.
<220> FEATURE:
<221> NAME/KEY: CDS
<222> LOCATION: (1)..(387)

<400> SEQUENCE: 59 atg agt gtg ctc act cag gtc ctg ggg ttg ctg ctg ctg tgg ctt aca 48
Met Ser Val Leu Thr Gln Val Leu Gly Leu Leu Leu Leu Trp Leu Thr
1 5 10 15 ggt gcc aga tgt gac atc cag atg act cag tct cca gcc tcc cta tct 96
Gly Ala Arg Cys Asp Ile Gln Met Thr Gln Ser Pro Ala Ser Leu Ser
20 25 30 gca tct gtg gga gaa act gtc acc atc aca tgt cgc gca agt gag aat 144
Ala Ser Val Gly Glu Thr Val Thr Ile Thr Cys Arg Ala Ser Glu Asn
35 40 45 att ttc aat tat tta tca tgg tat cag cag aaa cag gga aaa tct cct 192
Ile Phe Asn Tyr Leu Ser Trp Tyr Gln Gln Lys Gln Gly Lys Ser Pro
50 55 60 cag ctc ctg gtc tat aat gta aaa acc tta aca gat ggt gtg cca tca 240
Gln Leu Leu Val Tyr Asn Val Lys Thr Leu Thr Asp Gly Val Pro Ser
65 70 75 80 agg ttc agt ggc agt ggc tca ggc aca cag ttt tct ctg aag atc aac 288
Arg Phe Ser Gly Ser Gly Ser Gly Thr Gln Phe Ser Leu Lys Ile Asn
85 90 95 agc ctg cag cct gaa gat ttt ggc agt tat tac tgt caa cat cat tat 336
Ser Leu Gln Pro Glu Asp Phe Gly Ser Tyr Tyr Cys Gln His His Tyr
100 105 110 gat act ccg tac acg ttc gga agg ggg acc aag ctg gaa atc aaa cgt 384
Asp Thr Pro Tyr Thr Phe Gly Arg Gly Thr Lys Leu Glu Ile Lys Arg
115 120 125 acg 387

Thr

<210> SEQ ID NO 60
<211> LENGTH: 129
<212> TYPE: PRT
<213> ORGANISM: Mus sp.

<400> SEQUENCE: 60

```
Met Ser Val Leu Thr Gln Val Leu Gly Leu Leu Leu Leu Trp Leu Thr
  1               5                  10                  15

Gly Ala Arg Cys Asp Ile Gln Met Thr Gln Ser Pro Ala Ser Leu Ser
             20                  25                  30

Ala Ser Val Gly Glu Thr Val Thr Ile Thr Cys Arg Ala Ser Glu Asn
         35                  40                  45

Ile Phe Asn Tyr Leu Ser Trp Tyr Gln Gln Lys Gln Gly Lys Ser Pro
     50                  55                  60

Gln Leu Leu Val Tyr Asn Val Lys Thr Leu Thr Asp Gly Val Pro Ser
 65                  70                  75                  80

Arg Phe Ser Gly Ser Gly Ser Gly Thr Gln Phe Ser Leu Lys Ile Asn
                 85                  90                  95

Ser Leu Gln Pro Glu Asp Phe Gly Ser Tyr Tyr Cys Gln His His Tyr
            100                 105                 110

Asp Thr Pro Tyr Thr Phe Gly Arg Gly Thr Lys Leu Glu Ile Lys Arg
        115                 120                 125

Thr
```

<210> SEQ ID NO 61
<211> LENGTH: 18
<212> TYPE: PRT
<213> ORGANISM: Mus sp.

<400> SEQUENCE: 61

```
Met Arg Val Leu Ile Leu Leu Trp Leu Phe Thr Ala Phe Pro Gly Ile
  1               5                  10                  15

Leu Ser
```

<210> SEQ ID NO 62
<211> LENGTH: 19
<212> TYPE: PRT
<213> ORGANISM: Mus sp.

<400> SEQUENCE: 62

```
Met Gly Trp Ser Trp Val Phe Leu Phe Leu Leu Ser Gly Thr Ala Gly
  1               5                  10                  15

Val Leu Ser
```

<210> SEQ ID NO 63
<211> LENGTH: 19
<212> TYPE: PRT
<213> ORGANISM: Mus sp.

<400> SEQUENCE: 63

```
Met Ala Trp Val Trp Thr Leu Leu Phe Leu Met Ala Ala Ala Gln Ser
  1               5                  10                  15

Ala Gln Ala
```

<210> SEQ ID NO 64
<211> LENGTH: 39
<212> TYPE: PRT

<213> ORGANISM: Mus sp.

<400> SEQUENCE: 64

```
Met His Ala Arg Ala Ala Ala Ser Val Met Asp Ile Cys Arg Ile Arg
  1               5                  10                  15

Leu Thr Ser Asp Met Asp Phe Gly Leu Ser Leu Val Phe Leu Val Leu
             20                  25                  30

Val Leu Lys Gly Val Gln Cys
         35
```

<210> SEQ ID NO 65
<211> LENGTH: 18
<212> TYPE: PRT
<213> ORGANISM: Mus sp.

<400> SEQUENCE: 65

```
Met Met Val Leu Ser Leu Leu Tyr Leu Leu Thr Ala Ile Pro Gly Ile
  1               5                  10                  15

Leu Ser
```

<210> SEQ ID NO 66
<211> LENGTH: 30
<212> TYPE: PRT
<213> ORGANISM: Mus sp.

<400> SEQUENCE: 66

```
Asp Val Gln Leu Gln Glu Ser Gly Pro Gly Leu Val Lys Pro Ser Gln
  1               5                  10                  15

Ser Leu Ser Leu Thr Cys Thr Val Thr Gly Ser Ser Ile Thr
             20                  25                  30
```

<210> SEQ ID NO 67
<211> LENGTH: 30
<212> TYPE: PRT
<213> ORGANISM: Mus sp.

<400> SEQUENCE: 67

```
Glu Val Gln Leu Gln Gln Ser Gly Pro Glu Leu Val Lys Pro Gly Ala
  1               5                  10                  15

Ser Val Arg Ile Ser Cys Lys Thr Ser Gly Tyr Thr Ile Thr
             20                  25                  30
```

<210> SEQ ID NO 68
<211> LENGTH: 30
<212> TYPE: PRT
<213> ORGANISM: Mus sp.

<400> SEQUENCE: 68

```
Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Ser Phe Arg
             20                  25                  30
```

<210> SEQ ID NO 69
<211> LENGTH: 30
<212> TYPE: PRT
<213> ORGANISM: Mus sp.

<400> SEQUENCE: 69

```
Glu Val Lys Leu Glu Glu Ser Gly Gly Gly Leu Val Gln Pro Gly Gly
  1               5                  10                  15
```

```
Ser Met Lys Leu Ser Cys Ala Ala Ser Gly Phe Thr Phe Gly
             20                  25                  30


<210> SEQ ID NO 70
<211> LENGTH: 30
<212> TYPE: PRT
<213> ORGANISM: Mus sp.

<400> SEQUENCE: 70

Glu Val Lys Leu Val Glu Ser Gly Gly Gly Ser Val Gln Pro Gly Gly
  1               5                  10                  15

Ser Leu Lys Leu Ser Cys Ala Thr Ser Gly Phe Ile Phe Ser
             20                  25                  30


<210> SEQ ID NO 71
<211> LENGTH: 30
<212> TYPE: PRT
<213> ORGANISM: Mus sp.

<400> SEQUENCE: 71

Asp Val Gln Leu Gln Glu Ser Gly Pro Asp Leu Val Lys Pro Ser Gln
  1               5                  10                  15

Ser Leu Ser Leu Thr Cys Ser Val Thr Gly Tyr Ser Ile Thr
             20                  25                  30


<210> SEQ ID NO 72
<211> LENGTH: 6
<212> TYPE: PRT
<213> ORGANISM: Mus sp.

<400> SEQUENCE: 72

Ser Asp Tyr Ala Trp His
  1               5


<210> SEQ ID NO 73
<211> LENGTH: 5
<212> TYPE: PRT
<213> ORGANISM: Mus sp.

<400> SEQUENCE: 73

Glu Tyr Thr Met His
  1               5


<210> SEQ ID NO 74
<211> LENGTH: 5
<212> TYPE: PRT
<213> ORGANISM: Mus sp.

<400> SEQUENCE: 74

Asn Tyr Gly Met Asn
  1               5


<210> SEQ ID NO 75
<211> LENGTH: 5
<212> TYPE: PRT
<213> ORGANISM: Mus sp.

<400> SEQUENCE: 75

Asp Ala Trp Met Tyr
  1               5


<210> SEQ ID NO 76
<211> LENGTH: 5
<212> TYPE: PRT
```

<213> ORGANISM: Mus sp.

<400> SEQUENCE: 76

```
Asp Tyr Tyr Met Tyr
  1               5
```

<210> SEQ ID NO 77
<211> LENGTH: 6
<212> TYPE: PRT
<213> ORGANISM: Mus sp.

<400> SEQUENCE: 77

```
Ser Gly Tyr Tyr Trp Asn
  1               5
```

<210> SEQ ID NO 78
<211> LENGTH: 14
<212> TYPE: PRT
<213> ORGANISM: Mus sp.

<400> SEQUENCE: 78

```
Trp Ile Arg Gln Phe Pro Gly Asn Lys Leu Glu Trp Met Gly
  1               5                   10
```

<210> SEQ ID NO 79
<211> LENGTH: 14
<212> TYPE: PRT
<213> ORGANISM: Mus sp.

<400> SEQUENCE: 79

```
Trp Met Lys Gln Ser His Glu Lys Ser Leu Glu Trp Ile Gly
  1               5                   10
```

<210> SEQ ID NO 80
<211> LENGTH: 14
<212> TYPE: PRT
<213> ORGANISM: Mus sp.

<400> SEQUENCE: 80

```
Trp Val Ser Gln Pro Pro Gly Lys Gly Leu Glu Trp Met Gly
  1               5                   10
```

<210> SEQ ID NO 81
<211> LENGTH: 14
<212> TYPE: PRT
<213> ORGANISM: Mus sp.

<400> SEQUENCE: 81

```
Trp Val Arg Gln Ser Pro Glu Lys Gly Leu Glu Trp Val Ala
  1               5                   10
```

<210> SEQ ID NO 82
<211> LENGTH: 14
<212> TYPE: PRT
<213> ORGANISM: Mus sp.

<400> SEQUENCE: 82

```
Trp Val Arg Gln Thr Pro Glu Lys Arg Leu Glu Trp Val Ala
  1               5                   10
```

<210> SEQ ID NO 83
<211> LENGTH: 14
<212> TYPE: PRT
<213> ORGANISM: Mus sp.

-continued

<400> SEQUENCE: 83

Trp Ile Arg Gln Phe Pro Gly Asn Lys Leu Glu Trp Val Gly
1 5 10

<210> SEQ ID NO 84
<211> LENGTH: 16
<212> TYPE: PRT
<213> ORGANISM: Mus sp.

<400> SEQUENCE: 84

Tyr Ile Ser Phe Ser Gly Ser Thr Gly Tyr Asn Pro Ser Leu Lys Ser
1 5 10 15

<210> SEQ ID NO 85
<211> LENGTH: 17
<212> TYPE: PRT
<213> ORGANISM: Mus sp.

<400> SEQUENCE: 85

Gly Ile Thr Pro Asn Thr Gly Val Leu Ser Asp Asn Gln Lys Phe Arg
1 5 10 15

Gly

<210> SEQ ID NO 86
<211> LENGTH: 17
<212> TYPE: PRT
<213> ORGANISM: Mus sp.

<400> SEQUENCE: 86

Trp Ile Asn Thr Tyr Thr Gly Glu Pro Thr Tyr Ala Asp Asp Phe Lys
1 5 10 15

Gly

<210> SEQ ID NO 87
<211> LENGTH: 19
<212> TYPE: PRT
<213> ORGANISM: Mus sp.

<400> SEQUENCE: 87

Glu Ile Arg Ser Lys Ala His Asn His Ala Thr Tyr Tyr Ala Glu Ser
1 5 10 15

Val Lys Gly

<210> SEQ ID NO 88
<211> LENGTH: 17
<212> TYPE: PRT
<213> ORGANISM: Mus sp.

<400> SEQUENCE: 88

Tyr Ile Ser Ile Gly Ser Gly Asn Thr Tyr Tyr Pro Asp Thr Val Lys
1 5 10 15

Gly

<210> SEQ ID NO 89
<211> LENGTH: 16
<212> TYPE: PRT
<213> ORGANISM: Mus sp.

<400> SEQUENCE: 89

Tyr Leu Ser Tyr Asp Gly Ser Lys Ser His Asn Pro Ser Leu Arg Asn
1 5 10 15

<210> SEQ ID NO 90
<211> LENGTH: 32
<212> TYPE: PRT
<213> ORGANISM: Mus sp.

<400> SEQUENCE: 90

Arg Phe Ser Ile Thr Arg Asp Thr Ser Lys Asn Gln Phe Phe Leu Gln
1 5 10 15

Leu Asn Ser Val Thr Thr Glu Asp Thr Ala Thr Tyr Tyr Cys Ala Arg
20 25 30

<210> SEQ ID NO 91
<211> LENGTH: 32
<212> TYPE: PRT
<213> ORGANISM: Mus sp.

<400> SEQUENCE: 91

Lys Ala Thr Leu Thr Val Asp Lys Ser Ser Asn Thr Ala Tyr Met Glu
1 5 10 15

Leu Arg Ser Leu Thr Ser Ala Asp Ser Ala Val Tyr Tyr Cys Ala Arg
20 25 30

<210> SEQ ID NO 92
<211> LENGTH: 32
<212> TYPE: PRT
<213> ORGANISM: Mus sp.

<400> SEQUENCE: 92

Arg Phe Ala Phe Ser Leu Asp Thr Ser Ala Ser Thr Ala Tyr Leu Thr
1 5 10 15

Ile Asn Asn Leu Lys Asn Glu Asp Thr Ala Thr Tyr Phe Cys Ala Arg
20 25 30

<210> SEQ ID NO 93
<211> LENGTH: 32
<212> TYPE: PRT
<213> ORGANISM: Mus sp.

<400> SEQUENCE: 93

Arg Phe Thr Ile Ser Arg Asp Asp Ser Lys Ser Ser Val Tyr Leu Gln
1 5 10 15

Met Ser Ser Leu Arg Ala Glu Asp Thr Gly Ile Tyr Tyr Cys Thr Ser
20 25 30

<210> SEQ ID NO 94
<211> LENGTH: 32
<212> TYPE: PRT
<213> ORGANISM: Mus sp.

<400> SEQUENCE: 94

Arg Phe Thr Ile Ser Arg Asp Ile Ala Lys Asn Thr Leu Tyr Leu Gln
1 5 10 15

Met Ser Arg Leu Lys Ser Glu Asp Thr Ala Met Tyr Tyr Cys Val Arg
20 25 30

<210> SEQ ID NO 95
<211> LENGTH: 32
<212> TYPE: PRT
<213> ORGANISM: Mus sp.

<400> SEQUENCE: 95

-continued

```
Arg Ile Ser Ile Thr Arg Asp Pro Ser Lys Asn Gln Phe Phe Leu Lys
  1               5                  10                  15

Leu Asn Ser Val Thr Thr Glu Asp Thr Ala Thr Tyr Tyr Cys Ala Arg
             20                  25                  30


<210> SEQ ID NO 96
<211> LENGTH: 12
<212> TYPE: PRT
<213> ORGANISM: Mus sp.

<400> SEQUENCE: 96

Glu Ala Tyr Gly Tyr Asp Val Gly Tyr Phe Asp Tyr
  1               5                  10


<210> SEQ ID NO 97
<211> LENGTH: 14
<212> TYPE: PRT
<213> ORGANISM: Mus sp.

<400> SEQUENCE: 97

Arg Gly Asn Asn Tyr Tyr Gly Ser Ser Pro Trp Phe Ala Tyr
  1               5                  10


<210> SEQ ID NO 98
<211> LENGTH: 9
<212> TYPE: PRT
<213> ORGANISM: Mus sp.

<400> SEQUENCE: 98

Ser Asn Tyr Gly Asn Tyr Phe Asp Tyr
  1               5


<210> SEQ ID NO 99
<211> LENGTH: 11
<212> TYPE: PRT
<213> ORGANISM: Mus sp.

<400> SEQUENCE: 99

His His Tyr Gly Ser Ser Trp Tyr Phe Asp Val
  1               5                  10


<210> SEQ ID NO 100
<211> LENGTH: 13
<212> TYPE: PRT
<213> ORGANISM: Mus sp.

<400> SEQUENCE: 100

Gly Arg Leu Arg Phe Leu Phe Asp Tyr Ala Met Asp Tyr
  1               5                  10


<210> SEQ ID NO 101
<211> LENGTH: 15
<212> TYPE: PRT
<213> ORGANISM: Mus sp.

<400> SEQUENCE: 101

Gly Gly Lys Ile Phe Tyr Gly Ser Ser Tyr Asp Pro Phe Ala Tyr
  1               5                  10                  15


<210> SEQ ID NO 102
<211> LENGTH: 11
<212> TYPE: PRT
<213> ORGANISM: Mus sp.

<400> SEQUENCE: 102
```

Trp Gly Gln Gly Thr Thr Leu Thr Val Ser Ser
1 5 10

<210> SEQ ID NO 103
<211> LENGTH: 11
<212> TYPE: PRT
<213> ORGANISM: Mus sp.

<400> SEQUENCE: 103

Trp Gly Gln Gly Thr Leu Val Thr Val Ser Ser
1 5 10

<210> SEQ ID NO 104
<211> LENGTH: 11
<212> TYPE: PRT
<213> ORGANISM: Mus sp.

<400> SEQUENCE: 104

Trp Gly Gln Gly Thr Thr Leu Thr Val Ser Ser
1 5 10

<210> SEQ ID NO 105
<211> LENGTH: 11
<212> TYPE: PRT
<213> ORGANISM: Mus sp.

<400> SEQUENCE: 105

Trp Gly Ala Gly Thr Thr Val Thr Val Ser Ala
1 5 10

<210> SEQ ID NO 106
<211> LENGTH: 11
<212> TYPE: PRT
<213> ORGANISM: Mus sp.

<400> SEQUENCE: 106

Trp Gly Gln Gly Thr Ser Val Thr Val Ser Ser
1 5 10

<210> SEQ ID NO 107
<211> LENGTH: 11
<212> TYPE: PRT
<213> ORGANISM: Mus sp.

<400> SEQUENCE: 107

Trp Gly Gln Gly Thr Leu Val Thr Val Ser Ser
1 5 10

<210> SEQ ID NO 108
<211> LENGTH: 423
<212> TYPE: DNA
<213> ORGANISM: Mus sp.
<220> FEATURE:
<221> NAME/KEY: CDS
<222> LOCATION: (1)..(423)

<400> SEQUENCE: 108 atg aga gtg ctg att ctt ttg tgg ctg ttc aca gcc ttt cct ggt atc 48
Met Arg Val Leu Ile Leu Leu Trp Leu Phe Thr Ala Phe Pro Gly Ile
1 5 10 15 ctg tct gat gtg cag ctt cag gag tcg gga cct ggc ctg gtg aaa cct 96
Leu Ser Asp Val Gln Leu Gln Glu Ser Gly Pro Gly Leu Val Lys Pro
20 25 30 tct cag tct ctg tcc ctc acc tgc act gtc act ggc tcc tca atc acc 144

-continued

```
Ser Gln Ser Leu Ser Leu Thr Cys Thr Val Thr Gly Ser Ser Ile Thr
        35                  40                  45

agt gat tat gcc tgg cac tgg atc cgg cag ttt cca gga aac aaa ctg      192
Ser Asp Tyr Ala Trp His Trp Ile Arg Gln Phe Pro Gly Asn Lys Leu
     50                  55                  60

gag tgg atg ggc tac ata agc ttc agt ggt agc act ggc tac aac cca      240
Glu Trp Met Gly Tyr Ile Ser Phe Ser Gly Ser Thr Gly Tyr Asn Pro
 65                  70                  75                  80

tct ctc aaa agt cga ttc tct atc act cga gac aca tcc aag aac cag      288
Ser Leu Lys Ser Arg Phe Ser Ile Thr Arg Asp Thr Ser Lys Asn Gln
                 85                  90                  95

ttc ttc ctg cag ttg aat tct gtg act act gag gac aca gcc aca tat      336
Phe Phe Leu Gln Leu Asn Ser Val Thr Thr Glu Asp Thr Ala Thr Tyr
            100                 105                 110

tac tgt gca aga gag gct tat ggt tat gac gtg ggc tac ttt gac tac      384
Tyr Cys Ala Arg Glu Ala Tyr Gly Tyr Asp Val Gly Tyr Phe Asp Tyr
        115                 120                 125

tgg ggc caa ggc acc act ctc acc gtc tcc tca gct agc                  423
Trp Gly Gln Gly Thr Thr Leu Thr Val Ser Ser Ala Ser
    130                 135                 140


<210> SEQ ID NO 109
<211> LENGTH: 141
<212> TYPE: PRT
<213> ORGANISM: Mus sp.

<400> SEQUENCE: 109

Met Arg Val Leu Ile Leu Leu Trp Leu Phe Thr Ala Phe Pro Gly Ile
  1               5                  10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Ser Ser Ile Thr
        35                  40                  45

Ser Asp Tyr Ala Trp His Trp Ile Arg Gln Phe Pro Gly Asn Lys Leu
     50                  55                  60

Glu Trp Met Gly Tyr Ile Ser Phe Ser Gly Ser Thr Gly Tyr Asn Pro
 65                  70                  75                  80

Ser Leu Lys Ser Arg Phe Ser Ile Thr Arg Asp Thr Ser Lys Asn Gln
                 85                  90                  95

Phe Phe Leu Gln Leu Asn Ser Val Thr Thr Glu Asp Thr Ala Thr Tyr
            100                 105                 110

Tyr Cys Ala Arg Glu Ala Tyr Gly Tyr Asp Val Gly Tyr Phe Asp Tyr
        115                 120                 125

Trp Gly Gln Gly Thr Thr Leu Thr Val Ser Ser Ala Ser
    130                 135                 140


<210> SEQ ID NO 110
<211> LENGTH: 438
<212> TYPE: DNA
<213> ORGANISM: Mus sp.
<220> FEATURE:
<221> NAME/KEY: CDS
<222> LOCATION: (1)..(438)

<400> SEQUENCE: 110

gtc gac atg gga tgg agc ggg atc ttt atc ttt ctc ctg tca gga act       48
Val Asp Met Gly Trp Ser Gly Ile Phe Ile Phe Leu Leu Ser Gly Thr
  1               5                  10                  15

gca ggt gtc ctc tct gag gtc cag ctg caa cag tct gga cct gag ctg       96
Ala Gly Val Leu Ser Glu Val Gln Leu Gln Gln Ser Gly Pro Glu Leu
```

-continued

```
             20                  25                  30

gtg aag cct ggg gct tca gtg agg ata tcc tgc aag acc tct gga tac      144
Val Lys Pro Gly Ala Ser Val Arg Ile Ser Cys Lys Thr Ser Gly Tyr
        35                  40                  45

aca atc act gaa tac acc atg cac tgg atg aag cag agc cat gaa aag      192
Thr Ile Thr Glu Tyr Thr Met His Trp Met Lys Gln Ser His Glu Lys
     50                  55                  60

agc ctt gag tgg att gga ggt att act cca aac act ggt gtt ctt agt      240
Ser Leu Glu Trp Ile Gly Gly Ile Thr Pro Asn Thr Gly Val Leu Ser
 65                  70                  75                  80

gac aat cag aag ttc agg ggc aag gcc aca ttg act gta gac aag tcc      288
Asp Asn Gln Lys Phe Arg Gly Lys Ala Thr Leu Thr Val Asp Lys Ser
                 85                  90                  95

tcc aac aca gcc tac atg gag ctc cgc agc ctg aca tct gcg gat tct      336
Ser Asn Thr Ala Tyr Met Glu Leu Arg Ser Leu Thr Ser Ala Asp Ser
            100                 105                 110

gca gtc tat tac tgt gca aga agg gga aat aat tac tac ggt agt agt      384
Ala Val Tyr Tyr Cys Ala Arg Arg Gly Asn Asn Tyr Tyr Gly Ser Ser
        115                 120                 125

ccc tgg ttt gct tac tgg ggc caa ggg act ctg gtc acc gtc tcc gca      432
Pro Trp Phe Ala Tyr Trp Gly Gln Gly Thr Leu Val Thr Val Ser Ala
    130                 135                 140

gct agc                                                              438
Ala Ser
145


<210> SEQ ID NO 111
<211> LENGTH: 146
<212> TYPE: PRT
<213> ORGANISM: Mus sp.

<400> SEQUENCE: 111

Val Asp Met Gly Trp Ser Gly Ile Phe Ile Phe Leu Leu Ser Gly Thr
  1               5                  10                  15

Ala Gly Val Leu Ser Glu Val Gln Leu Gln Gln Ser Gly Pro Glu Leu
             20                  25                  30

Val Lys Pro Gly Ala Ser Val Arg Ile Ser Cys Lys Thr Ser Gly Tyr
        35                  40                  45

Thr Ile Thr Glu Tyr Thr Met His Trp Met Lys Gln Ser His Glu Lys
     50                  55                  60

Ser Leu Glu Trp Ile Gly Gly Ile Thr Pro Asn Thr Gly Val Leu Ser
 65                  70                  75                  80

Asp Asn Gln Lys Phe Arg Gly Lys Ala Thr Leu Thr Val Asp Lys Ser
                 85                  90                  95

Ser Asn Thr Ala Tyr Met Glu Leu Arg Ser Leu Thr Ser Ala Asp Ser
            100                 105                 110

Ala Val Tyr Tyr Cys Ala Arg Arg Gly Asn Asn Tyr Tyr Gly Ser Ser
        115                 120                 125

Pro Trp Phe Ala Tyr Trp Gly Gln Gly Thr Leu Val Thr Val Ser Ala
    130                 135                 140

Ala Ser
145


<210> SEQ ID NO 112
<211> LENGTH: 417
<212> TYPE: DNA
<213> ORGANISM: Mus sp.
<220> FEATURE:
<221> NAME/KEY: CDS
```

```
<222> LOCATION: (1)..(417)

<400> SEQUENCE: 112

atg gat tgg gtg tgg acc ttg cta ttc ctg atg gca gct gcc caa agt       48
Met Asp Trp Val Trp Thr Leu Leu Phe Leu Met Ala Ala Ala Gln Ser
  1               5                  10                  15

gcc caa gca cag atc cag ttg gtg cag tct gga cct gag ctg aag aag       96
Ala Gln Ala Gln Ile Gln Leu Val Gln Ser Gly Pro Glu Leu Lys Lys
             20                  25                  30

cct gga gag aca gtc aag atc tcc tgc aag gct tct gga tat tcc ttc      144
Pro Gly Glu Thr Val Lys Ile Ser Cys Lys Ala Ser Gly Tyr Ser Phe
         35                  40                  45

aga aac tat gga atg aac tgg gtg agt cag cct cca gga aag ggt tta      192
Arg Asn Tyr Gly Met Asn Trp Val Ser Gln Pro Pro Gly Lys Gly Leu
     50                  55                  60

gaa tgg atg ggc tgg ata aac acc tac act gga gag cca aca tat gct      240
Glu Trp Met Gly Trp Ile Asn Thr Tyr Thr Gly Glu Pro Thr Tyr Ala
 65                  70                  75                  80

gat gac ttc aag gga cgg ttt gcc ttc tct ttg gac acc tct gcc agt      288
Asp Asp Phe Lys Gly Arg Phe Ala Phe Ser Leu Asp Thr Ser Ala Ser
                 85                  90                  95

act gcc tat ttg acg atc aac aac ctc aaa aat gaa gac acg gct aca      336
Thr Ala Tyr Leu Thr Ile Asn Asn Leu Lys Asn Glu Asp Thr Ala Thr
            100                 105                 110

tat ttc tgt gca aga tcg aat tat ggt aac tac ttt gac tac tgg ggc      384
Tyr Phe Cys Ala Arg Ser Asn Tyr Gly Asn Tyr Phe Asp Tyr Trp Gly
        115                 120                 125

cag ggc acc act ctc act gtc tct gca gct agc                          417
Gln Gly Thr Thr Leu Thr Val Ser Ala Ala Ser
    130                 135


<210> SEQ ID NO 113
<211> LENGTH: 139
<212> TYPE: PRT
<213> ORGANISM: Mus sp.

<400> SEQUENCE: 113

Met Asp Trp Val Trp Thr Leu Leu Phe Leu Met Ala Ala Ala Gln Ser
  1               5                  10                  15

Ala Gln Ala Gln Ile Gln Leu Val Gln Ser Gly Pro Glu Leu Lys Lys
             20                  25                  30

Pro Gly Glu Thr Val Lys Ile Ser Cys Lys Ala Ser Gly Tyr Ser Phe
         35                  40                  45

Arg Asn Tyr Gly Met Asn Trp Val Ser Gln Pro Pro Gly Lys Gly Leu
     50                  55                  60

Glu Trp Met Gly Trp Ile Asn Thr Tyr Thr Gly Glu Pro Thr Tyr Ala
 65                  70                  75                  80

Asp Asp Phe Lys Gly Arg Phe Ala Phe Ser Leu Asp Thr Ser Ala Ser
                 85                  90                  95

Thr Ala Tyr Leu Thr Ile Asn Asn Leu Lys Asn Glu Asp Thr Ala Thr
            100                 105                 110

Tyr Phe Cys Ala Arg Ser Asn Tyr Gly Asn Tyr Phe Asp Tyr Trp Gly
        115                 120                 125

Gln Gly Thr Thr Leu Thr Val Ser Ala Ala Ser
    130                 135


<210> SEQ ID NO 114
<211> LENGTH: 371
<212> TYPE: DNA
```

```
<213> ORGANISM: Mus sp.
<220> FEATURE:
<221> NAME/KEY: CDS
<222> LOCATION: (1)..(369)

<400> SEQUENCE: 114

gaa gtg aag ctt gag gag tct gga gga ggc ttg gtg caa cct gga gga       48
Glu Val Lys Leu Glu Glu Ser Gly Gly Gly Leu Val Gln Pro Gly Gly
  1               5                  10                  15

tcc atg aaa ctc tct tgt gct gcc tct gga ttc act ttt ggt gac gcc       96
Ser Met Lys Leu Ser Cys Ala Ala Ser Gly Phe Thr Phe Gly Asp Ala
             20                  25                  30

tgg atg tac tgg gtc cgc cag tct cca gag aag ggg ctt gag tgg gtt      144
Trp Met Tyr Trp Val Arg Gln Ser Pro Glu Lys Gly Leu Glu Trp Val
         35                  40                  45

gct gaa att aga agc aaa gct cat aat cat gca aca tac tat gct gag      192
Ala Glu Ile Arg Ser Lys Ala His Asn His Ala Thr Tyr Tyr Ala Glu
     50                  55                  60

tct gtg aaa ggg agg ttc acc atc tca aga gat gat tcc aaa agt agt      240
Ser Val Lys Gly Arg Phe Thr Ile Ser Arg Asp Asp Ser Lys Ser Ser
 65                  70                  75                  80

gtc tac ctg caa atg agc agc tta aga gct gaa gac act ggc att tat      288
Val Tyr Leu Gln Met Ser Ser Leu Arg Ala Glu Asp Thr Gly Ile Tyr
                 85                  90                  95

tac tgt acc tcc cat cac tac ggc agt agc tgg tac ttc gat gtc tgg      336
Tyr Cys Thr Ser His His Tyr Gly Ser Ser Trp Tyr Phe Asp Val Trp
            100                 105                 110

ggc gca ggg acc acg gtc act gtc tcc tca gct ag                       371
Gly Ala Gly Thr Thr Val Thr Val Ser Ser Ala
        115                 120


<210> SEQ ID NO 115
<211> LENGTH: 123
<212> TYPE: PRT
<213> ORGANISM: Mus sp.

<400> SEQUENCE: 115

Glu Val Lys Leu Glu Glu Ser Gly Gly Gly Leu Val Gln Pro Gly Gly
  1               5                  10                  15

Ser Met Lys Leu Ser Cys Ala Ala Ser Gly Phe Thr Phe Gly Asp Ala
             20                  25                  30

Trp Met Tyr Trp Val Arg Gln Ser Pro Glu Lys Gly Leu Glu Trp Val
         35                  40                  45

Ala Glu Ile Arg Ser Lys Ala His Asn His Ala Thr Tyr Tyr Ala Glu
     50                  55                  60

Ser Val Lys Gly Arg Phe Thr Ile Ser Arg Asp Asp Ser Lys Ser Ser
 65                  70                  75                  80

Val Tyr Leu Gln Met Ser Ser Leu Arg Ala Glu Asp Thr Gly Ile Tyr
                 85                  90                  95

Tyr Cys Thr Ser His His Tyr Gly Ser Ser Trp Tyr Phe Asp Val Trp
            100                 105                 110

Gly Ala Gly Thr Thr Val Thr Val Ser Ser Ala
        115                 120


<210> SEQ ID NO 116
<211> LENGTH: 429
<212> TYPE: DNA
<213> ORGANISM: Mus sp.
<220> FEATURE:
<221> NAME/KEY: CDS
<222> LOCATION: (1)..(429)
```

<400> SEQUENCE: 116

```
atg gac ttt ggg ctc agc ttg gtt ttc ctt gtc ctt gtt tta aaa ggt       48
Met Asp Phe Gly Leu Ser Leu Val Phe Leu Val Leu Val Leu Lys Gly
  1               5                  10                  15

gtc cag tgt gaa gtc aag ctg gtg gag tca ggg gga ggc tca gtg cag       96
Val Gln Cys Glu Val Lys Leu Val Glu Ser Gly Gly Gly Ser Val Gln
             20                  25                  30

cct gga ggg tcc ctg aaa ctc tcc tgt gca acc tct gga ttc att ttc      144
Pro Gly Gly Ser Leu Lys Leu Ser Cys Ala Thr Ser Gly Phe Ile Phe
         35                  40                  45

agt gac tat tac atg tat tgg gtt cgc cag act cca gag aag agg ctg      192
Ser Asp Tyr Tyr Met Tyr Trp Val Arg Gln Thr Pro Glu Lys Arg Leu
     50                  55                  60

gag tgg gtc gca tac att agt att ggt agt ggt aat acc tat tat cca      240
Glu Trp Val Ala Tyr Ile Ser Ile Gly Ser Gly Asn Thr Tyr Tyr Pro
 65                  70                  75                  80

gac act gta aag ggc cga ttc acc atc tcc aga gac att gcc aag aac      288
Asp Thr Val Lys Gly Arg Phe Thr Ile Ser Arg Asp Ile Ala Lys Asn
                 85                  90                  95

acc ctg tac ctg caa atg agc cgt ctg aag tct gag gac aca gcc atg      336
Thr Leu Tyr Leu Gln Met Ser Arg Leu Lys Ser Glu Asp Thr Ala Met
            100                 105                 110

tat tac tgt gta agg ggg aga tta cga ttc ctt ttc gac tat gct atg      384
Tyr Tyr Cys Val Arg Gly Arg Leu Arg Phe Leu Phe Asp Tyr Ala Met
        115                 120                 125

gac tat tgg ggt caa gga acc tca gtc acc gtc tcc tca gct agc          429
Asp Tyr Trp Gly Gln Gly Thr Ser Val Thr Val Ser Ser Ala Ser
    130                 135                 140
```

<210> SEQ ID NO 117
<211> LENGTH: 143
<212> TYPE: PRT
<213> ORGANISM: Mus sp.

<400> SEQUENCE: 117

```
Met Asp Phe Gly Leu Ser Leu Val Phe Leu Val Leu Val Leu Lys Gly
  1               5                  10                  15

Val Gln Cys Glu Val Lys Leu Val Glu Ser Gly Gly Gly Ser Val Gln
             20                  25                  30

Pro Gly Gly Ser Leu Lys Leu Ser Cys Ala Thr Ser Gly Phe Ile Phe
         35                  40                  45

Ser Asp Tyr Tyr Met Tyr Trp Val Arg Gln Thr Pro Glu Lys Arg Leu
     50                  55                  60

Glu Trp Val Ala Tyr Ile Ser Ile Gly Ser Gly Asn Thr Tyr Tyr Pro
 65                  70                  75                  80

Asp Thr Val Lys Gly Arg Phe Thr Ile Ser Arg Asp Ile Ala Lys Asn
                 85                  90                  95

Thr Leu Tyr Leu Gln Met Ser Arg Leu Lys Ser Glu Asp Thr Ala Met
            100                 105                 110

Tyr Tyr Cys Val Arg Gly Arg Leu Arg Phe Leu Phe Asp Tyr Ala Met
        115                 120                 125

Asp Tyr Trp Gly Gln Gly Thr Ser Val Thr Val Ser Ser Ala Ser
    130                 135                 140
```

<210> SEQ ID NO 118
<211> LENGTH: 432
<212> TYPE: DNA
<213> ORGANISM: Mus sp.

```
<220> FEATURE:
<221> NAME/KEY: CDS
<222> LOCATION: (1)..(432)

<400> SEQUENCE: 118

atg atg gtg tta agt ctt ctg tac ctg ttg aca gcc att cct ggt atc       48
Met Met Val Leu Ser Leu Leu Tyr Leu Leu Thr Ala Ile Pro Gly Ile
  1               5                  10                  15

ctg tct gat gta cag ctt cag gag tca gga cct gac ctc gtg aaa cct       96
Leu Ser Asp Val Gln Leu Gln Glu Ser Gly Pro Asp Leu Val Lys Pro
             20                  25                  30

tct cag tct ctg tct ctc acc tgc tct gtc act ggc tac tcc atc acc      144
Ser Gln Ser Leu Ser Leu Thr Cys Ser Val Thr Gly Tyr Ser Ile Thr
         35                  40                  45

agt ggt tat tac tgg aac tgg atc cgg cag ttt cca gga aac aaa ctg      192
Ser Gly Tyr Tyr Trp Asn Trp Ile Arg Gln Phe Pro Gly Asn Lys Leu
     50                  55                  60

gaa tgg gtg ggc tac tta agc tac gac ggt agc aaa agc cac aac cca      240
Glu Trp Val Gly Tyr Leu Ser Tyr Asp Gly Ser Lys Ser His Asn Pro
 65                  70                  75                  80

tct ctc aga aat cga atc tcc atc act cgt gac cca tct aag aac cag      288
Ser Leu Arg Asn Arg Ile Ser Ile Thr Arg Asp Pro Ser Lys Asn Gln
                 85                  90                  95

ttt ttc ctg aag ttg aat tct gtg act act gag gac aca gct aca tat      336
Phe Phe Leu Lys Leu Asn Ser Val Thr Thr Glu Asp Thr Ala Thr Tyr
            100                 105                 110

tac tgt gca aga ggg gga aag att ttt tac ggt agt agc tac gac ccg      384
Tyr Cys Ala Arg Gly Gly Lys Ile Phe Tyr Gly Ser Ser Tyr Asp Pro
        115                 120                 125

ttt gct tac tgg ggc caa ggg act ctg gtc acc gtc tcc tca gct agc      432
Phe Ala Tyr Trp Gly Gln Gly Thr Leu Val Thr Val Ser Ser Ala Ser
    130                 135                 140


<210> SEQ ID NO 119
<211> LENGTH: 144
<212> TYPE: PRT
<213> ORGANISM: Mus sp.

<400> SEQUENCE: 119

Met Met Val Leu Ser Leu Leu Tyr Leu Leu Thr Ala Ile Pro Gly Ile
  1               5                  10                  15

Leu Ser Asp Val Gln Leu Gln Glu Ser Gly Pro Asp Leu Val Lys Pro
             20                  25                  30

Ser Gln Ser Leu Ser Leu Thr Cys Ser Val Thr Gly Tyr Ser Ile Thr
         35                  40                  45

Ser Gly Tyr Tyr Trp Asn Trp Ile Arg Gln Phe Pro Gly Asn Lys Leu
     50                  55                  60

Glu Trp Val Gly Tyr Leu Ser Tyr Asp Gly Ser Lys Ser His Asn Pro
 65                  70                  75                  80

Ser Leu Arg Asn Arg Ile Ser Ile Thr Arg Asp Pro Ser Lys Asn Gln
                 85                  90                  95

Phe Phe Leu Lys Leu Asn Ser Val Thr Thr Glu Asp Thr Ala Thr Tyr
            100                 105                 110

Tyr Cys Ala Arg Gly Gly Lys Ile Phe Tyr Gly Ser Ser Tyr Asp Pro
        115                 120                 125

Phe Ala Tyr Trp Gly Gln Gly Thr Leu Val Thr Val Ser Ser Ala Ser
    130                 135                 140
```